US011690902B2

(12) United States Patent
Poznansky et al.

(10) Patent No.: US 11,690,902 B2
(45) Date of Patent: Jul. 4, 2023

(54) COXIELLA BURNETII EPITOPES FOR T CELL-TARGETED Q FEVER VACCINES

(71) Applicants: The General Hospital Corporation, Boston, MA (US); Epivax, Inc., Providence, RI (US); Innatoss Laboratories B.V., Oss (NL)

(72) Inventors: Mark C. Poznansky, Newton, MA (US); Ann Elizabeth Sluder, Bedford, MA (US); Timothy Alan Brauns, Roslindale, MA (US); Anne Searls De Groot, Providence, RI (US); Leonard Jeffrey Moise, Providence, RI (US); Anja Garritsen, Oss (NL); Anja Scholzen, Nijmegen (NL)

(73) Assignees: The General Hospital Corporation, Boston, MA (US); EpiVax, Inc., Providence, RI (US); Innatoss Laboratories B.V., Oss (NL)

( * ) Notice: Subject to any disclaimer, the term of this patent is extended or adjusted under 35 U.S.C. 154(b) by 0 days.

(21) Appl. No.: 16/982,141

(22) PCT Filed: Mar. 25, 2019

(86) PCT No.: PCT/US2019/023878
§ 371 (c)(1),
(2) Date: Sep. 18, 2020

(87) PCT Pub. No.: WO2019/183627
PCT Pub. Date: Sep. 26, 2019

(65) Prior Publication Data
US 2021/0113679 A1 Apr. 22, 2021

Related U.S. Application Data

(60) Provisional application No. 62/647,156, filed on Mar. 23, 2018.

(51) Int. Cl.
*A61K 39/02* (2006.01)
*A61K 39/04* (2006.01)
*A61K 39/00* (2006.01)
*C07K 14/195* (2006.01)

(52) U.S. Cl.
CPC ...... *A61K 39/0208* (2013.01); *A61K 39/0233* (2013.01); *A61K 39/04* (2013.01); *C07K 14/195* (2013.01); *A61K 2039/53* (2013.01); *A61K 2039/6043* (2013.01); *A61K 2039/70* (2013.01)

(58) Field of Classification Search
None
See application file for complete search history.

(56) References Cited

U.S. PATENT DOCUMENTS

2018/0133310 A1 5/2018 Hetherington

FOREIGN PATENT DOCUMENTS

| WO | WO 2006/108033 | 10/2006 |
| WO | WO 2017/051196 | 3/2017 |

OTHER PUBLICATIONS

Xiong et al. BMC Microbiol. 12(35): 1-10, 2012.*
Greenspan et al. Nature Biotechnol. 17: 936-937, 1999.*
Beare et al. Infect. Immun. 77: 642-656, 2009.*
Almeida et al., "Broad and cross-clade CD4+ T-cell responses elicited by a DNA vaccine encoding highly conserved and promiscuous HIV-1 M-group consensus peptides," PLoS One, 2012, 7(9):e45267, 12 pages.
Amara et al., "Long-lived poxvirus immunity, robust CD4 help, and better persistence of CD4 than CD8 T cells," J Virol., 2004, 78(8):3811-6.
Andoh et al., "T cells are essential for bacterial clearance, and gamma interferon, tumor necrosis factor alpha, and B cells are crucial for disease development in *Coxiella burnetii* infection in mice," Infect Immun., 2007, 75(7):3245-55.
Axelsson-Robertson et al., "Frequency of *Mycobacterium tuberculosis*-specific CD8+ T-cells in the course of anti-tuberculosis treatment," Int J Infect Dis., 2015, 32:23-9.
Baeten et al., "Standardized guinea pig model for Q fever vaccine reactogenicity," PLoS One, 2018, 13(10):e0205882.
Beare et al., "Candidate antigens for Q fever serodiagnosis revealed by immunoscreening of a *Coxiella burnetii* protein microarray," Clin Vaccine Immunol., 2008, 15(12):1771-9.
Bounds et al., "An immunoinformatics-derived DNA vaccine encoding human class II T cell epitopes of Ebola virus, Sudan virus, and Venezuelan equine encephalitis virus is immunogenic in HLA transgenic mice," Hum Vaccin Immunother., 2017, 13(12):2824-36.
Brauns et al., "Could mycobacterial Hsp70-containing fusion protein lead the way to an affordable therapeutic cancer vaccine?" Expert Rev Vaccines, 2015, 14(3):435-446.
Buchli et al., "Real-time measurement of in vitro peptide binding to soluble HLA-A*0201 by fluorescence polarization," Biochemistry, 2004, 43(46):14852-63.
Buttrum et al., "Both Major Histocompatibility Complex Class I (MHC-I) and MHC-II Molecules are Required, while MHC-I Appears to Play a Critical Role in Host Defense against Primary *Coxiella burnetii* Infection," Infect Immun., 2018, 86(4):e00602-17.
Calarota et al., "Enumeration and characterization of human memory T cells by enzyme-linked immunospot assays," Clin Dev Immunol., 2013, 2013:637649, 9 pages.
Carey et al., "The *Coxiella burnetii* Dot/Icm system delivers a unique repertoire of type IV effectors into host cells and is required for intracellular replication," PLoS Pathog., 2011, 7(5):e1002056, 19 pages.

(Continued)

*Primary Examiner* — S. Devi
(74) *Attorney, Agent, or Firm* — Fish & Richardson P.C.

(57) ABSTRACT

Compositions and methods for inducing a protective immune response against *Coxiella burnetii*, to reduce a subject's risk of developing Q fever.

13 Claims, 14 Drawing Sheets

Specification includes a Sequence Listing.

(56) References Cited

OTHER PUBLICATIONS

Chao et al., "Identification, cloning, and expression of potential diagnostic markers for Q fever," Ann N Y Acad Sci., 2005, 1063:76-8.
Chen et al., "A systematic approach to evaluate humoral and cellular immune responses to *Coxiella burnetii* immunoreactive antigens," Clin Microbiol Infect., 2009, 15(Suppl 2):156-7.
Chen et al., "Identification of CD4+ T cell epitopes in *C. burnetii* antigens targeted by antibody responses," PLoS One, 2011, 6(3):e17712, 10 pages.
Chen et al., "Large-scale identification and translocation of type IV secretion substrates by *Coxiella burnetii*," Proc Natl Acad Sci USA, 2010, 107(50):21755-60.
Chentoufi et al., "Towards a rational design of an asymptomatic clinical herpes vaccine: the old, the new, and the unknown," Clin Dev Immunol., 2012, 2012:187585, 17 pages.
Chiu et al., "A review of the efficacy of human Q fever vaccine registered in Australia," NSW Public Health Bull., 2007, 18(7-8):133-6.
Coleman et al., "Proteome and antigen profiling of *Coxiella burnetii* developmental forms," Infect Immun., 2007, 75(1):290-8.
Comas et al., "Human T cell epitopes of *Mycobacterium tuberculosis* are evolutionarily hyperconserved," Nat Genet., 2010, 42(6):498-503.
Coughlan et al., "Heterologous Two-Dose Vaccination with Simian Adenovims and Poxvirus Vectors Elicits Long-Lasting Cellular Immunity to Influenza Virus A in Healthy Adults," EBioMedicine, 2018, 29:146-154.
De Groot et al., "Reducing risk, improving outcomes: bioengineering less immunogenic protein therapeutics," Clin Immunol., 2009, 131(2):189-201.
Dellacasagrande et al., "IFN-gamma-mediated control of *Coxiella burnetii* survival in monocytes: the role of cell apoptosis and TNF," J Immunol., 1999, 162(4):2259-65.
Desnues et al., "Role of specific antibodies in *Coxiella burnetii* infection of macrophages," Clin Microbiol Infect., 2009, 15(Suppl 2):161-2.
Eldin et al., "From Q Fever to *Coxiella burnetii* Infection: a Paradigm Change," Clin Microbiol Rev., 2017, 30(1):115-90.
Ernst, "Antigenic Variation and Immune Escape in the MTBC," Adv Exp Med Biol., 2017, 1019:171-90.
Flores-Ramirez et al., "Reliable tool for detection of novel *Coxiella burnetii* antigens, using immobilized human polyclonal antibodies," J Chromatogr B, 2017, 1047:84-91.
Fonseca et al., "Identification of novel consensus CD4 T-cell epitopes from clade B HIV-1 whole genome that are frequently recognized by HIV-1 infected patients," AIDS, 2006, 20(18):2263-73.
Gefenaite et al., "Effectiveness of the Q fever vaccine: a meta-analysis," Vaccine, 2011, 29(3):395-8.
Gerlach et al., "*Coxiella burnetii* immunogenic proteins as a basis for new Q fever diagnostic and vaccine development," Acta Virol., 2017, 61(3):377-90.
Ghigo et al., "*Coxiella burnetii* survival in THP-1 monocytes involves the impairment of phagosome maturation: IFN-gamma mediates its restoration and bacterial killing," J Immunol., 2002, 169(8):4488-95.
Gilbert, "T-cell-inducing vaccines—what's the future," Immunology, 2012, 135(1):19-26.
Gonzalez-Galarza et al., "Allele frequency net 2015 update: new features for HLA epitopes, KIR and disease and HLA adverse dmg reaction associations," Nucleic Acids Res., 2015, 43(D1):D784-8.
Green et al., "Chimpanzee adenovims and MVA-vectored respiratory syncytial virus vaccine is safe and expands humoral and cellular immunity in adults," Sci Transl Med., 2015, 7(300):300ra126, 17 pages.
Hammarlund et al., "Antiviral immunity following smallpox virus infection: a case-control study," J Virol., 2010, 84(24):12754-60.
Humphres et al., "Role of antibody in *Coxiella burnetii* infection," Infect Immun., 1981, 31(2):641-5.
Humphreys et al., "Novel viral vectors in infectious diseases," Immunology, 2018, 153(1):1-9.
International Preliminary Report on Patentability in International Appln. No. PCT/US2019/023878, dated Oct. 8, 2020, 7 pages.
International Search Report and Written Opinion in International Appln. No. PCT/US2019/023878, dated Jul. 30, 2019, 10 pages.
Izzo et al., "Markers of cell-mediated immunity after vaccination with an inactivated, whole-cell Q fever vaccine," J Infect Dis., 1988, 157(4):781-9.
Izzo et al., "Variation in interferon-gamma responses to *Coxiella burnetii* antigens with lymphocytes from vaccinated or naturally infected subjects," Clin Exp Immunol., 1993, 94(3):507-15.
Jerrells et al., "Detection of long-term cellular immunity to *Coxiella burneti* as assayed by lymphocyte transformation," Infect Immun., 1975, 11(2):280-6.
Jiao et al., "Serological characterization of surface-exposed proteins of *Coxiella burnetii*," Microbiology, 2014, 160(Pt 12):2718-31.
Kampschreur et al., "Chronic Q fever diagnosis—consensus guideline versus expert opinion," Emerg Infect Dis., 2015, 21(7):1183-8.
Kampschreur et al., "Prevalence of chronic Q fever in patients with a history of cardiac valve surgery in an area where *Coxiella burnetii* is epidemic," Clin Vaccine Immunol., 2012, 19(8):1165-9.
Kampschreur et al., "Screening for Coxiella burnetii seroprevalence in chronic Q fever high-risk groups reveals the magnitude of the Dutch Q fever outbreak," Epidemiol Infect., 2013, 141(4):847-51.
Karagiannis et al., "Investigation of a Q fever outbreak in a rural area of The Netherlands," Epidemiol Infect., 2009, 137(9):1283-94.
Karch et al., "Vaccine technologies: From whole organisms to rationally designed protein assemblies," Biochem Pharmacol., 2016, 120:1-14.
Kersh et al., "Antimicrobial therapies for Q fever," Expert Rev Anti Infect Ther., 2013, 11(11):1207-1214.
Kersh et al., "Long-Term immune responses to *Coxiella burnetii* after vaccination," Clin Vaccine Immunol., 2013, 20(2):129-33.
Kowalczewska et al., "Proteomics paves the way for Q fever diagnostics," Genome Med., 2011, 3(7):50, 15 pages.
Kuley et al., "First Complete Genome Sequence of the Dutch Veterinary *Coxiella burnetii* Strain NL3262, Originating from the Largest Global Q Fever Outbreak, and Draft Genome Sequence of Its Epidemiologically Linked Chronic Human Isolate NLhu3345937," Genome Announc., 2016, 4(2):e00245-16, 2 pages.
Lamonaca et al., "Conserved hepatitis C virus sequences are highly immunogenic for CD4(+) T cells: implications for vaccine development," Hepatology, 1999, 30(4):1088-98.
Leblanc et al., "VaxCelerate II: Rapid development of a self-assembling vaccine for Lassa fever," Human Vaccines & Immunotherapeutics, 2014, 10(10):3022-3038.
Levy et al., "Comparison of different antibiotic regimens for therapy of 32 cases of Q fever endocarditis," Antimicrob Agents Chemother., 1991, 35(3):533-7.
Li et al., "Protective immunity against Q fever induced with a recombinant P1 antigen fused with HspB of *Coxiella burnetii*," Ann NY Acad Sci., 2005, 1063:130-42.
Li et al., "TCRbeta repertoire of CD4+ and CD8+ T cells is distinct in richness, distribution, and CDR3 amino acid composition," J Leukoc Biol., 2016, 99(3):505-13.
Lu, "Heterologous Prime-Boost Vaccination," Curr Opin Immunol., 2009, 21(3):346-351.
Luhrmann et al., "Inhibition of pathogen-induced apoptosis by a *Coxiella burnetii* type IV effector protein," Proc Natl Acad Sci USA, 2010, 107(44):18997-9001.
Madariaga et al., "Q fever: a biological weapon in your backyard," Lancet Infect Dis., 2003, 3(11):709-21.
Mangalam et al., "Identification of T cell epitopes on human proteolipid protein and induction of experimental autoimmune encephalomyelitis in HLA class II-transgenic mice," Eur J Immunol., 2004, 34(1):280-90.
Marmion et al., "Vaccine prophylaxis of abattoir-associated Q fever: eight years' experience in Australian abattoirs," Epidemiol Infect., 1990, 104(2):275-87.
Moise et al., "Immunization with cross-conserved H1N1 influenza CD4+ T-cell epitopes lowers viral burden in HLA DR3 transgenic mice," Hum Vaccin Immunother., 2013, 9(10):2060-8.

(56) References Cited

OTHER PUBLICATIONS

Moise et al., "iVAX: An integrated toolkit for the selection and optimization of antigens and the design of epitope-driven vaccines," Hum Vaccin Immunother., 2015, 11(9):2312-21.
Moise et al., "The two-faced T cell epitope: examining the host-microbe interface with JanusMatrix," Hum Vaccin Immunother., 2013, 9(7):1577-86.
Moise et al., "Universal H1N1 influenza vaccine development: identification of consensus class II hemagglutinin and neuraminidase epitopes derived from strains circulating between 1980 and 2011," Hum Vaccin Immunother., 2013, 9(7):1598-607.
Morroy et al., "Population Screening for Chronic Q-Fever Seven Years after a Major Outbreak," PLoS One, 2015, 10(7):e0131777, 8 pages.
Morroy et al., "The health status of a village population, 7 years after a major Q fever outbreak," Epidemiol Infect., 2016, 144(6):1153-62.
Nyendak et al., "*Mycobacterium tuberculosis* specific CD8(+) T cells rapidly decline with antituberculosis treatment," PLoS One, 2013, 8(12):e81564, 10 pages.
Papadioti et al., "A proteomic approach to investigate the differential antigenic profile of two *Coxiella burnetii* strains," J Proteomics, 2011, 74(7):1150-9.
Pearce et al., "Functional characterization of MHC class II-restricted CD8+CD4- and CD8-CD4-T cell responses to infection in CD4-/- mice," J Immunol., 2004, 173(4):2494-9.
Peng et al., "Development of a lipopolysaccharide-targeted peptide mimic vaccine against Q fever," J Immunol., 2012, 189(10):4909-20.
Penna et al., "Intrahepatic and circulating HLA class II-restricted, hepatitis C virus-specific T cells: functional characterization in patients with chronic hepatitis C," Hepatology, 2002, 35(5):1225-36.
Ranasinghe et al., "Antiviral CD8(+) T Cells Restricted by Human Leukocyte Antigen Class II Exist during Natural HIV Infection and Exhibit Clonal Expansion," Immunity, 2016, 45(4):917-30.
Read et al., "Role of CD4+ and CD8+ T cells in clearance of primary pulmonary infection with *Coxiella burnetii*," Infect Immun., 2010, 78(7):3019-26.
Reeves et al., "Q-vaxcelerate: A distributed development approach for a new *Coxiella burnetii* vaccine," Hum Vaccin Immunother., 2017, 13(12):2977-81.
Ruiz et al., "Vaccination against Q fever for biodefense and public health indications," Front Microbiol., 2014, 5:726, 8 pages.
Schipper et al., "HLA gene and haplotype frequencies in Dutch blood donors," Tissue Antigens, 1996, 48(5):562-74.
Scholzen et al., "Promiscuous *Coxiella burnetii* CD4 Epitope Clusters Associated With Human Recall Responses are Candidates for a Novel T-Cell Targeted Multi-Epitope Q Fever Vaccine," Front. Immunol., 2019, 10:207, 22 pages.
Sekeyová et al., "Characterization of antigens for Q fever serodiagnostics," Acta Virol., 2010, 54(3):173-80.
Sekeyová et al., "Identification of protein candidates for the serodiagnosis of Q fever endocarditis by an immunoproteomic approach," Eur J Clin Microbiol Infect Dis., 2009, 28(3):287-95.
Sette et al., "Nine major HLA class I supertypes account for the vast preponderance of HLA-A and -B polymorphism," Immunogenetics, 1999, 50(3-4):201-12.
Shetsov et al., "Heat Shock Protein-Peptide and HSP-Based Immunotherapies for the Treatment of Cancer," Front Immunol., 2016, 7:171, 7 pages.
Shiina et al., "Super high resolution for single molecule-sequence-based typing of classical HLA loci at the 8-digit level using next generation sequencers," Tissue Antigens, 2012, 80(4):305-16.
Sidney et al., "HLA class I supertypes: a revised and updated classification," BMC Immunol., 2008, 9:1, 15 pages.
Southwood et al., "Several common HLA-DR types share largely overlapping peptide binding repertoires," J Immunol., 1998, 160(7):3363-73.
Steere et al., "Antibiotic-refractory Lyme arthritis is associated with HLA-DR molecules that bind a Borrelia burgdorferi peptide," J Exp Med., 2006, 203(4):961-71.
Subbramanian et al., "Age-related changes in magnitude and diversity of cross-reactive CD4+ T-cell responses to the novel pandemic H1N1 influenza hemagglutinin," Hum Immunol., 2010, 71(10):957-63.
Tientcheu et al., "Immunological consequences of strain variation within the *Mycobacterium tuberculosis* complex," Eur J Immunol., 2017, 47(3):432-45.
Tigertt et al., "Airborne Q fever," Bacteriol Rev., 1961, 25(3):285-93.
Tobian et al., "*Mycobacterium tuberculosis* Heat Shock Fusion Protein Enhances Class I MHC Cross-Processing and -Presentation by B Lymphocytes," J Immunol., 2005, 174(9):5209-5214.
The UniProt Consortium, "UniProt: the universal protein knowledgebase," Nucleic Acids Res., 2018, 46(5):2699.
Van Schaik et al., "Molecular pathogenesis of the obligate intracellular bacterium *Coxiella burnetii*," Nat Rev Microbiol., 2013, 11(8):561-73.
Vigil et al., "Genome-wide profiling of humoral immune response to *Coxiella burnetii* infection by protein microarray," Proteomics, 2010, 10(12):2259-69.
Vigil et al., "Profiling the humoral immune response of acute and chronic Q fever by protein microarray," Mol Cell Proteomics, 2011, 10(10):M110.006304-1, 12 pages.
Voth et al., "The *Coxiella burnetii* ankyrin repeat domain-containing protein family is heterogeneous, with C-terminal truncations that influence Dot/Icm-mediated secretion," J Bacteriol., 2009, 191(13):4232-42.
Voth et al., "The *Coxiella burnetii* cryptic plasmid is enriched in genes encoding type IV secretion system substrates," J Bacteriol., 2011, 193(7):1493-503.
Wang et al., "Protein array of *Coxiella burnetii* probed with Q fever sera," Sci China Life Sci., 2013, 56(5):453-9.
Weber et al., "Identification of *Coxiella burnetii* type IV secretion substrates required for intracellular replication and *Coxiella*-containing vacuole formation," J Bacteriol., 2013, 195(17):3914-24.
Wei et al., "*Coxiella burnetii* antigen-stimulated dendritic cells mediated protection against *Coxiella burnetii* in BALB/c mice," J Infect Dis., 2011, 203(2):283-91.
Wilhelmsen et al., "Guinea pig abscess/hypersensitivity model for study of adverse vaccination reactions induced by use of Q fever vaccines," Comp Med., 2000, 50(4):374-8.
Xiong et al., "Exploratory study on Th1 epitope-induced protective immunity against *Coxiella burnetii* infection," PLoS One, 2014, 9(1):e87206, 8 pages.
Xiong et al., "Identification of *Coxiella burnetii* CD8+ T-Cell Epitopes and Delivery by Attenuated *Listeria monocytogenes* as a Vaccine Vector in a C57BL/6 Mouse Model," J Infect Dis., 2017, 215(10):1580-9.
Xiong et al., "Mice immunized with bone marrow-derived dendritic cells stimulated with recombinant *Coxiella burnetii* Com1 and Mip demonstrate enhanced bacterial clearance in association with a Th1 immune response," Vaccine, 2012, 30(48):6809-15.
Zhang et al., "Adenoviral vector-based strategies against infectious disease and cancer," Hum Vaccin Immunother., 2016, 12(8):2064-74.
Zhang et al., "Components of protective immunity," Adv Exp Med Biol., 2012, 984:91-104.
Zhang et al., "Formalin-inactivated *Coxiella burnetii* phase I vaccine-induced protection depends on B cells to produce protective IgM and IgG," Infect Immun., 2013, 81(6):2112-22.
Zhang et al., "Mechanisms of vaccine-induced protective immunity against *Coxiella burnetii* infection in BALB/c mice," J Immunol., 2007, 179(12):8372-80.

* cited by examiner

| | p1 | p2 | p3 | p4 | p5 | p6 | p7 | p8 | p9 | p10 | p11 | p12 | p13 | p14 | p15 | p16 |
|---|---|---|---|---|---|---|---|---|---|---|---|---|---|---|---|---|
| Group A controls | 0 | 0 | 0 | 2.1 | 0 | 0 | 0 | 0 | 0 | 0 | 0 | 0 | 0 | 0 | 0 | 0 |
| | 2.0 | 1.9 | 2.0 | 1.9 | 0 | 1.7 | 0 | 0 | 0 | 0 | 1.5 | 1.7 | 1.5 | 0 | 1.4 | 1.5 |
| | 0 | 0 | 0 | 0 | 0 | 0 | 0 | 0 | 0 | 0 | 0 | 0 | 0 | 0 | 0 | 0 |
| | 1.4 | 1.6 | 1.4 | 1.3 | 1.5 | 1.4 | 1.4 | 0 | 1.3 | 0 | 0 | 0 | 1.5 | 1.8 | 1.5 | 1.4 |
| | 0 | 0 | 0 | 0 | 0 | 0 | 0 | 0 | 0 | 0 | 0 | 0 | 0 | 1.3 | 1.4 | 1.3 |
| | 0 | 0 | 0 | 0 | 0 | 0 | 0 | 0 | 0 | 0 | 0 | 0 | 0 | 0 | 0 | 0 |
| | 0 | 0 | 0 | 1.9 | 2.0 | 0 | 0 | 0 | 0 | 0 | 0 | 0 | 0 | 0 | 0 | 2.0 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 3.0 | 3.2 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 1.5 | 0 | 0 | 0 | 0 |
| | 0 | 0 | 0 | 0 | 0 | 0 | 0 | 0 | 0 | 0 | 0 | 0 | 0 | 0 | 0 | 0 |
| | 1.6 | 0 | 0 | 1.7 | 0 | 0 | 0 | 0 | 0 | 0 | 0 | 0 | 0 | 0 | 0 | 0 |
| | 0 | 0 | 1.8 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 2.4 | 0 | 0 | 2.6 | 2.2 |
| | 0 | 0 | 0 | 0 | 0 | 0 | 0 | 0 | 0 | 0 | 0 | 0 | 0 | 0 | 0 | 0 |
| | 0 | 0 | 0 | 0 | 1.6 | 0 | 0 | 0 | 0 | 0 | 0 | 2.1 | 0 | 0 | 0 | 0 |
| | 0 | 1.5 | 0 | 0 | 0 | 0 | 0 | 0 | 0 | 0 | 1.3 | 0 | 0 | 0 | 0 | 0 |
| Group B asymptomatic | 0 | 0 | 0 | 5.4 | 0 | 0 | 0 | 0 | 0 | 0 | 0 | 4.3 | 0 | 0 | 5.1 | 0 |
| | 0 | 0 | 0 | 0 | 0 | 0 | 0 | 0 | 0 | 0 | 1.8 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 1.9 | 0 | 0 | 0 | 0 | 0 | 1.8 | 0 | 0 | 0 | 0 | 0 | 0 | 0 | 0 |
| | 0 | 0 | 0 | 0 | 2.2 | 0 | 0 | 2.2 | 0 | 0 | 0 | 2.9 | 0 | 2.7 | 0 | 3.1 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 2.8 | 0 | 0 | 0 | 0 | 3.9 | 0 | 4.4 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 1.3 | 0 | 1.4 | 0 | 0 | 0 | 0 | 0 | 0 | 0 | 0 | 1.5 | 0 |
| | 0 | 0 | 0 | 1.6 | 0 | 0 | 0 | 0 | 0 | 0 | 0 | 0 | 0 | 0 | 0 | 0 |
| | 0 | 0 | 0 | 1.5 | 1.7 | 0 | 0 | 0 | 0 | 0 | 0 | 2.6 | 0 | 0 | 0 | 0 |
| | 0 | 3.3 | 0 | 4.7 | 0 | 0 | 0 | 2.2 | 0 | 0 | 0 | 3.1 | 0 | 3.1 | 4.3 | 2.9 |
| | 0 | 0 | 0 | 1.3 | 1.3 | 1.3 | 1.2 | 0 | 0 | 1.3 | 0 | 0 | 0 | 0 | 0 | 0 |
| | 0 | 0 | 0 | 2.0 | 0 | 0 | 0 | 1.4 | 0 | 0 | 0 | 0 | 0 | 0 | 0 | 0 |
| | 0 | 1.4 | 0 | 4.0 | 0 | 0 | 0 | 1.4 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 2.0 | 0 | 0 | 1.6 | 0 | 0 | 0 | 0 | 0 | 0 | 0 | 1.7 | 0 | 0 | 0 | 0 |
| | 0 | 0 | 0 | 3.1 | 0 | 0 | 0 | 0 | 0 | 0 | 0 | 4.4 | 2.7 | 4.8 | 6.5 | 0 |
| | 1.4 | 1.7 | 1.6 | 1.4 | 0 | 1.5 | 1.9 | 1.5 | 1.4 | 1.3 | 1.6 | 1.7 | 1.5 | 2.1 | 1.7 | 1.7 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 1.6 | 1.4 | 1.5 | 0 | 0 | 0 | 1.4 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 1.8 | 0 | 0 | 0 | 0 | 0 | 0 | 1.6 | 0 | 0 | 0 | 1.7 | 0 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 2.1 | 0 | 0 | 0 | 0 | 0 | 0 | 0 | 0 | 2.0 | 2.1 | 0 | 2.9 | 3.4 | 2.1 |
| | 0 | 1.8 | 0 | 0 | 0 | 0 | 0 | 0 | 0 | 1.8 | 0 | 0 | 0 | 0 | 0 | 0 |
| | 0 | 1.8 | 0 | 2.4 | 0 | 0 | 0 | 0 | 0 | 0 | 0 | 0 | 0 | 2.0 | 1.6 | 0 |
| Group C symptomatic | 0 | 0 | 0 | 0 | 1.4 | 1.5 | 1.4 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 4.0 | 0 | 0 | 6.0 | 0 | 0 | 0 | 0 | 0 | 0 | 0 | 0 | 0 | 0 | 0 | 0 |
| | 0 | 3.4 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 |
| | 1.6 | 1.3 | 0 | 1.7 | 1.3 | 1.3 | 1.4 | 1.4 | 1.3 | 1.3 | 1.4 | 1.7 | 0 | 0 | 1.3 | 0 |
| | 0 | 5.2 | 0 | 4.0 | 0 | 0 | 0 | 0 | 2.2 | 0 | 2.5 | 0 | 4.4 | 7.9 | 0 | 0 |
| | 0 | 0 | 0 | 0 | 0 | 0 | 0 | 0 | 0 | 0 | 0 | 0 | 0 | 0 | 0 | 0 |
| | 0 | 0 | 0 | 1.9 | 0 | 0 | 0 | 0 | 0 | 1.4 | 1.5 | 0 | 0 | 1.6 | 1.7 | 0 |
| | 0 | 0 | 0 | 0 | 0 | 0 | 0 | 0 | 0 | 0 | 0 | 0 | 0 | 0 | 0 | 0 |
| | 0 | 0 | 0 | 11.4 | 0 | 0 | 0 | 0 | 0 | 0 | 7.7 | 0 | 5.5 | 12.7 | 0 | 0 |
| | 0 | 0 | 0 | 6.1 | 0 | 2.2 | 0 | 0 | 0 | 0 | 2.8 | 0 | 2.3 | 4.8 | 0 | 0 |
| | 0 | 7.5 | 0 | 0 | 0 | 2.1 | 0 | 0 | 0 | 0 | 0 | 0 | 6.0 | 3.9 | 0 | 0 |
| | 0 | 0 | 0 | 0 | 0 | 0 | 0 | 0 | 0 | 0 | 0 | 0 | 0 | 0 | 0 | 0 |
| | 0 | 2.1 | 0 | 20.3 | 0 | 2.4 | 0 | 2.8 | 0 | 0 | 0 | 9.0 | 0 | 5.5 | 15.4 | 0 |
| | 1.8 | 1.8 | 2.1 | 2.3 | 2.2 | 2.4 | 2.3 | 2.2 | 1.8 | 2.1 | 0 | 1.9 | 1.6 | 1.7 | 1.8 | 1.5 |
| | 0 | 0 | 0 | 0 | 0 | 0 | 0 | 1.9 | 0 | 0 | 0 | 0 | 0 | 3.1 | 2.1 | 0 |
| | 0 | 4.0 | 0 | 0 | 0 | 0 | 0 | 0 | 0 | 0 | 0 | 0 | 0 | 0 | 0 | 0 |
| | 0 | 2.2 | 0 | 0 | 0 | 0 | 0 | 0 | 0 | 0 | 0 | 0 | 0 | 2.7 | 0 | 0 |
| | 0 | 0 | 0 | 0 | 0 | 1.4 | 0 | 0 | 0 | 0 | 0 | 0 | 0 | 0 | 1.6 | 0 |
| | 3.6 | 0 | 0 | 3.1 | 0 | 0 | 0 | 0 | 0 | 1.8 | 0 | 2.2 | 0 | 0 | 0 | 0 |
| | 0 | 0 | 1.3 | 1.4 | 0 | 0 | 1.4 | 0 | 0 | 0 | 2.0 | 1.9 | 0 | 0 | 2.6 | 2.3 |

*FIG. 6A*

| | | p17 | p18 | p19 | p20 | p21 | p22 | p23 | p24 | p25 | p26 | p27 | p28 | p29 | p30 | p31 | p32 | p33 |
|---|---|---|---|---|---|---|---|---|---|---|---|---|---|---|---|---|---|---|
| Group A controls | | 0 | 0 | 0 | 0 | 0 | 0 | 0 | 0 | 0 | 0 | 0 | 0 | 0 | 0 | 0 | 0 | 0 |
| | | 0 | 1.5 | 0 | 0 | 1.7 | 1.8 | 1.5 | 1.6 | 1.5 | 1.6 | 0 | 0 | 0 | 0 | 1.6 | 1.6 | 1.4 |
| | | 0 | 0 | 0 | 0 | 0 | 0 | 0 | 0 | 0 | 0 | 0 | 0 | 0 | 0 | 0 | 0 | 0 |
| | | 1.7 | 0 | 1.6 | 0 | 1.6 | 1.5 | 0 | 0 | 0 | 0 | 0 | 0 | 0 | 0 | 0 | 0 | 0 |
| | | 1.4 | 1.4 | 1.4 | 1.4 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 1.8 | 2.1 | 0 | 1.8 | 0 | 0 | 0 | 0 | 0 | 0 | 0 | 0 | 0 |
| | | 0 | 4.1 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 2.9 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 4.6 | 0 | 0 | 0 | 0 | 0 | 0 | 0 | 0 | 0 | 0 | 0 | 2.7 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0.4 | 0.6 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 2.9 | 2.6 | 0 | 0 | 3.5 | 0 | 0 | 0 | 0 | 0 | 2.5 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 2.1 | 0 | 0 | 0 | 0 | 0 | 0 | 0 | 0 | 0 | 0 | 0 | 0 |
| | | 1.4 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| Group B asymptomatic | | 5.3 | 0 | 0 | 0 | 0 | 7.6 | 0 | 0 | 0 | 0 | 0 | 0 | 0 | 0 | 0 | 0 | 0 |
| | | 0 | 1.8 | 1.8 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 2.9 | 2.9 | 0 | 4.3 | 2.9 | 2.4 | 2.5 | 2.2 | 4.8 | 0 | 0 | 0 | 0 | 0 | 1.9 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 6.9 | 0 | 2.9 | 3.7 | 2.0 | 0 | 0 | 0 | 0 | 0 | 0 | 0 | 0 | 2.5 | 0 | 0 | 0 |
| | | 0 | 0 | 0 | 0 | 0 | 0 | 0 | 0 | 0 | 0 | 0 | 0 | 0 | 0 | 5.0 | 0 | 0 |
| | | 0 | 0 | 0 | 0 | 0 | 0 | 0 | 0 | 0 | 0 | 0 | 3.1 | 0 | 0 | 3.0 | 0 | 0 |
| | | 1.3 | 0 | 0 | 1.4 | 0 | 1.4 | 1.4 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 1.7 | 2.3 | 1.9 | 2.0 | 0 | 2.0 | 0 | 1.7 | 0 | 0 | 2.3 | 0 | 2.2 |
| | | 4.7 | 2.9 | 2.8 | 0 | 0 | 3.5 | 2.5 | 2.6 | 0 | 0 | 0 | 0 | 0 | 0 | 0 | 0 | 0 |
| | | 0 | 0 | 0 | 0 | 0 | 0 | 0 | 0 | 0 | 1.6 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 1.6 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 1.3 | 0 | 0 | 0 | 0 | 0 | 0 | 1.4 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 1.8 | 0 | 0 | 3.1 | 4.0 | 0 | 0 | 2.1 | 0 | 0 | 0 | 0 | 0 | 0 | 0 | 0 |
| | | 4.8 | 2.7 | 3.3 | 2.3 | 0 | 6.6 | 3.4 | 3.7 | 2.7 | 3.8 | 4.4 | 0 | 2.5 | 3.8 | 0 | 0 | 0 |
| | | 2.3 | 1.9 | 2.1 | 2.2 | 1.8 | 2.0 | 1.6 | 0 | 0 | 1.6 | 0 | 1.6 | 1.7 | 1.8 | 1.5 | 1.5 | 0 |
| | | 0 | 0 | 0 | 0 | 0 | 0 | 0 | 0 | 0 | 0 | 0 | 0 | X | X | 0 | 0 | 0 |
| | | 0 | 2.4 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 1.8 | 0 | 0 | 0 | 0 | 0 |
| | | 2.3 | 0 | 0 | 0 | 0 | 0 | 0 | 0 | 0 | 0 | 0 | 0 | 0 | 0 | 3.5 | 0 | 0 |
| | | 1.7 | 0 | 0 | 0 | 2.9 | 0 | 2.9 | 0 | 0 | 3.2 | 0 | 0 | 2.5 | 0 | 0 | 0 | 0 |
| | | 2.1 | 0 | 0 | 0 | 1.5 | 1.5 | 1.5 | 0 | 0 | 0 | 0 | 0 | 0 | 0 | 2.4 | 0 | 0 |
| | | 0 | 0 | 0 | 0 | 0 | 0 | 0.7 | 0.6 | 0.7 | 0 | 0 | 0 | 0 | 0 | 0 | 0 | 0 |
| | | 3.2 | 0 | 2.3 | 0 | 1.7 | 3.6 | 2.2 | 2.9 | 1.5 | 2.1 | 3.2 | 1.6 | 0 | 2.4 | 0 | 0 | 0 |
| | | 1.4 | 0 | 0 | 0 | 1.4 | 0 | 0 | 0 | 0 | 0 | 0 | 0 | 0 | 0 | 0 | 0 | 0 |
| | | 1.6 | 0 | 0 | 0 | 0 | 0 | 0 | 0 | 0 | 0 | 0 | 0 | 0 | 0 | 0 | 0 | 0 |
| Group C symptomatic | | 0 | 0 | 0 | 0 | 1.9 | 0 | 1.9 | 1.7 | 1.8 | 1.8 | 1.8 | 1.8 | 1.5 | 1.7 | 1.6 | 1.6 | 0 |
| | | 0 | 0 | 0 | 0 | 0 | 0 | 0 | 0 | 0 | 0 | 0 | 0 | 0 | 1.6 | 0 | 0 | 0 |
| | | 0 | 0 | 0 | 0 | 2.0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 | 0 | 0 | 0 | 0 | 0 |
| | | 0 | 0 | 1.3 | 1.3 | 0 | 0 | 0 | 0 | 0 | 0 | 0 | 0 | 0 | 0 | 0 | 0 | 0 |
| | | 1.3 | 0 | 1.4 | 1.4 | 1.5 | 1.6 | 1.6 | 1.5 | 0 | 0 | 0 | 1.4 | 1.5 | 1.4 | 0 | 0 | 0 |
| | | 4.0 | 2.6 | 3.0 | 0 | 0 | 11.4 | 5.3 | 5.6 | 0 | 3.4 | 0 | 0 | 0 | 0 | 0 | 0 | 0 |
| | | 1.6 | 0 | 0 | 0 | 0 | 0 | 0 | 0 | 0 | 0 | 0 | 0 | 0 | 0 | 0 | 2.2 | 0 |
| | | 2.0 | 0 | 1.6 | 1.7 | 1.7 | 1.8 | 0 | 2.2 | 0 | 0 | 0 | 0 | 0 | 2.3 | 0 | 0 | 0 |
| | | 0 | 0 | 0 | 0 | 1.5 | 1.6 | 1.6 | 0 | 0 | 1.5 | 1.5 | 1.5 | 1.6 | 0 | 0 | 0 | 0 |
| | | 12.3 | 8.2 | 9.5 | 0 | 0 | 10.4 | 3.9 | 5.2 | 0 | 0 | 4.6 | 0 | 0 | 0 | 0 | 0 | 0 |
| | | 3.1 | 1.8 | 2.7 | 2.0 | 2.1 | 7.9 | 3.0 | 4.2 | 0 | 1.9 | 2.2 | 1.8 | 1.9 | 1.7 | 1.5 | 1.6 | 1.5 |
| | | 3.7 | 0 | 3.8 | 0 | 2.0 | 0 | 2.0 | 0 | 0 | 0 | 0 | 0 | 0 | 0 | 0 | 0 | 0 |
| | | 0 | 0 | 0 | 0 | 4.1 | 0 | 0 | 0 | 0 | 0 | 0 | 0 | 0 | 0 | 0 | 0 | 0 |
| | | 8.3 | 4.3 | 6.0 | 0 | 0 | 17.3 | 3.8 | 6.6 | 0 | 0 | 3.0 | 0 | 0 | 0 | 0 | 0 | 0 |
| | | 1.6 | 1.6 | 0 | 1.5 | 0 | 1.7 | 0 | 0 | 0 | 0 | 0 | 0 | 0 | 0 | 0 | 0 | 0 |
| | | 2.5 | 0 | 1.6 | 0 | 0 | 1.8 | 1.5 | 0 | 0 | 1.6 | 0 | 0 | 0 | 0 | 0 | 0 | 0 |
| | | 0 | 0 | 0 | 0 | 0 | 0 | 0 | 0 | 0 | 0 | 0 | 0 | 1.6 | 1.5 | 0 | 0 | 0 |
| | | 0 | 2.1 | 0 | 0 | 1.9 | 1.9 | 0 | 0 | 0 | 0 | 0 | 0 | 0 | 0 | 0 | 0 | 0 |
| | | 0 | 1.6 | 0 | 0 | 0 | 0 | 0 | 0 | 0 | 0 | 2.1 | 0 | 0 | 0 | 0 | 0 | 0 |
| | | 0 | 0 | 0 | 0 | 0 | 0 | 0 | 0 | 0 | 0 | 0 | 0 | 0 | 0 | 1.7 | 0 | 0 |
| | | 3.3 | 0 | 2.2 | 2.3 | 2.0 | 3.0 | 2.1 | 2.8 | 0 | 0 | 0 | 0 | 0 | 3.6 | 4.0 | 1.9 | 0 |

FIG. 6B

| | p34 | p35 | p36 | p37 | p38 | p39 | p40 | p41 | p42 | p43 | p44 | p45 | p46 | p47 | p48 | p49 | p50 |
|---|---|---|---|---|---|---|---|---|---|---|---|---|---|---|---|---|---|
| Group A controls | 0 | 0 | 0 | 0 | 0 | 0 | 0 | 0 | 0 | 0 | 0 | 0 | 0 | 0 | 0 | 0 | 0 |
| | 1.8 | 0 | 1.8 | 1.5 | 1.8 | 1.5 | 1.4 | 2.1 | 2.1 | 1.8 | 2.1 | 2.1 | 1.9 | 1.7 | 1.9 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 3.0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0.7 | 9.6 | 0 | 0 | 0 | 0 | 1.6 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 10.2 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 5.2 | 0 | 0 | 0 | 0 | 0 | 0 | 0 | 0 | 0 | 0 | 0 | 0 |
| | 0 | 1.5 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| Group B asymptomatic | 0 | 0 | 0 | 0 | 0 | 8.2 | 0 | 0 | 0 | 0 | 0 | 0 | 0 | 0 | 7.9 | 0 | 8.8 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 2.0 | 2.1 | 1.9 | 0 | 0 | 0 | 2.3 | 2.2 | 2.0 | 2.2 | 2.4 | 1.9 | 2.0 | 1.7 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 4.8 | 0 | 0 | 0 | 0 | 0 | 0 | 0 | 0 | 0 | 0 | 0 | 3.0 |
| | 0 | 0 | 0 | 0 | 0 | 0 | 0 | 0 | 0 | 0 | 0 | 0 | 2.2 | 0 | 0 | 0 | 0 |
| | 0 | 0 | 0 | 0 | 2.7 | 0 | 0 | 0 | 0 | 0 | 0 | 1.8 | 3.2 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 2.9 | 2.1 | 0 | 0 | 0 | 0 | 0 | 0 | 0 | 0 | 1.9 | 2.6 | 0 | 2.1 |
| | 0 | 0 | 0 | 0 | 0 | 0 | 0 | 0 | 0 | 0 | 0 | 0 | 0 | 0 | 0 | 0 | 0 |
| | 0 | 1.7 | 0 | 0 | 0 | 0 | 0 | 0 | 0 | 0 | 0 | 0 | 0 | 0 | 0 | 0 | 0 |
| | 0 | 0 | 0 | 0 | 1.5 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 2.7 | 0 | 0 | 3.2 | 2.1 | 2.3 | 1.9 | 2.5 | 2.2 | 0 | 1.9 | 0 | 0 |
| | 0 | 0 | 0 | 4.0 | 5.8 | 0 | 0 | 2.9 | 1.9 | 2.1 | 2.2 | 2.7 | 2.3 | 2.3 | 4.3 | 1.9 | 4.4 |
| | 1.6 | 1.7 | 1.7 | 0 | 0 | 0 | 0 | 0 | 1.6 | 1.6 | 1.7 | 3.2 | 7.0 | 1.6 | 0 | 0 | 0 |
| | 0 | 0 | 0 | 0 | 0 | 0 | 0 | 0 | 0 | 0 | 0 | 0 | 0 | 0 | 0 | 0 | 1.4 |
| | 0 | 0 | 0 | 0 | 0 | 0 | 0 | 0 | 0 | 0 | 0 | 0 | 0 | 0 | 0 | 0 | 0 |
| | 0 | 0 | 2.2 | 0 | 0 | 0 | 0 | 0 | 0 | 0 | 0 | 0 | 1.4 | 0 | 0 | 0 | 0 |
| | 0 | 0 | 0 | 0 | 0 | 0 | 0 | 0 | 0 | 0 | 0.5 | 0 | 0 | 1.5 | 3.8 | 0 | 4.3 |
| | 0 | 0 | 2.0 | 0 | 0 | 0 | 1.7 | 2.2 | 2.0 | 1.9 | 2.2 | 2.8 | 1.9 | 1.8 | 1.5 | 0 | 1.6 |
| | 0 | 0 | 0.7 | 0 | 0 | 0 | 1.4 | 0 | 0 | 0 | 0 | 0 | 0 | 0 | 0 | 0 | 0 |
| | 0 | 0 | 0 | 0 | 1.9 | 1.7 | 1.4 | 0 | 1.7 | 0 | 0 | 0 | 1.6 | 2.2 | 0 | 2.6 |
| | 0 | 0 | 0 | 0 | 0 | 0 | 0 | 0 | 0 | 0 | 1.4 | 1.6 | 0 | 0 | 0 | 0 |
| | 0 | 0 | 0 | 2.6 | 3.2 | 0 | 0 | 1.9 | 0 | 0 | 0 | 0 | 0 | 0 | 0 | 0 |
| Group C symptomatic | 0 | 1.5 | 0 | 1.6 | 0 | 1.5 | 0 | 1.4 | 0 | 0 | 0 | 0 | 1.6 | 0 | 1.5 | 0 | 0 |
| | 0 | 0 | 0 | 0 | 0 | 0 | 0 | 0 | 0 | 0 | 0 | 0 | 0 | 0 | 0 | 0 | 0 |
| | 0 | 0 | 0 | 5.5 | 7.8 | 0 | 0 | 0 | 0 | 0 | 0 | 0 | 0 | 0 | 2.0 | 0 | 2.0 |
| | 0 | 0 | 0 | 0 | 0 | 2.9 | 0 | 0 | 0 | 0 | 0 | 0 | 4.1 | 0 | 0 | 0 | 0 |
| | 0 | 0 | 0 | 0 | 0 | 0 | 0 | 0 | 0 | 1.7 | 0 | 1.6 | 1.6 | 0 | 0 | 0 | 0 |
| | 0 | 0 | 0 | 0 | 0 | 0 | 0 | 1.6 | 0 | 0 | 0 | 0 | 0 | 0 | 0 | 0 | 0 |
| | 0 | 0 | 0 | 0 | 0 | 0 | 0 | 1.7 | 1.8 | 1.6 | 1.6 | 1.7 | 1.7 | 1.7 | 1.5 | 1.4 | 0 |
| | 0 | 0 | 0 | 0 | 0 | 0 | 0 | 0 | 0 | 0 | 0 | 0 | 0 | 0 | 3.9 | 0 | 3.2 |
| | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 1.9 | 0 | 0 | 0 | 0 |
| | 0 | 0 | 0 | 18.5 | 18.6 | 2.9 | 0 | 0 | 0 | 0 | 0 | 0 | 5.0 | 14.9 | 0 | 11.3 |
| | 1.8 | 0 | 0 | 3.4 | 4.2 | 0 | 1.7 | 1.6 | 1.6 | 1.6 | 1.7 | 1.7 | 1.6 | 1.8 | 3.2 | 0 | 2.2 |
| | 0 | 0 | 0 | 5.1 | 6.3 | 0 | 0 | 0 | 0 | 0 | 0 | 3.7 | 0 | 0 | 0 | 0 | 0 |
| | 0 | 0 | 0 | 31.0 | 34.4 | 0 | 0 | 0 | 0 | 0 | 0 | 0 | 3.2 | 11.9 | 0 | 8.0 |
| | 0 | 0 | 1.4 | 1.6 | 0 | 0 | 1.9 | 2.0 | 1.6 | 2.0 | 2.1 | 2.0 | 1.8 | 1.9 | 0 | 0 |
| | 0 | 0 | 0 | 0 | 0 | 0 | 1.5 | 0 | 0 | 1.5 | 1.6 | 1.7 | 0 | 0 | 0 | 0 | 0 |
| | 0 | 0 | 0 | 0 | 0 | 0 | 0 | 2.3 | 0 | 0 | 0 | 0 | 3.7 | 0 | 0 | 0 | 0 |
| | 0 | 0 | 0 | 0 | 0 | 0 | 0 | 0 | 0 | 0 | 0 | 0 | 0 | 0 | 2.3 | 0 | 0 |
| | 0 | 0 | 0 | 0 | 0 | 0 | 0 | 0 | 0 | 0 | 0 | 1.8 | 1.7 | 2.6 | 0 | 0 | 0 |
| | 0 | 0 | 2.1 | 3.7 | 4.1 | 0 | 0 | 0 | 1.9 | 0 | 0 | 2.3 | 2.0 | 0 | 3.3 | 0 | 3.5 |

FIG. 6C

COXIELLA BURNETII EPITOPES FOR T CELL-TARGETED Q FEVER VACCINES

CLAIM OF PRIORITY

This application is a § 371 National Stage Application of PCT/US2019/023878, filed Mar. 25, 2019, which claims the benefit of U.S. Provisional Application Ser. No. 62/647,156, filed on Mar. 23, 2018. The entire contents of the foregoing are incorporated herein by reference.

FEDERALLY SPONSORED RESEARCH OR DEVELOPMENT

This invention was made with Government support under Contract No. HDTRA1-15-C-0020 awarded by the Department of Defense. The Government has certain rights in the invention.

SEQUENCE LISTING

This document includes a sequence listing submitted to the United States Patent and Trademark Office via the electronic filing system as an ASCII text file. The sequence listing, which is incorporated by reference herein, is titled 29539_0389US1_SL.txt", was created on Sep. 17, 2020, and has a size of 32 kilobytes.

TECHNICAL FIELD

Described herein are compositions and methods for inducing a protective immune response against *Coxiella burnetii*, to reduce a subject's risk of developing Q fever.

BACKGROUND

Q fever is a zoonotic disease that is transmitted to humans predominantly by aerosol from infected ruminants such as goats, sheep and cattle and has a global public health impact (1). Its causative agent, the small Gram-negative coccobacillus *Coxiella burnetii*, infects a wide range of vertebrate and invertebrate hosts, is very stable in the environment and highly contagious; it is estimated that a single inhaled organism can result in infection (2). As a result, *C. burnetii* is also considered to be a potential biothreat agent (3). Q fever is endemic in many countries worldwide, with outbreaks occurring mainly in occupational settings, including the livestock industry and deployed military personnel (1). The largest reported outbreak occurred in the Netherlands from 2007-2010 with an estimated 40,000 infections at the center of the epidemic area alone (4). Infection remains asymptomatic in an estimated 50-60% of individuals (1). Acute *C. burnetii* infection, when identified clinically and serologically, can be treated with antibiotics such as doxycycline. However, long-term complications of infection are common: 10-20% of patients with acute Q fever later develop Q fever fatigue syndrome, and 1-5% of (often asymptomatically) infected individuals progress to persistent infection known as chronic Q fever, manifesting as endocarditis, aneurysms or vascular infections in individuals with specific risk factors (1, 5). Therefore, a preventive Q fever vaccine is considered critical in occupational and biodefense settings (6).

SUMMARY

*Coxiella burnetii*, the causative agent of Q fever, is a Gram-negative intracellular bacterium transmitted via aerosol. Regulatory approval of the Australian whole-cell vaccine Q-VAX® in the US and Europe has been hindered by reactogenicity in previously exposed individuals. The work described herein identified and rationally selected *C. burnetii* epitopes for a safe, effective and less reactogenic T-cell targeted human Q fever vaccine. Immunoinformatic methods were used to predict 65 HLA class I epitopes and 50 promiscuous HLA class II *C. burnetii* epitope clusters, which are conserved across strains of *C. burnetii*. HLA binding assays confirmed 89% of class I and 75% of class II predictions, and 11 HLA class II epitopes elicited IFNγ responses following heterologous DNA/DNA/peptide/peptide prime-boost immunizations of HLA-DR3 transgenic mice. Human immune responses to the predicted epitopes were characterized in individuals naturally exposed to *C. burnetii* during the 2007-2010 Dutch Q fever outbreak. Subjects were divided into three groups: controls with no immunological evidence of previous infection and individuals with responses to heat-killed *C. burnetii* in a whole blood IFNγ release assay (IGRA) who remained asymptomatic or who experienced clinical Q-fever during the outbreak. Recall responses to *C. burnetii* epitopes were assessed by cultured IFNγ ELISpot. While HLA class I epitope responses were sparse in this cohort, we identified 21 HLA class II epitopes that recalled T-cell IFNγ responses in 10-28% of IGRA+ subjects. IGRA+ individuals with past asymptomatic and symptomatic *C. burnetii* infection showed a comparable response pattern and cumulative peptide response which correlated with IGRA responses. None of the peptides elicited reactogenicity in a *C. burnetii* exposure-primed guinea pig model. These data demonstrate that a substantial proportion of the immunoinformatically identified HLA class II epitopes described herein showed long-lived immunoreactivity in naturally infected individuals, and so can be used for a multi-epitope Q fever vaccine, e.g., for use in humans to reduce risk of developing Q fever.

Thus, provided herein are compositions comprising:
(i) a plurality of epitope peptides from *Coxiella burnetii* source antigens, preferably a polypeptide concatemer comprising a plurality of the peptides optionally with linkers therebetween, and/or
(ii) one or more nucleic acids encoding a plurality of epitope peptides from *C. burnetii* source antigens, preferably encoding a polypeptide comprising a plurality of the peptides optionally with linkers therebetween, and
a pharmaceutically acceptable carrier, wherein the *C. burnetii* source antigens are selected from the group consisting of rplL; com1; atpA; groL; mip; atpA; GtrA family protein: protoporphyrinogen oxidase: gcvT: short chain dehydrogenase: repressor protein C2; sucB: OmpA-like transmembrane domain protein: fabF; membrane-spanning protein Q83CA7; yajC; phospholipase D: membrane-associated protein Q83D52: tig: membrane-associated protein Q83DK8: ompH: lemA; fabF; tag; outer membrane protein Q83EL2: methionine-binding protein Q83F42; and icd.

In some embodiments, the epitope peptides are from one, two, or more source antigens selected from the group consisting of rplL; protoporphyrinogen oxidase; gcvT; short chain dehydrogenase; repressor protein C2; sucB; membrane-spanning protein; yajC: membrane-associated protein; fabF: tag: outer membrane protein; and methionine-binding protein.

In some embodiments, the epitope peptides are from one, two, or more source antigens selected from the group consisting of com1; groL; phospholipase D; and icd.

In some embodiments, the epitope peptides comprise one or more of p4, p12, p14, p15, p17, p18, p20, p21, p22, p26, p27, p30, p37, p38, p42, p43, p45, and p48.

The composition of claim 4, wherein the epitope peptides comprise p4, p12, p14, p15, p17, p18, p20, p21, p22, p26, p27, p30, p37, p38, p42, p43, p45, and p48.

In some embodiments, the epitope peptides further comprise one or more of p2, p6, p19, p23, p31, p46, p47, and p50.

In some embodiments, the epitope peptides comprise p1, p3, p5, p7, p8, p10, p13, p16, p25, p28, p29, p32, p33, p36, p39, p41, p44.

In some embodiments, the composition comprises a nucleic acid encoding a polypeptide comprising a plurality of the epitope peptides, optionally with linkers therebetween. In some embodiments, the nucleic acid is in a viral vector, e.g., an adenoviral vector or a vaccinia viral vector. In some embodiments, the nucleic acid is an RNA transcript.

In some embodiments, the polypeptide is a fusion protein comprising one or more of the epitope peptides fused to a *Mycobacterium tuberculosis* Hsp70 (MtbHSP70).

In some embodiments, the polypeptide is a fusion protein comprising one or more of the epitope peptides fused to a *C. burnetii* source antigen or antigenic fragment thereof, e.g., Com1, i.e., to induce a B cell/antibody response to the source antigen.

In some embodiments, the composition also include an adjuvant, an antibiotic, or both, e.g., as known in the art or described herein.

Further, provided here are methods for reducing risk of Q fever or infection with *C. burnetii* in a subject, the method comprising administering to a subject in need thereof a composition comprising an effective amount of a composition described herein.

Also provided are methods for treating Q fever or infection with *C. burnetii* in a subject, the method comprising administering to a subject in need thereof a composition comprising an effective amount of a composition described herein. In some embodiments, the methods include administering an effecting amount of antibiotic to treat the Q fever or infection.

Additionally, the compositions described herein are provided for use in a method of therapy, e.g., for treating or reducing risk of Q fever or infection with *C. burnetii* infection in a subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Data are shown as the number of individuals recognizing the 50 individual peptides, depending on whether subjects are IGRA− (Group A, no clinical disease, n=21; grey bars) or IGRA+(Group B, asymptomatic; Group C, symptomatic; n=56; black bars). (A) shows peptide responses reaching a SI≥2. Bars extending over dotted lines indicate those peptides that were recognized by more than 10% of IGRA-subjects (>2/21) or IGRA+ subjects (>5/56). (B) shows the stimulation index for each positive response per subject for the 21 highly antigenic peptides identified in (A). Whisker-dot-plots show the interquartile range ($25^{th}$ and $75^{th}$ percentile) with whiskers extending from min to max values. Numbers indicate the median SI per peptide for IGRA+ subjects.

FIGS. 6A-6C. Overview of human IFNγ responses to HLA class H peptides. Individual IFNγ responses to HLA class II peptides determined by cultured ELISpot are depicted as stimulation indices (SI) for all donors from group A (n=21), B (n=33) and C (n=23). Each row shows data from one donor, each column responses to one of the 50 class II peptides (FIG. 6A: p1-p16: FIG. 6B: p17-p33: FIG. 6C: p34-p50). Responses not significantly different from background and/or lower than an average of 10 spots/well are denoted as 0. Crosses indicate conditions for which no data are available due to technical error or insufficient cell numbers.

Figure 7A:
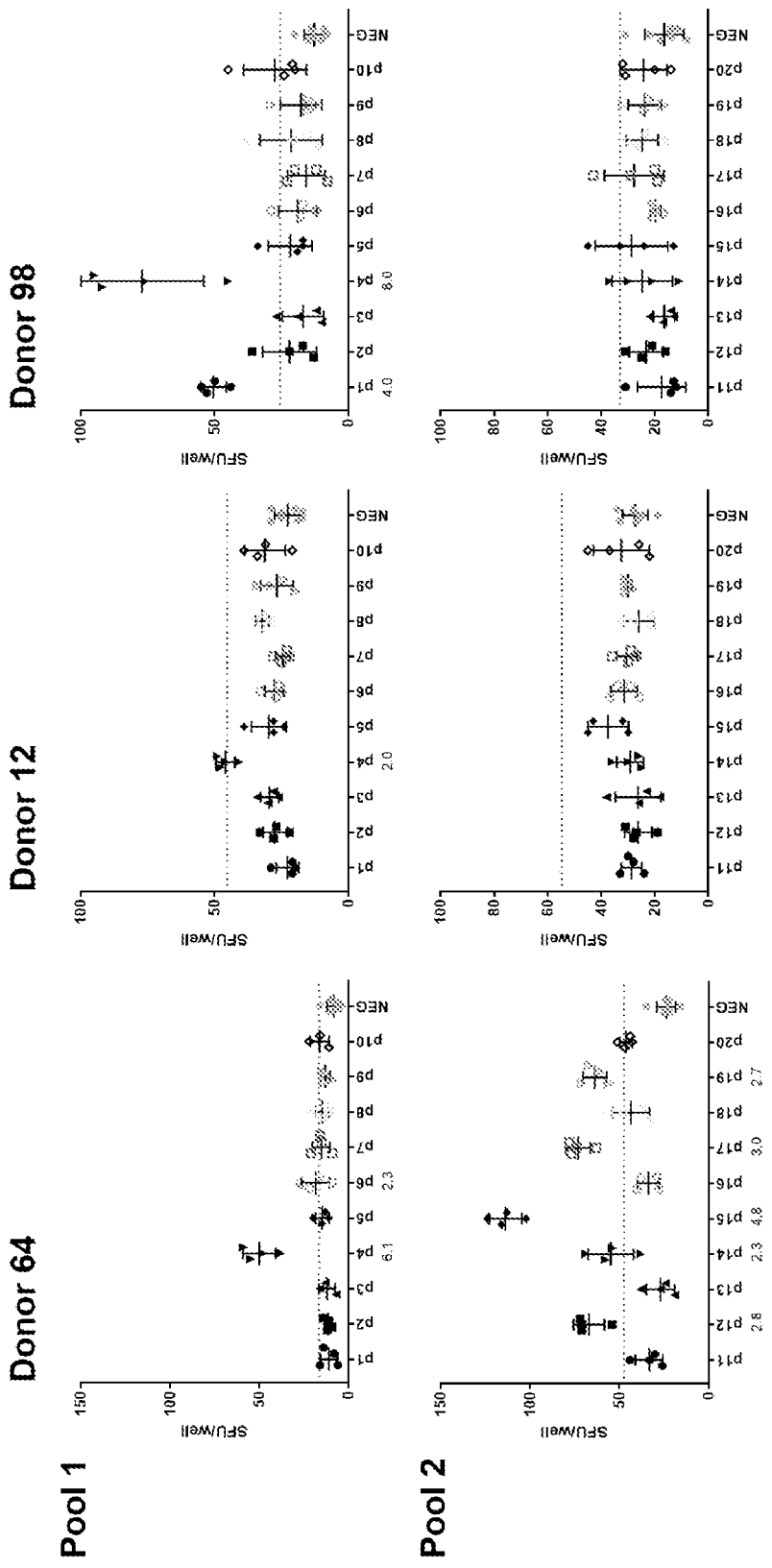
Figure 7B:
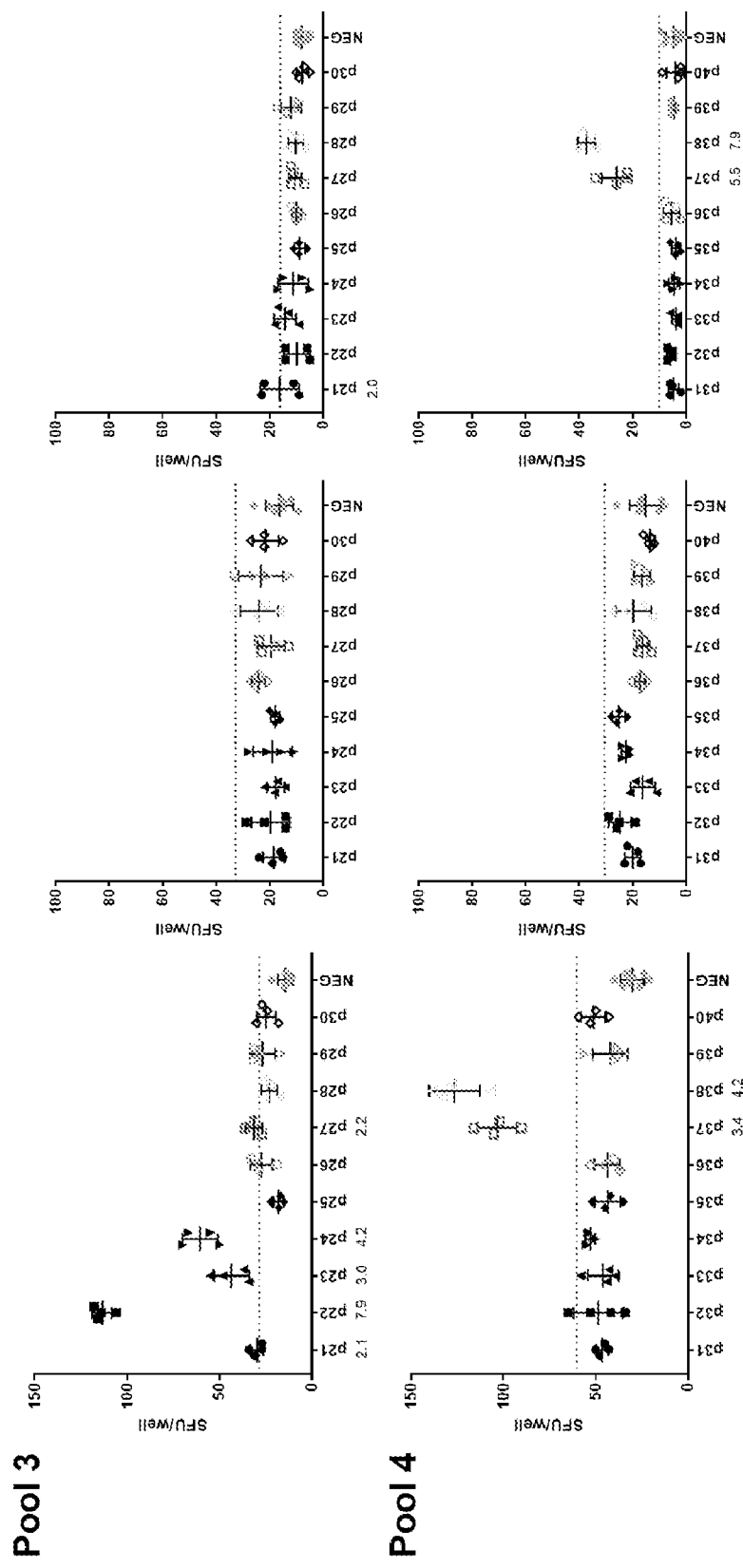
Figure 7C:
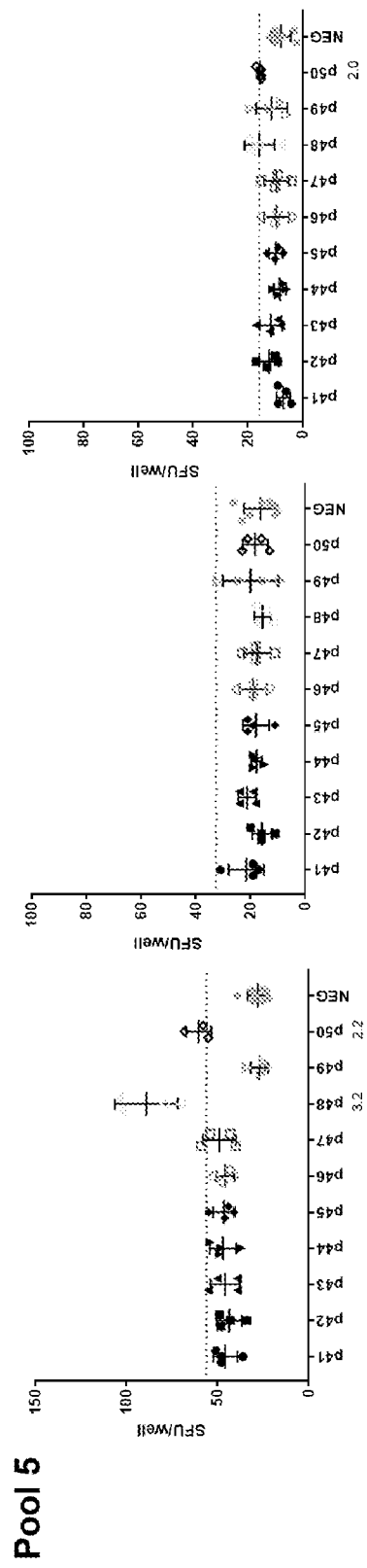

FIGS. 7A-7C. Representative human IFNγ cultured ELISpot responses to HLA class II peptides. HLA class II peptide specific IFNγ responses are shown as absolute spot forming units (SFU) per well for three individual donors. Data are shown per peptide pool expansion culture (FIG. 7A: Pool 1, Pool 2: FIG. 7B: Pool 3, Pool 4; FIG. 7C: Pool 5). Dotted lines indicate the cut-off for positivity, namely a stimulation index (SI) of 2 in reference to medium-only wells (negative control, NEG) per expansion culture, or 10 SFU/well if SI=2 would otherwise be reached at a lower spot count. Positive responses further needed to be significantly higher than NEG wells by one-way ANOVA with Holm-Sidák multiple comparisons post-hoc test. SI values for positive responses are denoted underneath the respective peptide label on the x-axis.

FIG. 7. Representative human IFNγ cultured ELISpot responses to HLA class II peptides. HLA class II peptide specific IFNγ responses are shown as absolute spot forming units (SFU) per well for three individual donors. Data are shown per peptide pool expansion culture. Dotted lines indicate the cut-off for positivity, namely a stimulation index (SI) of 2 in reference to medium-only wells (negative control, NEG) per expansion culture, or 10 SFU/well if SI=2 would otherwise be reached at a lower spot count. Positive responses further needed to be significantly higher than NEG wells by one-way ANOVA with Holm-Šidák multiple comparisons post-hoc test. SI values for positive responses are denoted underneath the respective peptide label on the x-axis.

DETAILED DESCRIPTION

The two currently available Q fever vaccine formulations, Q-VAX® for humans (licensed for use in Australia only) and COXEVAC® for ruminant animals such as goats (licensed in the European Union), are inactivated whole cell vaccines based on phase I *C. burnetii*. Although Q-VAX® is strongly protective (7, 8), reported side effects in previously exposed individuals, in particular at the site of injection, necessitate pre-vaccination screening and are a daunting hurdle to regulatory approval in the US and Europe (6, 9). Hence, there is a clear need for a less reactogenic and at least equally efficacious vaccine for occupational and biodefense purposes.

Subunit vaccines have the advantage over traditional whole cell vaccines that they are generally better tolerated and offer the opportunity for rational design, in terms of both the target antigens and the appropriate delivery or adjuvant system selected to elicit the desired immune response (10). While both humoral and cellular immune responses are elicited upon *C. burnetii* infection and administration of whole cell vaccines (11), antibodies alone are insufficient to resolve infection (12, 13). Results from studies in murine infection models suggest that T-cell responses, particularly Th1 responses, are critical for clearance of the bacteria (13-15). The Th1 cytokine IFNγ has been shown to restore phagosome maturation and facilitate intracellular killing of *C. burnetti* (16, 17). Accordingly, a proof of concept study showed that partial protection in C57BL/6 mice can be elicited by a vaccine comprising seven *C. burnetii* CD4 epitopes (18).

The present study identified HLA class I and class II epitopes for inclusion in a non-reactogenic T-cell-targeted vaccine to control *C. burnetii* infection and hence prevent Q fever disease in humans. HLA binding competition assays demonstrated a high accuracy of the immunoinformatic predictions for HLA class I and class II recognition, and a murine immunogenicity study demonstrated that half of the peptides both predicted and shown to bind HLA-DR3 were also capable of eliciting de novo responses in tgHL-A-DR3 mice. Notably, while responses to the 65 selected HLA class I epitopes were barely detectable in PBMCs from individuals naturally exposed to *C. burnetii* during the Dutch Q fever outbreak 7-10 years prior to this study, 21 out of the 50 predicted HLA class II epitope clusters recalled responses in 10-28% of those individuals that also showed an ex vivo response to whole heat-killed *C. burnetii*. This demonstrated for the first time that natural exposure of humans to *C. burnetii* induces long-lived responses to immunodominant, promiscuous, and conserved HLA class II T-cell epitope clusters. These peptide sequences can be included in a vaccine aiming to elicit sustained T-cell memory in a broad and immunogenetically diverse human population that can be boosted and recalled by natural exposure.

These long-lived epitope-specific T-cell responses are consistent with previous studies in Q fever convalescent individuals and recipients of the whole cell formalin-inactivated phase I vaccine Q-VAX®, which have consistently reported a long-lived T-cell response to whole cell *C. burnetii* antigen. The T-cell response, in this context, develops within 2 weeks post-vaccination (63), is detectable for at least 8-10 years following natural exposure or vaccination (64, 65) and in some studies was found to be considerably more durable than the mounted antibody response (63, 64). However, studies investigating the specific antigen targets of the induced immune response in humans have so far solely focused on antibodies (20, 21, 23, 24, 26, 27, 29, 33, 66-72). T-cell antigen targets have only been assessed in a limited number of murine studies (18, 21, 22, 73), including one study that investigated T-cell responses to recombinant *C. burnetii* proteins by ELISpot in HLA-DR4 transgenic mice (21). T-cell antigen targets of murine CD4 T-cells in these studies were all chosen based on antigen recognition by human sera of Q-fever exposed individuals (18, 21, 22). While this B-cell antigen-guided screening approach for T-cell targets precludes identification of T-cell epitopes for source antigens that do not elicit a dominant antibody response, it has the advantage of significantly reducing and focusing the number of antigens to be evaluated. In the present study, 44/50 HLA class II peptides (88%) from 27/29 selected sero-reactive source antigens (93%) elicited T-cell recall responses from at least one donor with a history of *C. burnetii* exposure during the Dutch Q fever outbreak. This large hit rate for HLA class II epitope clusters illustrated the feasibility of this approach to focus on sero-reactive antigens for T-cell epitope prediction.

One challenge when focusing a vaccine on individual epitopes is to choose epitopes that are capable of eliciting responses from a large part of the human population. Despite the expected HLA diversity in this human cohort, 21/50 (42%) of the screened HLA class II peptides, representing 16/29 source antigens, were recognized by more than 10% of the subjects exposed 7-10 years prior. In comparison, IFNγ recall responses to H2 I-Ab-restricted *C. burnetii* epitopes were only detectable for 17-26% and 5.3-6.8% of the predicted epitopes in inbred C57BL/6 mice immediately following immunization with the selected source antigens or whole cell antigen, respectively (18, 22). Of note, all but one of the antigens in the murine CD4 epitope vaccine study (18) were also amongst the HLA class II source antigens in the present study, and one of the seven vaccine epitope sequences (OmpA146-160), covered by p45 in our peptide screening library, was one of highly antigenic peptides recognized by 7/56 (12.5%) of IGRA+ subjects. These results validate the ability of the immunoinformatic algorithms employed to predict promiscuous HLA class II epitopes for humans. Moreover, the highly antigenic HLA class II epitopes identified herein are not only promiscuous across HLA-DR supertypes (76% predicted binding to 6 or more alleles) but are also conserved across all *C. burnetii* genomes publicly available in 2015, as well as in the Dutch outbreak strain (39). Such conserved immunodominant T-cell epitopes have also been found for *Mycobacterium tuberculosis* (74-76), hepatitis C virus (77, 78), and HIV (79, 80) and are interesting vaccine targets, since they are likely under positive selection pressure and hence unlikely to be subject to vaccine-induced immune evasion (74).

A somewhat unexpected finding of the present study was the scarcity of detectable responses to the predicted HLA class I epitopes in human subjects. Earlier studies indicated that human CD8 T-cells contribute to *C. burnetii*-specific IFNγ production (81), and in murine models CD8 T-cells appear to be more critical than CD4 T-cells for resolving infection (15, 82). Using a similar approach to the present study, a recent report identified 29 class I epitopes from T4SS substrates that conferred partial protection in a murine vaccine-challenge study (73). One of these 29 was amongst the few HLA class I epitopes recognized by two human donors (p92 from the tol-pal system protein YbgF). The proportion of peptides recognized at least once in the human cohort (15/65, 23%) was comparable to the recognition frequency observed in the murine study (29/157, 18%), suggesting that human HLA class I epitopes were predicted effectively in the present study.

The much smaller frequency of HLA class I compared to HLA class II responses could be due to a number of reasons. Firstly, while HLA class II peptides are promiscuous epitope clusters each containing 5-20 9-mers with various HLA-DR binding motifs. HLA class I epitopes do not display this promiscuity. Each of the 65 HLA class I peptides have, on average, 0.4 binding motifs across the class I supertype alleles modeled by EpiMatrix and represented in over 95% of the global human population. This is in stark contrast to 1.36 binding motifs found, on average, for the 50 HLA class II peptides across class II supertype alleles, representing a 3.4-fold increase over the number of motifs for the HLA class I peptides. The larger number of binding opportunities for HLA class II peptides may thus contribute to the greater number of responses they recalled.

Secondly, reports have shown that the TCR repertoire of CD4 T-cells is estimated to be about five times greater than the TCR repertoire of CD8 T-cells (83), suggesting that there are more opportunities for CD4 T-cell reactivity. Finally, it is also possible that circulating *C. burnetii*-specific CD8 T-cells are less well detected than CD4 T-cells at such a late time point (7-10 years) post-exposure, which would not be unprecedented: following smallpox infection or vaccination, antigen-specific CD8 T-cells show a much faster contraction to undetectable levels than do CD4 T-cells (84, 85). Similarly, a significant contraction in *Mycobacterium tuberculosis*-specific CD8 but not CD4 effector memory responses was reported (86) as well as a significant decrease in total and antigen-specific central memory CD8 T-cells (87). Of note, *C. burnetii* epitope-specific murine CD8 T-cell responses were assessed only ten days post-infection (73), and challenge experiments were carried out no later than 28 days following vaccination or transfer of infection-induced CD8 T-cells (15, 73).

The present study further compared epitope-specific responses between *C. burnetii* exposed individuals with or without a history of an acute clinical episode of Q fever. Although responses tended to be more frequent in past symptomatic donors and some peptides were recognized only by either past symptomatic or asymptomatic individuals, these observations are based on a relatively small number of responding subjects. Moreover, none of the observed differences were striking enough to suggest a significant difference in the quality of the induced T-cell response between these two groups that would explain why some individuals developed symptoms and others did not.

The ultimate aim of the Q-VaxCelerate consortium is to develop a non-reactogenic Q-fever vaccine that could be administered without screening for pre-exposure, especially in an outbreak setting or when occupational hazard warrants immediate broad-scale vaccination. Since none of the peptides as such elicited a reactogenic response in the guinea pig model, no peptides were eliminated from further consideration by this screen. To minimize chances for reactogenicity of the epitope vaccine in its final formulation, one delivery strategy would be to use adenoviral vectors delivered intramuscularly. In this way one could avoid the use of adjuvants that cause localized inflammation at the injection site; such vectors have had a good safety profile in human clinical trials and have been shown to induce potent CD4 and CD8 T-cell responses (92-94).

In conclusion, we herein identify for the first time a set of *C. burnetii*-specific HLA class II T-cell epitope clusters that was computationally predicted and shown to bind a broad range of HLA-DR types, elicit immunogenicity in tgHLA-DR3 mice and recalled long-lived memory responses in naturally exposed individuals. These peptides can be used in a promiscuous multi-epitope-based Q fever vaccine for use in mammals, e.g., in humans.

Vaccine Compositions

Described herein are compositions comprising peptides comprising *C. burnetii*-specific HLA class II T-cell epitopes that can be used in vaccine compositions. As used herein, a vaccine composition is one that elicits a protective immune response to the peptides, resulting in a reduction in risk of later infection with *C. burnetti*, and/or a reduction in severity of a later infection.

Peptides and Nucleic Acids

The vaccine compositions described herein can comprise a plurality of epitope peptides as described herein. In some embodiments, the epitope peptides are derived from one, two, three, or more different source antigens, e.g., as shown in Table 2, e.g., rplL: com1; atpA; groL; mip; atpA; GtrA family protein; protoporphyrinogen oxidase; gcvT; short chain dehydrogenase; repressor protein C2; sucB; OmpA-like transmembrane domain protein: fabF; membrane-spanning protein Q83CA7; yajC; phospholipase); membrane-associated protein Q831D52; tig; membrane-associated protein Q83DK8: ompH; lemA; fabF; tag; outer membrane protein Q83EL2; methionine-binding protein Q83F42; and icd. For example, the epitope peptides can be from one, two, or more source antigens selected from the group consisting of rplL; protoporphyrinogen oxidase; gcvT; short chain dehydrogenase; repressor protein C2; sucB: membrane-spanning protein: yajC: membrane-associated protein; fabF; tag; outer membrane protein; and methionine-binding protein. Additionally, the epitope peptides can include sequences from one, two, or more source antigens selected from the group consisting of com1; groL; phospholipase D; and icd. As used herein, a peptide sequence "derived from" a source antigen means that the sequence of the peptide is a fragment of the source, i.e., consecutive amino acids that have the same sequence as a part of the source antigen. Candidate epitope peptide sequences can be identified and tested using bioinformatics and other methods, e.g., as described herein and known in the art.

In some embodiments, the epitope peptides comprise at least 2, 4, 6, 8, 10, 12, 14, 16, 18, 20, 22, 24, 26, 27, 28, 30, 32, 34, 36, 38, 40, 42, 44, 46, 48, 49 or all 50 of the peptides listed in Table 2. In some embodiments, the compositions comprise peptides comprising one or more of, e.g., all of, p4, p12, p14, p15, p17, p18, p20, p21, p22, p26, p27, p30, p37, p38, p42, p43, p45, and/or p48. The epitope peptides can further comprise one or more of p2, p6, p19, p23, p31, p46, p47, and/or p50; and further one or more of p1, p3, p5, p7, p8, p10, p13, p16, p25, p28, p29, p32, p33, p36, p39, p41, and/or p44. In general, the peptide sequences are each at least 12, 13, 14, 15, or 16 amino acids long, up to 20, 21, 22, 23, 24, 25, 26, 27, 28, 29, or 30 amino acids long, e.g., are 12-30, e.g., 15-25, 15-20, amino acids long, e.g., they comprise 12-30, e.g., 15-25, 15-20, or 15-19, consecutive amino acids from a sequence of a source antigen as shown in Table 2.

The following table illustrates exemplary peptide categories: the compositions and methods can include one or more of these categories.

| Category | Peptides |
| --- | --- |
| Mouse immunoreactive peptides | p15, p18, p20, p21, p26, p27, p30, p37, p38, p42, p43, p45 |
| Human immunoreactive peptides in: at least 20% of IGRA + donors (SI cutoff of 2), and at least 10% of IGRA + donors (SI cutoff of 3) | p04, p12, p14, p17, p22, p38, p48 |
| Human immunoreactive peptides in: at least 10% of IGRA + donors (SI cutoff of 2) | p02, p06, p19, p23, p24, p31,, p46, p47,, p50 |
| Human immunoreactive peptides in: at least one IGRA + donor | p01, p03, p05, p07, p08, p10, p13, p16, p25, p28, p29, p32, p33, p36, p39, p41, p44 |

The peptides can optionally be provided as fusion proteins with other antigenic proteins. For example, Com1 fusion proteins can be used to optionally induce a humoral/antibody response, as Com1 is a bacterial membrane protein, and is not expected to be functional when expressed in eukaryotic cells. The epitope peptide concatemer sequences do not encode full length proteins, but are expected to induce T cell responses, and thus could be used to generate a combination vaccine targeting both T cells and B cells. In addition to com1, other *C. burnetii* antigens can be used, e.g., and of the source antigens described in Table 2.

*Mycobacterium tuberculosis* Hsp70 (MtbHSP70)-containing fusion proteins can also be used; see. e.g., Tobian et al. J Immunol May 1, 2005, 174 (9) 5209-5214; Brauns et al., Expert Rev. Vaccines Early online, 1-12 (2014). An exemplary sequence of MtbHSP70 is provided below. The HSP70 protein is expected to have immune-modulating activity with the potential to enhance immune responses to the epitopes in the fused concatemer (Brauns et al., 2015, Expert Rev Vaccines 14: 435; Leblanc et al., 2014, Human Vaccines & Immunotherapeutics 10: 3022). Heatshock proteins, including HSP70, have been used clinically as vaccines and immunotherapies for the treatment of cancer (Shetsov and Multhoff, 2016, Front Immunol 7:171). In some embodiments, the HSP70 peptide-binding pocket can be mutated to prevent the binding of endogenous peptides in order to minimize the potential of stimulating autoimmune reactions.

MtbHsp70-625aa, heat shock protein 70 [*Mycobacterium tuberculosis*]. V>F mutation in bold (SEQ ID NO: 51)
MARAVGIDLGTTNSVVSVLEGGDPVVVANSEGSRTTPSIVAFARNGEVL

VGQPAKNQAVTNVDRTVRSVKRHMGSDWSIEIDGKKYTAPEISARILMK

LKRDAEAYLGEDITDAVITTPAYFNDAQRQATKDAGQIAGLNVLRIVNE

PTAAALAYGLDKGEKEQRILVFDLGGGTFDVSLLEIGEGVVEVRATSGD

-continued

NHLGGDDWDQRVVDWLVDKFKGTSGIDLTKDKMAMQRLREAAEKAKIEL

SSSQSTSINLPYITVDADKNPLFLDEQLTRAEFQRITQDLLDRTRKPFQ

SVIADTGISVSEIDHVVLVGGSTRMPAVTDLVKELTGGKEPNKGVNPDE

VVAVGAALQAGVLKGEVKDVLLLDVTPLSLGIETKGGFMTRLIERNTTI

PTKRSETFTTADDNQPSVQIQVYQGEREIAAHNKLLGSFELTGIPPAPR

GIPQIEVTFDIDANGIVHVTAKDKGTGKENTIRIQEGSGLSKEDIDRMI

KDAEAHAEEDRKRREEADVRNQAETLVYQTEKFVKEQREAEGGSKVPED

TLNKVDAAVAEAKAALGGSDISAIKSAMEKLGQESQALGQAIYEAAQAA

SQATGAAHPGGEPGGAHPGSADDVVDAEVVDDGREAK

In some embodiments, a peptide sequence used is at least 80%, 85%, 90%, 95%, 97%, 98%, or 99% identical to a peptide sequence provided herein. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

In some embodiments, the peptide include one, two, three, four, or five differences from a sequence provided herein.

In some embodiments, the compositions can comprise RNA or DNA sequences encoding the epitope peptides and/or fusion proteins. For example, the compositions can comprise one or more RNA or DNA molecules, wherein each RNA or DNA molecule encodes one or more peptides as described herein; wherein one RNA or DNA molecule encodes a plurality of peptides, peptide linkers are preferably included therebetween. The peptide linkers can be any sequence of 2-20 amino acids, preferably 2-8 or 2-4 amino acids, that provide a break between the peptides, e.g., Gly-Pro-Gly-Pro-Gly (SEQ ID NO:52), Gly-Gly-Gly-Ser (SEQ ID NO:53), or Gly-Ser-Gly-Ser (SEQ ID NO:54)

spacer sequences, or linkers that include cleavage sequences, e.g., RVKR (SEQ ID NO:55) to introduce a furin cleavage site-see Leblanc et al 2014 (FIG. 1) and Chen et al., Adv Drug Deliv Rev. 2013 Oct. 15; 65(10): 1357-1369, to remove junctional epitopes.

In some embodiments the sequences are codon-optimized for expression in the target organism, e.g., a human. Codon-optimized human nucleotide sequences are disclosed herein. These codon-optimized human nucleotide sequences were generated by substituting codons in the naturally occurring nucleotide sequence that occur at lower frequency in human cells for codons that occur at higher frequency in human cells. The frequency of occurrence for codons can be computationally determined by methods known in the art.

Viral Delivery

The compositions described herein can be delivered in a manner compatible with the nature of the composition to raise an immune response. For example, a DNA vaccine comprising a plurality of epitope peptides as described herein can be delivered using a viral vector. Viral vectors for use in the present methods and compositions can include recombinant retroviruses, adenovirus, adeno-associated virus, vaccinia virus, and lentivirus. Preferably the virus is non-replicating.

A viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986). In preferred embodiments, the viral vector is a chimpanzee adenovirus, e.g., ChAdOx1. See, e.g., Green et al., Sci Transl Med. 7(300): 300ra126 (2015); and Coughlan et al., EBioMedicine 29 (2018) 146-154.

Another viral vector system useful for delivery of nucleic acids in the present methods is the adeno-associated virus (AAV). AAV is a tiny non-enveloped virus having a 25 nm capsid. No disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Vectors containing as little as 300 base pairs of AAV can be packaged and can integrate. Space for exogenous DNA is limited to about 4.7 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985): Wondisford et al., Mol. Endocrinol. 2:32-39 (1988); Tratschin et al., J. Virol. 51:611-619 (1984); and Flotte et al., J. Biol. Chem. 268:3781-3790 (1993), here are numerous alternative AAV variants (over 100 have been cloned), and AAV variants have been identified based on desirable characteristics. For example, AAV9 has been shown to efficiently cross the blood-brain barrier. Moreover, the AAV capsid can be genetically engineered to increase transduction efficient and selectivity, e.g., biotinylated AAV vectors, directed molecular evolution, self-complementary AAV genomes and so on. In some embodiments, AAV1 is used.

Alternatively, retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*. Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895: Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Methods of Use

The methods described herein can be used in subjects who are at risk of developing Q fever, e.g., subjects who live in or near, or are visiting a region where they might be exposed to risk of getting Q fever. In some embodiments, the compositions are administered once, or once a year, or once every two years, five years, ten years, or twenty years or more. In some embodiments, a first dose (e.g., a prime dose) and a second dose (a boost dose) are administered. In some embodiments, a heterologous prime-boost administration regime is used, e.g., wherein an adenoviral vector is used for the first (prime) dose, and a vaccinia virus is used as a a second (boost) dose. See, e.g., Lu et al., Curr Opin Immunol. 2009 June; 21(3): 346-351; Coughlan et al., EBioMedicine 29 (2018) 146-154.

In general, the present methods and compositions can be used in any mammalian subject who is susceptible to Q fever, e.g., human subjects or ruminants, e.g., goats, sheep, and cattle. For ruminants, other combinations of epitope peptides can be used.

Pharmaceutical Compostions

The methods described herein include the use of pharmaceutical compositions comprising the peptides as described herein, or nucleic acids encoding the peptides as described herein, as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the so compositions, e.g., adjuvants such as without limitation aluminium salts, alum, aluminium phosphate, aluminium hydroxide, squalene, oils, MF59, and AS03 ("Adjuvant System 03"). The adjuvant can be selected from the group consisting of Cationic liposome-DNA complex JVRS-100, aluminum hydroxide vaccine adjuvant, aluminum phosphate vaccine adjuvant, aluminum potassium sulfate adjuvant, Alhydrogel, ISCOM(s)™, Freund's Complete Adjuvant, Freund's Incomplete Adjuvant, CpG DNA Vaccine Adjuvant, Cholera toxin, Cholera toxin B subunit, Liposomes, Saponin Vaccine Adjuvant, DDA Adjuvant, Squalene-based Adjuvants, Etx B subunit Adjuvant, IL-12 Vaccine Adjuvant, LTK63 Vaccine Mutant Adjuvant, TiterMax Gold Adjuvant, Ribi Vaccine Adjuvant, Montanide ISA 720 Adjuvant, *Corynebacterium*-derived P40 Vaccine Adjuvant, MPL™ Adjuvant, AS04, AS02, Lipopolysaccharide Vaccine Adjuvant, Muramyl Dipeptide Adjuvant, CRL1005, Killed *Corynebacterium parvum* Vaccine Adjuvant, Montanide ISA 51, *Bordetella pertussis* component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Polygen Vaccine Adjuvant, Adjumer™, Algal Glucan, Bay R1005, Theramide®, Stearyl Tyrosine, Specol, Algammulin, Avridine®, Calcium Phosphate Gel, CTA1-DD gene fusion protein, DOC/Alum Complex, Gamma Inulin, Gerbu Adjuvant, GM-CSF, GMDP, Recombinant hIFN-gamma/Interferon-g, Interleukin-1β, Interleukin-2, Interleukin-7, Sclavo peptide, Rehydragel LV, Rehvdragel HPA, Loxoribine, MF59, MTP-PE Liposomes, Murametide, Murapalmitine, D-Murapalmitine, NAGO, Non-Ionic Surfactant Vesicles, PMMA, Protein Cochleates, QS-21, SPT (Antigen Formulation), nanoemulsion vaccine adjuvant, AS03, Quil-A vaccine adjuvant, RC529 vaccine adjuvant, LTR192G Vaccine Adjuvant, *E. coli* heat-labile toxin, LT, amorphous aluminum hydroxy phosphate sulfate adjuvant, Calcium phosphate vaccine adjuvant, Montanide Incomplete Seppic Adjuvant, Imiquimod, Resiquimod, AF03, Flagellin, Poly(I:C). ISCOMATRIX®, Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1. Sendai Proteoliposomes. Sendai-containing Lipid Matrices, Threonyl muramyl dipeptide (TMDP), Ty Particles vaccine adjuvant. Bupivacaine vaccine adjuvant, DL-PGL (Polyester poly (DL-lactide-co-glycolide)) vaccine adjuvant. IL-15 vaccine adjuvant. LTK72 vaccine adjuvant, MPL-SE vaccine adjuvant, non-toxic mutant E112K of Cholera Toxin mCT-E112K, and Matrix-S. Light-based adjuvants, e.g., non-destructive lasers as described in WO2013033496 and Kashigawa et al., J Vaccines Vaccin. 2016 February; 7(1): 307, can also be used. In some embodiments, immunotherapeutic/immunomodulatory drug agents are also included, to modulate and augment the immune response to the vaccine; antibiotics can also be included in the composition, or administered separately, in subjects who are already infected with Q fever. The antibiotics can be, e.g., doxycycline alone in combination with hydroxychloroquine; Co-trimoxazole; quinolones (e.g., ciprofloxacin, ofloxacin or pefloxacin); rifampin; and/or macrolides can also be used. See, e.g., Kersh et al., Expert Rev Anti Infect Ther. 2013 November; 11(11): 1207-1214; Levy et al., Antimicrob Agents Chemother. 1991 March; 35(3):533-7.

Pharmaceutical compositions are typically formulated to be compatible with its intended route of administration. Examples of routes of administration include parenteral, e.g., intradermal, intramuscular, transdermal (topical), transmucosal, and subcutaneous administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminctetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water. Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Systemic administration of a composition as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

For administration by inhalation, the compositions are typically delivered in the form of an aerosol spray from pressured container or dispenser which contains a suitable propellant. e.g., a gas such as carbon dioxide, or a nebulizer. Such methods include those described in U.S. Pat. No. 6,468,798.

Other needle-free methods can also be used, e.g., diffusion patches, liquid jet injectors, microneedle arrays/patches, and biolistic particle delivery, e.g., as described in Kendall et al., Handb Exp Pharmacol. 2010; (197):193-219 and Ravi et al., Int J Pharm Investig. 2015 October-December; 5(4): 192-199.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194, 389, and the mammalian transdermal needle-free vaccination with powder-form vaccine as disclosed in U.S. Pat. No. 6,168,587. Additionally, intranasal delivery is possible, as described in, inter alia. Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

The pharmaceutical compositions can be included in a container, pack, or dispenser together with instructions for administration.

EXAMPLES

The invention is further described in the following examples, which do not limit the scope of the invention described in the claims.

Materials and Methods

The following materials and methods were used in the Examples below.

Ethics Statement

Animal research protocols for studies with HLA-DR3 transgenic mice performed by EpiVax were reviewed and approved by TGA Sciences Incorporated Institutional Animal Care and Use Committee (P07-10R20-EV69, P07-10R20-EV71). Animal research protocols for guinea pig experiments were reviewed and approved by the Colorado State University Institutional Animal Care and Use Committee (14-5305A, 16-6844A). All animal experimental activities were conducted in full compliance with university, federal and international regulations and the standards of the DoD Animal Care and Use Review Office. Methods of euthanasia as described below were consistent with the recommendations of the Panel on Euthanasia of the American Veterinary Medical Association (AVMA).

The human study was carried out in accordance with the recommendations of the Medical Ethical Committee Brabant (Tilburg, Netherlands) with written informed consent from all subjects. All subjects gave written informed consent in accordance with the Declaration of Helsinki. The protocol was reviewed and approved by the Medical Ethical Committee Brabant (Tilburg, Netherlands, NL51305.028.15).

Immunoinformatics

Sequence Collection

*C. burnetii* antigens used in epitope predictions were immune-dominant antigens that were recognized by sera from *C. burnetii*-exposed humans and demonstrated to stimulate $CD4^+$ T-cell and/or antibody responses in mice, as reported in the literature (18, 20-29), and type IV secretion system (T4SS) effectors (21, 23, 30-37). Of 94 T4SS protein sequences retrieved from the UniProt database (38), 53 were selected for immunoinformatic analysis; 20 putative effectors lacking experimental support for secretion, eight hypothetical proteins from pseudogenes and thirteen proteins with discontinued database records were rejected. An additional 40 sequences were retrieved from UniProt for the immune-dominant antigen set. All sequences were retrieved from the reference RSA 493/Nine Mile phase I *C. burnetii* strain. Six additional complete *C. burnetii* genomes available in 2015 were obtained from UniProt for homology analyses: (i) RSA 331/Henzerling II, (ii) CbuK_Q154, (iii) Namibia, (iv) MSU Goat Q177, (v) CbuG_Q212, and (vi) Dugway 5J108-111. Of note, genome sequences were completed for two *C. burnetii* strains associated with the Dutch Q fever outbreak (39) during the course of this work, and all but one of the selected epitopes (p69) were 100% conserved in the two Dutch strains.

Epitope Prediction

Sequences for all antigens from the reference Nine Mile strain were scored for binding potential against a panel of HLA class II and class I alleles using the EpiMatrix algorithm (40). This algorithm as well as the ClustiMer and JanusMatrix algorithms discussed below are part of the proprietary iVAX toolkit developed by EpiVax, which is available for use under license or by collaboration (epivax.com/immunogenicity-screening/iva.x-web-based-vaccine-design). Epitopes which were 100% identical in the corresponding antigens from at least six of the seven genomes (MHC class I epitopes) or all seven genomes (MHC class II epitopes) were prioritized. Class II epitopes were identified for eight supertype HLA-DR alleles: DRB1*0101, DRB1*0301, DRB1*0401, DRB1*0701, DRB1*0801, DRB1*1101, DRB1*1301 and DRB1*1501. For class I epitopes, selections were made based on predictions for six HLA-A and HLA-B supertype alleles: A*0101, A*0201, A*0301, A*2402, B*0702, B*4403. Each set of supertype alleles covers >95% of the human population worldwvide (41, 42). EpiMatrix assigns a score for each peptide/allele pair on a normalized Z-scale. Peptides with Z-Scores ≥1.64 are considered hits and have a significant likelihood of binding to MHC molecules. These sequences represent the top 5% of any randomly generated set of 9-mer peptides (43).

Regions of high class II epitope density per antigen were identified using the ClustiMer algorithm for selection of vaccine candidates with increased breadth of reactivity (40). ClustiMer searches for contiguous segments of 15-30 amino acids with elevated class II HLA binding promiscuity. Epitope density within a cluster is estimated by EpiMatrix Cluster Scores, where scores of 10 and above are considered elevated. Peptide sequences with elevated EpiMatrix Cluster Scores usually contain class II HLA binding motifs to most, if not all, HLA-DR supertype alleles. MHC Class II epitope clusters were further filtered to remove sequences derived from signal sequences and transmembrane domains to avoid peptide synthesis and solubility complications. For class I peptides, epitopes with Z-Scores in the top 1% of a normal distribution (Z-Score ≥2.32) were prioritized. A greater weight was given to the top 1% EpiMatrix scoring peptides per HLA class I supertype that were also predicted to bind to at least one additional HLA class I supertype.

Homology Analysis

To eliminate peptide candidates unlikely to stimulate effector T-cell responses due to potential cross-reactivity with T-cells previously trained on host or commensal antigens, predicted HLA class I and class II *Coxiella* sequences were screened for T-cell receptor-face homology against host and commensal proteins using the JanusMatrix algorithm (44). Databases comprising the UniProt reviewed human proteome (uniprot.org/proteomes/UP000005640) and Human Microbiome Project gut commensal proteomes were used. Epitopes with low human or human microbiome JanusMatrix homology scores were prioritized. The JanusMatrix human homology score cutoff was 2, for both HLA class I and II, and the microbiome cutoff was 25 for HLA class I and 37 for HLA class II. JanusMatrix cutoffs are defined such that only 5% of randomly generated HLA ligands exceed the thresholds.

Peptide Synthesis

Five milligrams of peptide for each epitope selected as defined above were prepared by Fmoc solid phase peptide synthesis (21st Century Biochemicals, Marlborough. Mass.) and HPLC purified to >90% purity (peak area). The peptide mass was verified by ESI-MS (QSTAR XL Pro, Qo-TOF) and the sequence of each peptide was verified by tandem mass spectrometry (CID MSMS).

HLA Binding Assays

HLA class II Binding Assay

A competition-based assay based on Steere et al. was employed (45). In 96-well plates, non-biotinylated test peptides over a three-log concentration range competed for binding to 50 nM soluble class II molecules (Benaroya Institute, Seattle, Wash.) against a biotinylated standard peptide at a fixed concentration (25 nM) at 37° C. for 24 hours to reach equilibrium. Class II molecules were then captured on ELISA plates using pan anti-class II antibodies (clone L243, anti-HLA-DR; Biolegend). Plates were washed and incubated with DELFIA Europium-labeled streptavidin (Perkin Elmer) for 1 hour at room temperature. DELFIA Europium activation buffer (Perkin Elmer) was added to develop the plates for 15-20 minutes at room temperature before data acquisition on a Time Resolved Fluorescence (TRF) plate reader. All assays were performed in triplicate. Binding assays were performed for 8 alleles: DRB1*0101, DRB1*0301, DRB1*0401, DRB1*0701, DRB1*0801, DRB1*1101, DRB1*301 and DRB1*1501. Dose-dependent binding data were fitted by non-linear regression to calculate $IC_{50}$ values for each peptide-HLA allele pair (GraphPad Prism Version 7). Peptide binding affinity was classified according to the following: very high ($IC_{50}$<0.1 μM), high ($IC_{50}$ 0.1-1 μM), moderate ($IC_{50}$ 1-10 μM) and low affinity ($IC_{50}$ 10-100 μLM). Epitopes with $IC_{50}$ values too high to accurately measure under binding conditions tested (>100 μM) or with no dose-dependent responses were considered non-binders.

HLA Class I Binding Assay

A competition-based assay based on fluorescence polarization, where reference fluorescent-labeled peptide is incubated with soluble HLA with or without competitor test peptides, was performed according to Buchli et al. (46). Peptide binding over a three-log concentration range was assessed for the A*0101, A*0201, A*0301, A*2402, B*0702 and B*4402 alleles. The latter was used to test B*4403 predictions. A dose response curve fit was obtained by non-linear regression to calculate $IC_{50}$ values for each peptide-HLA allele pair. Binding strength was classified according to $IC_{50}$ value: high (<5 IM), moderate (5-50 μM), low (50-1000 μM) or no affinity (>1000 μM or no dose-dependent response).

Assessment of Class II Epitope Immunogenicity in tgHLA-DR3 Mice

Multi-Epitope DNA Vaccine Engineering

Multi-epitope DNA vaccines were engineered by concatenating epitope sequences to form five multi-epitope genes, each containing 10 HLA Class II epitopes. To avoid production of neo-epitopes at epitope junctions, the VaxCAD algorithm was used to arrange epitopes in an order that diminishes potential junctional immunogenicity (40). Where re-ordering by VaxCAD did not sufficiently reduce potential junctional immunogenicity, Gly-Pro-Gly-Pro-Gly (SEQ ID NO: 52) spacer sequences were engineered between epitopes to further remove junctional epitopes. Genes were synthesized by GeneArt and subcloned at pre-determined flanking restriction sites downstream of the tissue plasminogen activator leader sequence in pNTC8682-eRNA41H (Nature Technology Corporation), a DNA vaccine vector that accommodates FDA recommendations for construction of plasmid DNA vaccines.

Plasmid DNA Vaccine Production

High purity plasmids for immunization % ere prepared by Nature Technology Corporation, Inc. at research grade. Each plasmid underwent quality control testing including spectrophotometric concentration and A260/A280 ratio determination (1.97), restriction digest analysis to assure the presence of the multi-epitope genes, agarose gel electrophoresis determination of residual host RNA and DNA (none detected), and quantitative endotoxin testing (<2.0 EU/mg).

Peptide Vaccine Preparation

Peptides produced by 21st Century Biochemicals corresponding to epitopes in the DNA vaccines were formulated in incomplete Freund's adjuvant (IFA) with 10 μg each of immunostimulatory CpG oligodeoxynucleotide 1826 (5'-TCCATGACGTTCCTGACGTT-3' (SEQ ID NO:56)), muramyl dipeptide (MDP) and CL097 (InvivoGen).

Mice

HLA-DR3 transgenic mice were obtained from Dr. Chella David (Mayo Medical School) under commercial license to EpiVax. The mice express the HLA-DRA and DRB1*0301 genes on a B.10-Ab0 mouse class II-negative background (47).

Vaccinations

Vaccine and placebo-treated mice (n=3/group) were all female and 6-8 weeks old at the start of heterologous DNA/DNA/peptide/peptide prime-boost immunizations. Epitopes were arranged into five groups of 10 epitopes in generally descending order of EpiMatrix epitope cluster score as follows: Group 1 (p9, p12, p14, p22, p27, p28, p31, p32, p45, p49), group 2 (p3, p7, p8, p15, p16, p38, p39, p42, p44, p46), group 3 (p4, p10, p19, p20, p21, p23, p25, p34, p40, p48), group 4 (p1, p2, p5, p6, p11, p13, p30, p36, p41, p47), group 5 (p17, p18, p24, p26, p29, p33, p35, p37, p43, p50). DR3 epitope scores correlated with cluster scores across the groups. DNA-prime vaccine was administered to mice intramuscularly by electroporation using the Ichor Medical Systems TriGrid platform with 20 μL of 10 μg naked plasmid DNA in sterile PBS injected into the quadriceps muscle. Mice received the DNA vaccine twice spaced by a two-week interval. Two weeks later, they were boosted twice with peptide vaccine at a two-week interval. For peptide immunizations, each mouse was administered 100 μl IFA emulsion (50 μg peptide) subcutaneously by needle stick injection. Four weeks after the final vaccination, tgHLA-DR3 mice were euthanized by administration of ketamine/xylazine intraperitoneally at 4 to 5 times the anesthetic dose (ketamine 80-100 mg/kg; xylazine 8-10 mg/kg).

Ex Vivo ELISpot Assay in Mouse Splenocytes

The frequency of epitope-specific splenocytes was determined by IFNγ ELISpot assay using the colorimetric Mabtech IFNγ ELISpot Kit with pre-coated plates according to the manufacturer's protocol. Washed splenocytes in RPMI 1640 (Gibco) supplemented with 10% fetal calf serum (FCS, Atlanta Biologicals) were added at $2.5 \times 10^5$ cells per well. Individual peptides were added at 10 μg/ml in triplicate wells. Peptide pools were added at 10 μg/ml, equating to 1 μg/ml per peptide. Triplicate wells were stimulated with 2 μg/ml Concanavalin A (ConA; Sigma Aldrich) as a positive control, and six replicate wells with medium containing 0.02% DMSO were used for background determination. Raw spot counts were recorded by ZellNet Consulting. Inc. using a Zeiss high-resolution automated ELISpot reader system and companion KS ELISpot software. Results were calculated as the average number of spots in the peptide wells, adjusted to spots per one million cells. A response in immunized mice was considered positive if the number of averaged spots was (i) at least twice as high as background (stimulation index ≥2), (ii) greater than 50 spot forming cells above background per million splenocytes (I response per 20,000 cells), and (iii) statistically different (p<0.05) from that of mock immunized mice by Student's t-test.

Human Study Cohort

Q-fever exposed individuals were recruited from a cohort characterized in a previous large Q fever study conducted in the village of Herpen, the Netherlands (48), which experienced a high incidence of *C. burnetii* infection during the 2007-2010 Q fever outbreak (49). All subjects had been tested using a Q fever interferon-γ release assay (IGRA, Q-Detect™) assay of cellular immunity during a previous study in which 80% of the adult population of Herpen were screened for Q fever (48). Individuals were invited to participate in the current study following preselection based on clinical history (disease, comorbidities, and medication) as well as IGRA and serological data generated during the previous study (48). To maximize the potential to detect *C. burnetii* epitope-specific T-cells, preference was given to donors with strong responses to whole heat-killed *C. burnetii* in the IGRA and without potentially confounding immune disorders. In addition, five individuals with known past symptomatic Q fever consented to participate. In total, 143 participants provided written informed consent. IGRA responses were re-assessed upon inclusion in October 2015. Volunteers who had no history of Q fever disease (48) and scored negative by immunofluorescence assay (50) as well as by IGRA in spring 2014 and upon inclusion into the present study in autumn 2015 were allocated to control group A (n=26). Seven volunteers that were IGRA positive in 2014 but did not meet positive scoring thresholds anymore 1.5 years later upon inclusion into the present study were excluded from further analysis. The remaining 110 volunteers that were positive by IGRA in both 2014 and 2015 w % ere subdivided based on past Q fever disease (either so registered (notified) in the national surveillance system, or self-reported) into groups B (asymptomatic, n=73) and C (symptomatic, n=37).

Whole Blood IFNγ Release Assay (Q-Detect™)

Whole lithium-heparin anti-coagulated blood was stimulated with *C. burnetii* antigen (heat killed Cb02629, Wageningen Bioveterinay Research, lot 14VRIM014) in 96-well polypropylene plates (Greiner BioOne) by adding 180 μl blood to 20 μl *C. burnetii* antigen diluted in phenol red-free RPMI supplemented with GLUTAMAX (2 mM), Gentamycin (5 μg/ml) and sodium pyruvate (1 mM, all ThermoFisher Scientific). A 1.5% (v/v, final concentration) solution of PHA-M (ThermoFisher Scientific), was added to separate wells as a positive control. Medium only was added to the negative control wells. All stimulations were performed in duplicate. After 22±1 hours whole blood cultures were re-suspended and IFNγ concentrations were assessed in whole blood by ELISA, using the IFNγ Pelipair protocol (Sanquin) with minor modifications. The upper detection limit of IGRA under these conditions is 1050 pg/ml. A subject was scored positive by IGRA if the *C. burnetii*-induced IFNγ production was ≥16 pg/ml above background and the ratio of the logarithmic value of background-subtracted *C. burnetii* and PHA responses ((log [*C. burnetii*]−log [neg control])/(log [PHA]−log [neg control])) was ≥0.4.

HLA Typing of Human Subjects

HLA typing was performed at the HLA laboratory at the Laboratory of Translational Immunology at the UMC Utrecht, the Netherlands. Genomic DNA was isolated from EDTA anti-coagulated blood within 48 hours upon collection using the MagNA Pure Compact system (Roche Diagnostics). The DNA samples were typed for HLA-A, -B (5'-UTR-3'UTR) and -DRB1 (exon 2-3'-UTR) by Next Generation Sequencing (NGS). Firstly, HLA target sequences were generated by long-range PCR using the Qiagen LongRange PCR kit and HLA-A, -B, and -DRB1 primers as described previously (51). Library preparation was performed using the GenDX NGSgo®-LibrX and NGSgo®-IndX kits following the manufacturers' recommendations (GenDX). Pooled samples were sequenced on an Illumina MiSeq by 2×250 paired end reading using the MiSeq reagent kit v2 (500 cycles). Sequences were analyzed with the NGSEngine software (GenDX). The resulting HLA-A, HLA-B, and HLA-DRB1 alleles were assigned to supertype families as defined by (42, 52) and/or based on homology of the HLA binding pockets. For determining allelic frequencies, donors homozygous for a given HLA allele were counted once.

Cultured ELISpot Assay Screening of Peptides in Human PBMCs

A combination of antigen-specific T-cell expansion culture and enzyme-linked immune spot assay (cultured ELISpot) was chosen as the primary assay for peptide screening, to achieve high sensitivity for detecting low frequency antigen-specific T-cell responses to *C. burnetii* peptides and facilitate detection of central memory T-cells (53). The protocol was adapted from Subbramanian et al, 2010 (54) and optimized at Innatoss using two reference peptide pools of MHC class I and class II peptides of CEF (Cytomegalovirus, Epstein-Barr virus, and influenza; JPT Peptide Technologies). A comparison of three media showed that RPMI medium supplemented with 10% FCS (HyClone) as a blocking and culture medium gave the best signal to background ratio in this ELISpot assay.

Antigen-Specific Expansion

PBMCs were isolated from lithium-heparin anti-coagulated blood using Leukosep tubes prefilled with Ficoll (Greiner BioOne) according to the manufacturer's recommendations. Isolated PBMCs were used for antigen-specific expansion cultures at 5×106 cells per well in 48-well flat bottom plates (Corning) in 150 µl complete RPMI (phenol red-free RPMI supplemented with GLUTAMAX (2 mM), Gentamycin (5 ug/ml), sodium pyruvate (1 mM, all Thermo Fisher Scientific) and 10% fetal bovine serum (HyClone). Antigen-specific expansion was performed using stimulation with pools of 10 peptides each (final concentration 2 µg/ml per peptide, 0.2% DMSO). On day 3 and 6 of culture, medium was refreshed by addition of an equal volume of complete RPMI with recombinant human IL-2 (Immunotools, final concentration 20 units/ml). On day 8, cells were harvested, counted and individual peptide responses assessed by ELISpot.

ELISpot Assay

MultiScreen IP filter plates (Merck Millipore) were pre-wetted with 35% ethanol, coated overnight with IFNγ capture antibody at the recommended concentration (Diaclone) in DPBS (Thermo Fisher Scientific) and blocked for at least 60 min with complete RPMI prior to addition of cells for re-stimulation. For each expansion culture, recovered cells were evenly distributed for peptide re-stimulation, negative and positive controls. Based on cell availability, a median of 38,000 cells per expansion pool (interquartile range (IQR) 27,000-52,000) were plated per replicate well. Assay wells were re-stimulated with each of the 10 respective individual peptides in quadruplicate (final concentration 2 µg/ml per peptide, 0.02% DMSO). Control wells were stimulated with either medium only (containing 0.02% DMSO; eight replicates) or with *Staphylococcus* enterotoxin B (SEB, final concentration I µg/ml, Sigma Aldrich, quadruplicate assays). After 20 hours incubation at 37° C., plates were washed, and sequentially incubated with a biotinylated anti-human IFNγ detection antibody and streptavidin-alkaline phosphatase conjugate in DPBS/0.5% FCS and developed using BCIP-NBT (all Diaclone) according to the manufacturer's recommendation. ELISpot plates were dried overnight, scanned on an AID Classic reader system and analyzed using the AID ELISpot software v7.0 (both AID Diagnostika GmbH). Spot forming units were counted using identical settings for all plates and all counts were reviewed and adjusted manually only where necessary to remove artefacts.

Data Analysis

To account for variation in background responses between expansion cultures and donors following cytokine-assisted T-cell expansion and to decrease the likelihood of detecting false positive responses in plates With either high background (when only considering an absolute difference to background) or low background (when only considering a fold difference above background), three combined threshold criteria were applied. Peptide re-stimulation responses were defined as positive when they were (i) significantly higher than spot counts in matched negative control wells from the same expansion culture by one-way ANOVA with Holm-Šidák multiple comparison correction post-hoc test, reached (ii) a stimulation index of at least 2 above the matched negative control wells and (iii) an absolute cut-off of >10 SFU/well.

Guinea Pig Reactogenicity Against Class I and II Peptides

Female Dunkin-Hartley guinea pigs were sensitized by intranasal inoculation with $10^6$ genome equivalents of *C. burnetii* Nine Mile strain or saline in 100 µL volume, as described previously (55). Peptides were tested by intradermal challenge, delivered at day 42 post sensitization. HLA class II and I peptides were administered in pools of five, with each peptide being tested twice in two different pool preparations. Peptide pools were created with 2 µg of each peptide (10 µg peptide per pool in total) in 100 µL saline with 1% DMSO. Challenge with 2 µg COXEVAC® whole cell vaccine (Ceva Sante Animale, Libourne, France) was used as a positive control; negative controls consisted of saline or 1% DMSO injections. On day 7, animals were anesthetized (ketamine 40 mg/kg and xylazine 5 mg/kg, i.p.) and euthanized with beuthanasia (i.p.). Gross reactions were monitored daily and skin biopsies obtained at day 7 post-challenge were fixed, sectioned, and stained with hematoxylin and eosin. Histological reactions were scored by an experimenter blinded to the treatment group, using the criteria previously described (55). Briefly, a score of 0 indicates no inflammation, 1 indicates localized macrophage dominated inflammation, 2 macrophage dominated inflammation with limited tissue infiltrations, 3 lymphocytic inflammatory infiltrates extending into the deep dermis, 4 edema and increased pyogranulomatous inflammation extending deep into the subcutis, and 5 widespread pyogranulomatous inflammation including necrosis.

Example 1. In Silico Identification of Predicted *C. burnetii* T-Cell Epitopes

Two *C. burnetii* antigen sets were selected as the basis for immunoinformatic identification of HLA class I and II T-cell epitopes. The first set (for HLA class I epitope prediction) was comprised of 53 published substrates of the type IV secretion system (T4SS), which are translocated from *C. burnetii* to the host cytoplasm where they are expected to enter the class I antigen processing pathway and trigger CD8' T cell responses (21, 23, 30-37). The second set (for both HLA class I and II epitope prediction) covered 40 sero-reactive *C. burnetii* antigens based on antibody responses in humans and mice, as well as evidence of processing and presentation to stimulate murine CD4+ T-cells (18, 26, 28, 29, 56). Using the EpiMatrix algorithm, 8,643 putative 9- and 10-mer T-cell epitopes predicted to bind to at least one of six HLA class I supertype alleles and 282 promiscuous epitope clusters, spanning 14 to 25 amino acids, predicted to bind HLA class II alleles covering >90% of the world-wide human population, were identified from the reference *C. burnetii* Nine Mile strain (Table 1).

The derived HLA class I epitopes and HLA class II promiscuous epitope clusters were then filtered to focus on sequences that (i) are conserved with other *C. burnetii* strains: (ii) have very high likelihood of binding human HLA alleles; (iii) exhibit low potential for cross-reactivity with peptides derived from the human proteome or microbiome based on the JanusMatrix algorithm (44); and (iv) do not present obvious issues for peptide synthesis or stability. Finally, 50 HLA class II epitope clusters (Table 2) and 65 HLA class I epitopes were selected for immune reactivity screening such that no source antigen was represented more than twice. Five epitopes were selected for each of the six HLA class I supertypes and for each antigen set (T4SS substrates and sero-reactive antigens), if possible giving preference to HLA class I ligands predicted to bind to at least two class I supertype alleles. An additional five HLA class I epitopes were specifically selected from the immunodominant *C. burnetti* antigen com1 (28, 56).

TABLE 1

Summary of in silico HLA class II and I epitope identification

| | HLA class II | HLA class I | |
|---|---|---|---|
| | Sero-reactive | T4SS substrates | Sero-reactive |
| Source antigens | 40 | 53 | 40 |
| Epitopes | 282 | 8,643 | 5,100 |
| Conserved across strains | 188 | 3,971 | 4,578 |
| High Scoring for HLA binding[1] | 153 | 1,710 | 1,945 |
| Different from human[2] | 98 | 1,511 | 1,558 |
| Without synthesis issues | 81 | 1,108 | 1,163 |
| Selected for immunogenicity tests[3] | 50 | 30 | 35 |

[1]Evaluated by EpiMatrix
[2]Evaluated by JanusMatrix
[3]No source antigen represented by more than two epitopes; five epitopes per antigen set for each of the 6 major HLA class I supertypes

TABLE 2

HLA class II epitopes selected for immune reactivity screening

| ID | Epitope | SEQ ID NO | CBU Code | UniProt ID RefSeq | Gene Name | Predicted HLA II restrictions (DRB1*) |
|---|---|---|---|---|---|---|
| p1 | SEQITLQTAEKVGLNVA | 1 | 1910 | H7C7D7 | com1 | 0101, 0301, 0401, 0701, 1101, 1301, 1501 |
| p2 | TPTFVIGNKALTKFGF | 2 | 1910 | H7C7D7 NP_820887.1 | com1 | 0101, 0301, 0401, 0801, 1101, 1301, 1501 |
| p3 | KDDILEAVANMSVMDV | 3 | 0229 | P0C8S3 NP_819273.1 | rplL | 0101, 0301, 0401, 0701, 0801, 1101, 1301, 1501 |
| p4 | KIGVIKAIRTITGLGLKEA | 4 | 0229 | P0C8S3 NP_819273.1 | rplL | 0101, 0401, 0701, 0801, 1101, 1301, 1501 |
| p5 | LAQYRELEAFSQFAS | 5 | 1943 | Q83AF7 NP_820919.1 | atpA | 0101, 0401, 0701, 0801, 1101, 1501 |
| p6 | SHEVLHAMSRGVEVLA | 6 | 1718 | P19421 NP_820699.1 | groL | 0101, 0301, 0401, 0701, 0801, 1101, 1501 |
| p7 | SRAFLTANKNKPGVKT | 7 | 0630 | P51752 NP_819660.1 | mip | 0101, 0301, 0401, 0801, 1101, 1301, 1501 |
| p8 | IKGWQEALTRMKPGAIWEI | 8 | 0630 | P51752 NP_819660.1 | mip | 0101, 0301, 0401, 0701, 0801, 1101, 1501 |

TABLE 2-continued

| HLA class II epitopes selected for immune reactivity screening | | | | | | |
|---|---|---|---|---|---|---|
| | | SEQ | Source antigen | | | Predicted HLA II |
| ID | Epitope | ID NO | CBU Code | UniProt ID RefSeq | Gene Name | restrictions (DRB1*) |
| p9 | AIYFIGWYANLAHIKLGIS | 9 | 2065 | Q83A45 NP_821036.1 | | 101, 0401, 0701, 0801, 1101, 1301, 1501 |
| p10 | EHTIVVNASASEAAALQ | 10 | 1943 | Q83AF7 NP_820919.1 | atpA | 0101, 0301, 0401, 0701, 0801, 1301, 1501 |
| p11 | PITKKQLKTMSNYEVIAK | 11 | 1869 | Q83AL4 NP_820846.1 | | 0101, 0401, 0701, 0801, 1101, 1301, 1501 |
| p12 | GKHFDGIKVLKLSPQNTI | 12 | 1869 | Q83AL4 NP_820846.1 | | 0101, 0301, 0401, 0701, 0801, 1101, 1301, 1501 |
| p13 | FTFRSQDSRRVQEW | 13 | 1853 | Q83AN0 NP_820830.1 | GtrA family protein | 0101, 0301, 0401, 0701, 1101, 1301, 1501 |
| p14 | PDYVLNAVNHIRYKP | 14 | 1835 | Q83AP6 NP_820814.1 | Proto-porphyrinogen oxidase | 0101, 0301, 0401, 0701, 0801, 1101, 1301, 1501 |
| p15 | MMEHLQNITNLVSTGRQGA | 15 | 1835 | Q83AP6 NP_820814.1 | Proto-porphyrinogen oxidase | 0101, 0301, 0401, 0701, 0801, 1101, 1301, 1501 |
| p16 | LKPFHFISSPTRDLQIA | 16 | 1716 | Q83B06 NP_820697.2 | gcvT | 0101, 0301, 0401, 0701, 0801, 1101, 1301, 1501 |
| p17 | KIPVKIIKPPFVRRG | 17 | 1716 | Q83B06 NP_820697.2 | gcvT | 0101, 0401, 0701, 1101, 1301, 1501 |
| p18 | QGHIINIGSISSHQV | 18 | 1513 | Q83BJ5 NP_820496.1 | short chain dehydrogenase | 0101, 0401, 0701, 1101, 1301, 1501 |
| p19 | EAVYKGFTPLKAEDIAEA | 19 | 1513 | Q83BJ5 NP_820496.1 | short chain dehydrogenase | 0101, 0401, 0701, 0801, 1101, 1301, 1501 |
| p20 | AQPIIHRLSTGQNTNP | 20 | 1416 | Q83BT6 NP_820400.2 | repressor protein C2 | 0101, 0401, 0701, 0801, 1101, 1301, 1501 |
| p21 | IARYFMVNISQLIGEE | 21 | 1416 | Q83BT6 NP_820400.2 | repressor protein C2 | 0101, 0301, 0401, 0701, 0801, 1501 |
| p22 | RLGFMSFFTKAVVEALKRF | 22 | 1398 | Q83BU7 NP_820383.1 | sucB | 0101, 0301, 0401, 0701, 0801, 1101, 1301, 1501 |
| p23 | REAVLFLVTIKELLEDP | 23 | 1398 | Q83BU7 NP_820383.1 | sucB | 0301, 0401, 0701, 0801, 1301 |

TABLE 2-continued

HLA class II epitopes selected for immune reactivity screening

| ID | Epitope | SEQ ID NO | Source antigen CBU Code | UniProt ID RefSeq | Gene Name | Predicted HLA II restrictions (DRB1*) |
|---|---|---|---|---|---|---|
| p24 | LPPVTSSVAVKVPSS | 24 | 1260 | Q83C69 NP_820254.1 | OmpA-like transmembrane domain protein | 0101, 0301, 0401, 0701, 1301, 1501 |
| p25 | SDMWQALLAGKSGVK | 25 | 0497 | Q83E37 NP_819531.1 | fabF | 0101, 0401, 0701, 0801, 1101, 1501 |
| p26 | QTQLQQSFSKRTMAT | 26 | 1221 | Q83CA7 NP_820216.1 | membrane-spanning protein | 0101, 0401, 0701, 1101, 1501 |
| p27 | RFDLSLMLNYPNSADRY | 27 | 1157 | Q83CG1 NP_820154.1 | Hypothetical exported protein | 0101, 0301, 0401, 0701, 0801, 1101, 1301, 1501 |
| p28 | ISLLVFKNSHRVQLWAK | 28 | 1157 | Q83CG1 NP_820154.1 | Hypothetical exported protein | 0101, 0301, 0701, 0801, 1101, 1301, 1501 |
| p29 | VARVSRLKDNFVVLEISKG TEITVQ | 29 | 1143 | Q83CH2 NP_820142.1 | yajC | 0101, 0301, 0401, 0701, 0801, 1101, 1501 |
| p30 | GTEITVQKASIASVLPK | 30 | 1143 | Q83CH2 NP_820142.1 | yajC | 0101, 0301, 0401, 0701, 1101, 1301, 1501 |
| p31 | AENVLIIHNKTLAHRYLA | 31 | 0968 | Q83CY3 NP_819976.1 | phospholipase D | 0101, 0301, 0401, 0701, 0801, 1101, 1301, 1501 |
| p32 | TGEIVKMINQAKQSIYVQG | 32 | 0968 | Q83CY3 NP_819976.1 | phospholipase D | 0101, 0301, 0401, 0801, 1101, 1301, 1501 |
| p33 | DGRLEQLNSQNQQLQ | 33 | 0891 | Q83D52 NP_819907.1 | membrane-associated protein | 0101, 0401, 0701, 0801, 1101, 1501 |
| p34 | PAKINLARTYIAMED | 34 | 0891 | Q83D52 NP_819907.1 | membrane-associated protein | 0101, 0301, 0401, 0701, 0801, 1101, 1301, 1501 |
| p35 | VFNITLQKVMAPELPVL | 35 | 0737 | Q83DJ3 | tig | 0101, 0401, 0701, 1101, 1301, 1501 |
| p36 | IDHLQQMTRQQVAMQTHK | 36 | 0737 | Q83DJ3 NP_819763.1 | tig | 0101, 0301, 0401, 0701, 0801, 1101, 1301, 1501 |
| p37 | VAKLRGDLSSIIHKL | 37 | 0718 | Q83DK8 NP_819763.1 | membrane-associated protein | 0101, 0301, 0401, 0701, 1301, 1501 |
| p38 | LSSIIHKLTSFSKTEA | 38 | 0718 | Q83DK8 NP_819746.1 | membrane-associated protein | 0101, 0301, 0401, 0701, 0801, 1101, 1301, 1501 |

TABLE 2-continued

HLA class II epitopes selected for immune reactivity screening

| ID | Epitope | SEQ ID NO | CBU Code | Source antigen UniProt ID RefSeq | Gene Name | Predicted HLA II restrictions (DRB1*) |
|---|---|---|---|---|---|---|
| p39 | QELEVAQNKAMSDFM | 39 | 0612 | Q83DT1 WP_010957688.1 | ompH | 0101, 0301, 0401, 0801, 1101, 1301, 1501 |
| p40 | QNAFQLQETIVSTEN | 40 | 0545 | Q83DZ3 NP_819577.2 | lemA | 0101, 0301, 0401, 0801, 1101, 1301, 1501 |
| p41 | LKDVVALRNQAQTAK | 41 | 0545 | Q83DZ3 NP_819577.2 | lemA | 0101, 0301, 0401, 0701, 0801, 1101, 1501 |
| p42 | DHAYKLAVSSTKSMT | 42 | 0497 | Q83E37 NP_819531.1 | fabF | 0101, 0301, 0401, 0701, 0801, 1101, 1301, 1501 |
| p43 | NAGIIRNKLKIQATIN | 43 | 0383 | Q83EE1 NP_819422.2 | tag | 0301, 0801, 1101, 1301 |
| p44 | GLSWLTILKKRNNYRDSFN | 44 | 0383 | Q83EE1 NP_819422.2 | tag | 0301, 0801, 1101, 1301, 1501 |
| p45 | GVAYTYNRANAGLPTNK | 45 | 0307 | Q83EL2 NP_819350.1 | outer membrane protein | 0101, 0301, 0401, 0701, 0801, 1101, 1501 |
| p46 | VPGYRNASSKRFVAP | 46 | 0307 | Q83EL2 NP_819350.1 | outer membrane protein | 0101, 0301, 0401, 0701, 0801, 1101, 1301, 1501 |
| p47 | KAQLIQLKTHVTINAT | 47 | 0109 | Q83F42 NP_819159.1 | methionine-binding protein | 0101, 0301, 0401, 0701, 0801, 1101, 1301 |
| p48 | SPAVLSAAKKIFGDGA | 48 | 0109 | Q83F42 NP_819159.1 | methionine-binding protein | 0301, 0701, 0801, 1101, 1301, 1501 |
| p49 | DQRITQLKNLNSNNSDSSNDN | 49 | 0092 | Q83F57 NP_819144.2 | ybgF | 0101, 0301, 0401, 0701, 0801, 1101, 1301, 1501 |
| p50 | LRPVRYFTGVPSPVKTPE | 50 | 1200 | Q9ZH99 NP_820195.2 | icd | 0101, 0401, 0701, 1101, 1301, 1501 |

Example 2. HLA Binding of Predicted *C. burnetii* Epitopes

Figure 1:
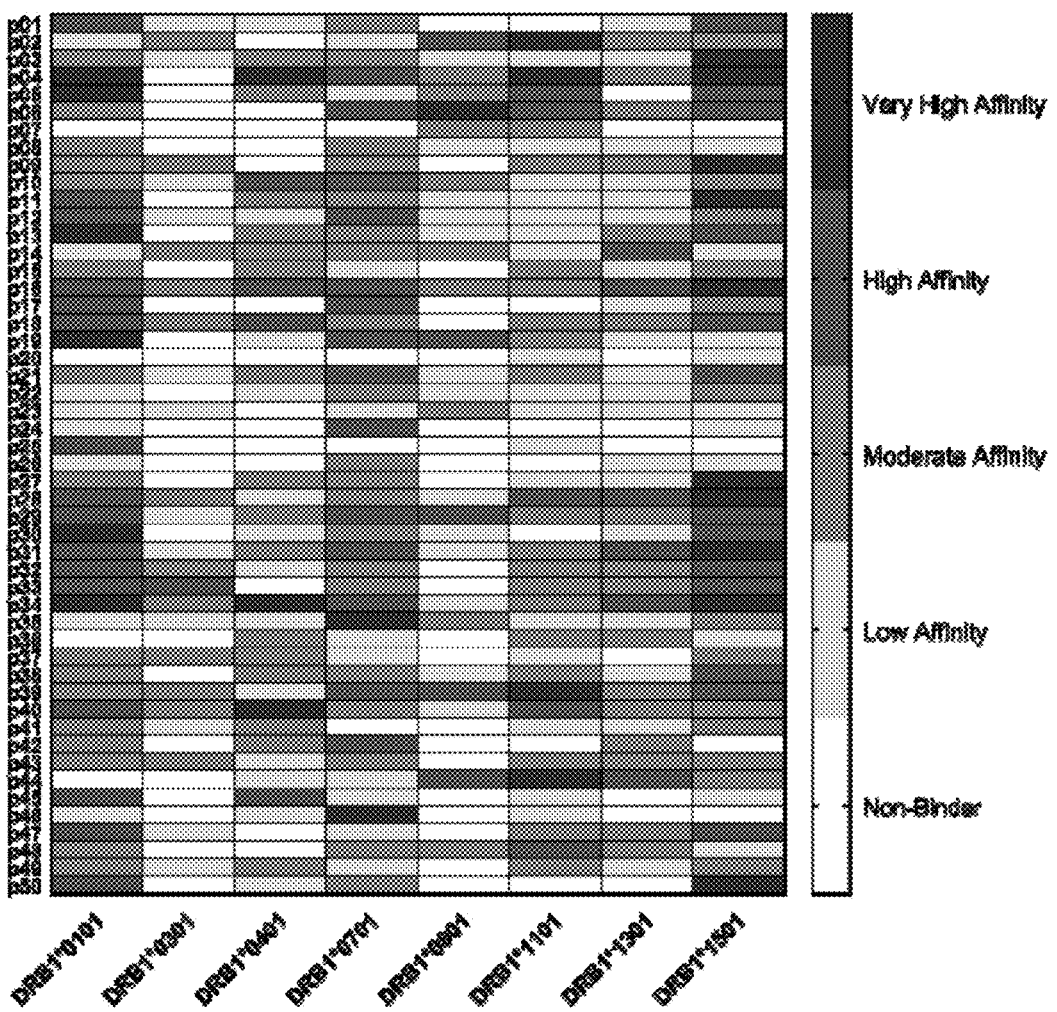
FIG. 1. HLA Class II Binding Assay Results. *C. burnetii* HLA class II epitope affinities for eight common DR alleles were assessed in competition binding assays. Peptide binding strength was classified according to $IC_{50}$ value in the following affinity categories: very high (<0.1 µM), high (0.1-1 µM), moderate (1-10 µM) and low (10-100 µM). Epitopes with $IC_{50}$ values >100 µM or with no dose-dependent response were considered non-binders.

Epitope predictions were validated using HLA binding assays. Peptides representing the 50 promiscuous *C. burnetii* HLA class II epitope clusters were assayed in competition binding assays against each of the eight class II HLA supertype alleles (FIG. 1). Each of the peptides bound as predicted to at least two HLA-DR alleles: 6% bound to two HLA-DR alleles, 2% to three alleles, 10% to four alleles, 4% to five alleles, 28% to six alleles, 24% to seven alleles, and 26% to all eight alleles. Independent of original binding predictions, amongst all 400 peptide-allele pairs tested, 6.5% of peptides bound with very high affinity ($IC_{50} < 0.1$ μM), 16% of peptides bound with high affinity ($IC_{50}$ 0.1-1 μM), 30% bound with moderate affinity ($IC_{50}$ 1-10 μM), 25.5% bound with low affinity ($IC_{50}$ 10-100 μM) and 22% exhibited no detectable affinity for the HLA-DR tested ($IC_{50} > 100$ μM or no dose-dependent response). Overall, 81% of predicted binding events and 41% of predicted non-binding events were verified in vitro. Collectively, the agreement of computational predictions with binding assay results was 75% ($\chi^2$, $p < 0.001$), ranging from 60% to 88% for individual alleles (Table SI), consistent with published studies using the same algorithms and assay conditions (57, 58).

Figure 2:
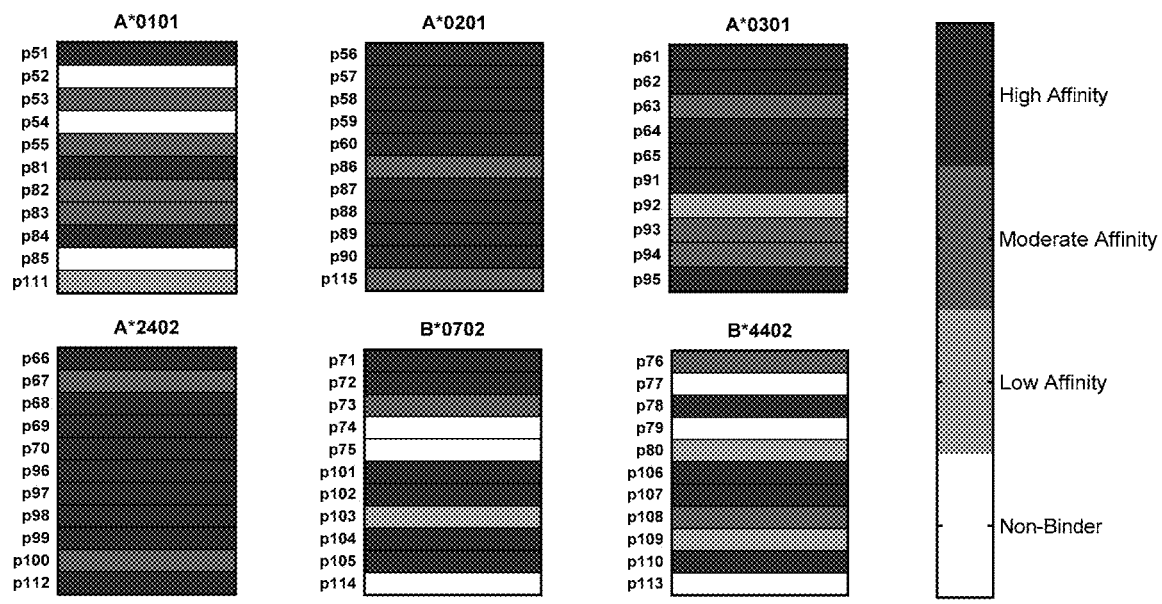
FIG. 2. HLA Class I Binding Assay Results. *C. burnetii* HLA class I epitope affinities for six supertype HLA-A and HLA-B alleles were assessed in competition binding assays. Peptide binding strength was classified according to $IC_{50}$ value in the following categories: high affinity (<5 µM), moderate affinity (5-50 µM) and low affinity (50-1000 µM). Epitopes with $IC_{50}$ values >1000 µM or with no dose-dependent response were considered non-binders.
Figure 3A:
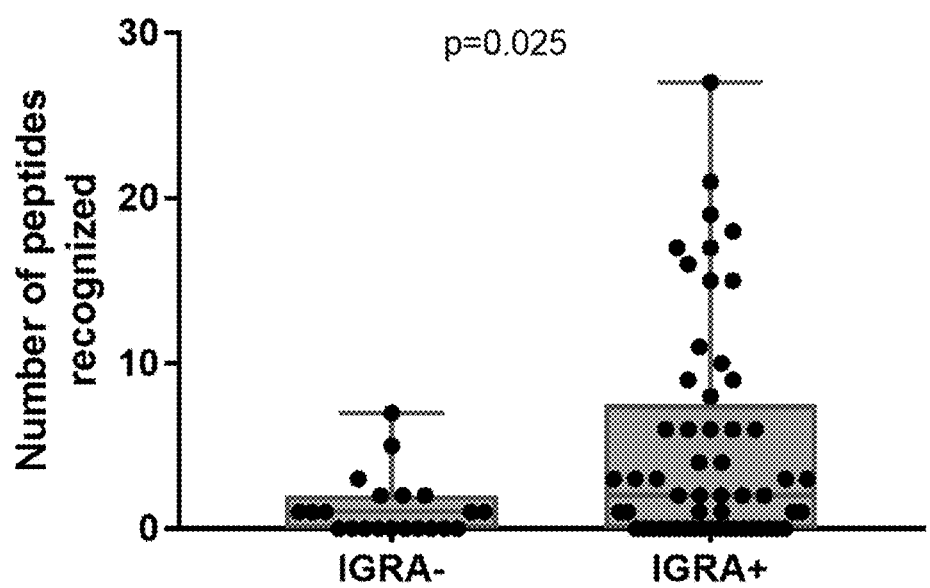
FIGS. 3A-D. Cumulative HLA class II peptide responses across clinical groups and in relation to IGRA. Data are shown for IGRA− and IGRA+ as the cumulative peptide response (SI≥2) per donor (A) or as the proportion of subjects recognizing 0, 1-2, 3-5, 6-10 or >10 peptides (B), (C) The cumulative number of peptides recognized by individual IGRA+ subjects was plotted against their IGRA response to whole heat-killed *C. burnetii* and analyzed by Spearman correlation. (D) IGRA responses are shown for IGRA+ individuals recognizing 0-2 or ≥3 peptides (cut-off SI≥2). Groups in (A) and (D) were compared by Mann-Whitney-test. Whisker-dot-plots show the median and interquartile range ($25^{th}$ and $75^{th}$ percentile) with whiskers extending from min to max values.
Figure 3B:
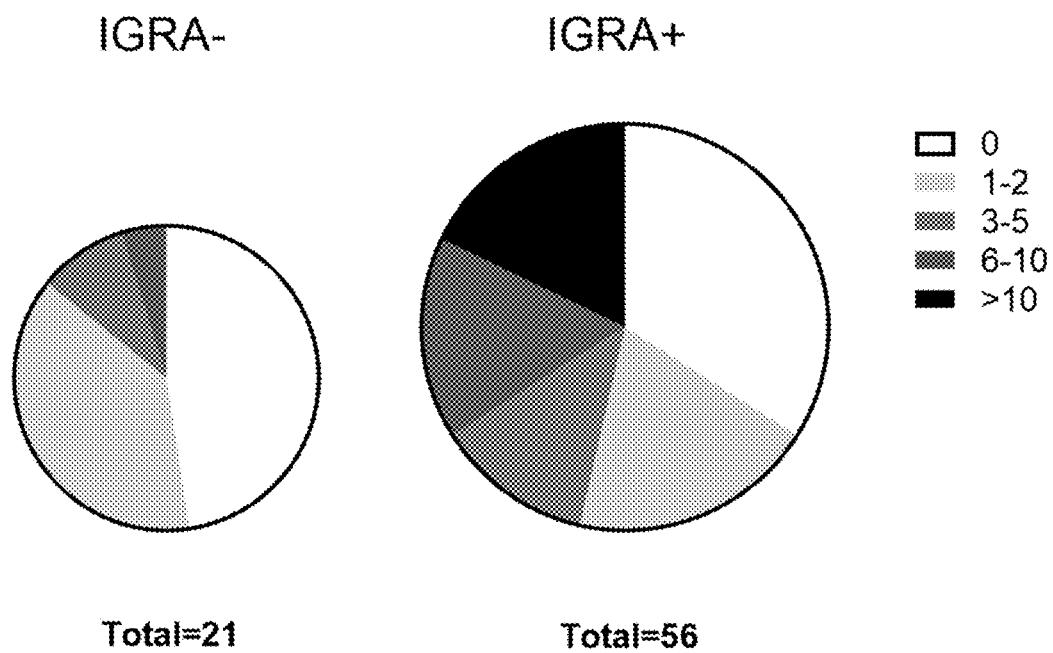
Figure 3C:
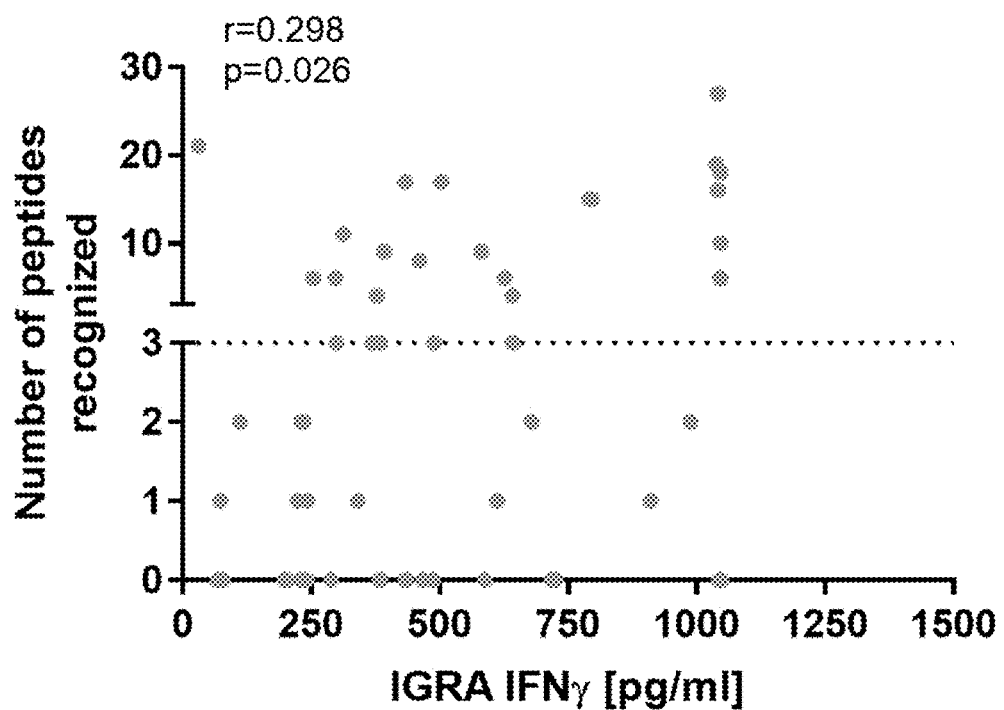
Figure 3D:
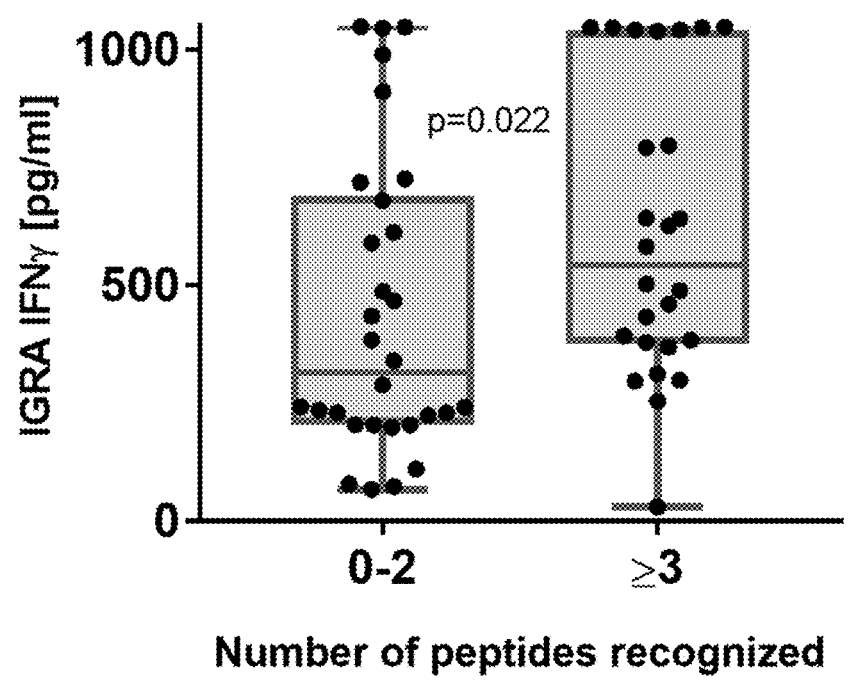
Figure 4A:
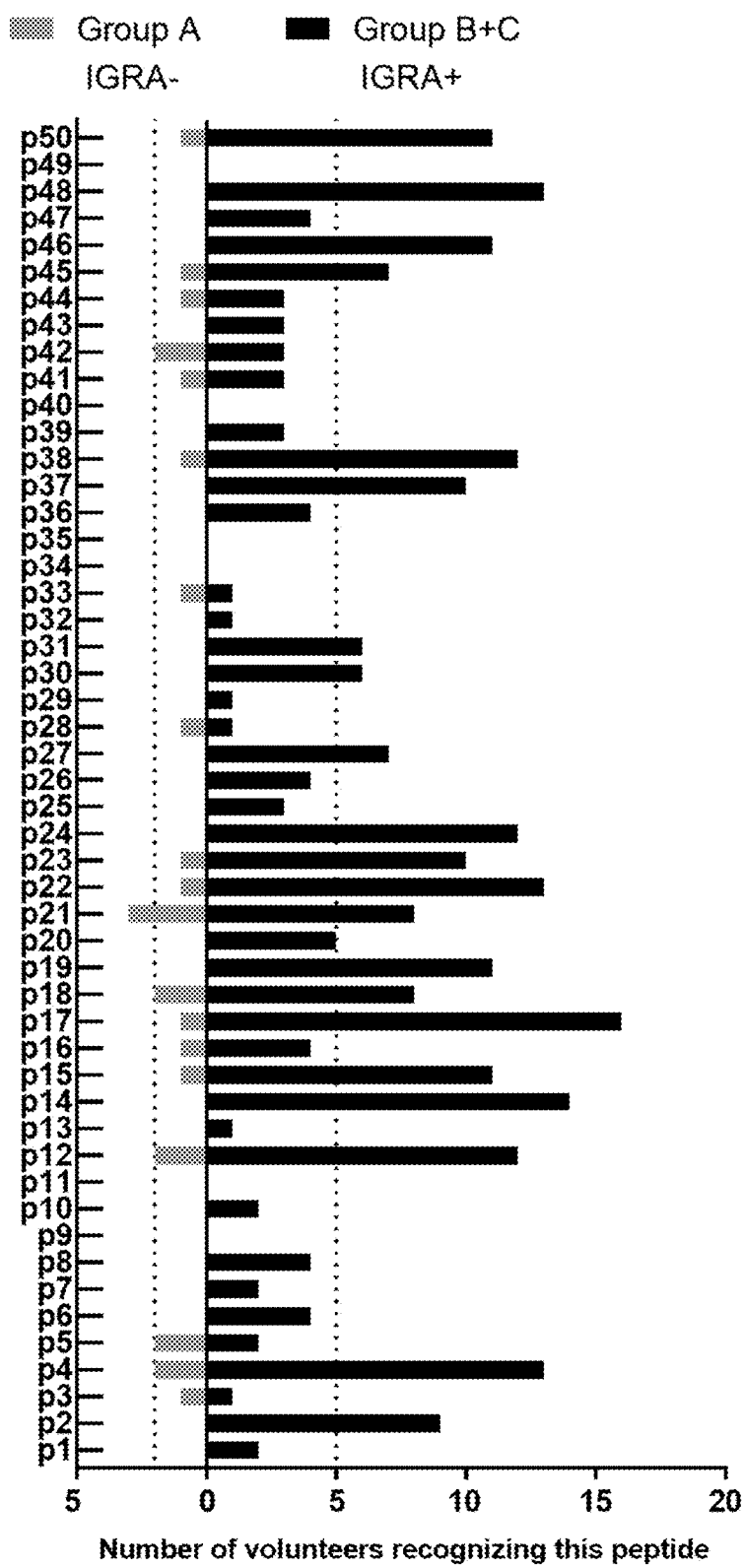
FIGS. 4A-B. Highly antigenic HLA class II peptides identified by cultured IFNγ ELISpot assay.
Figure 4B:
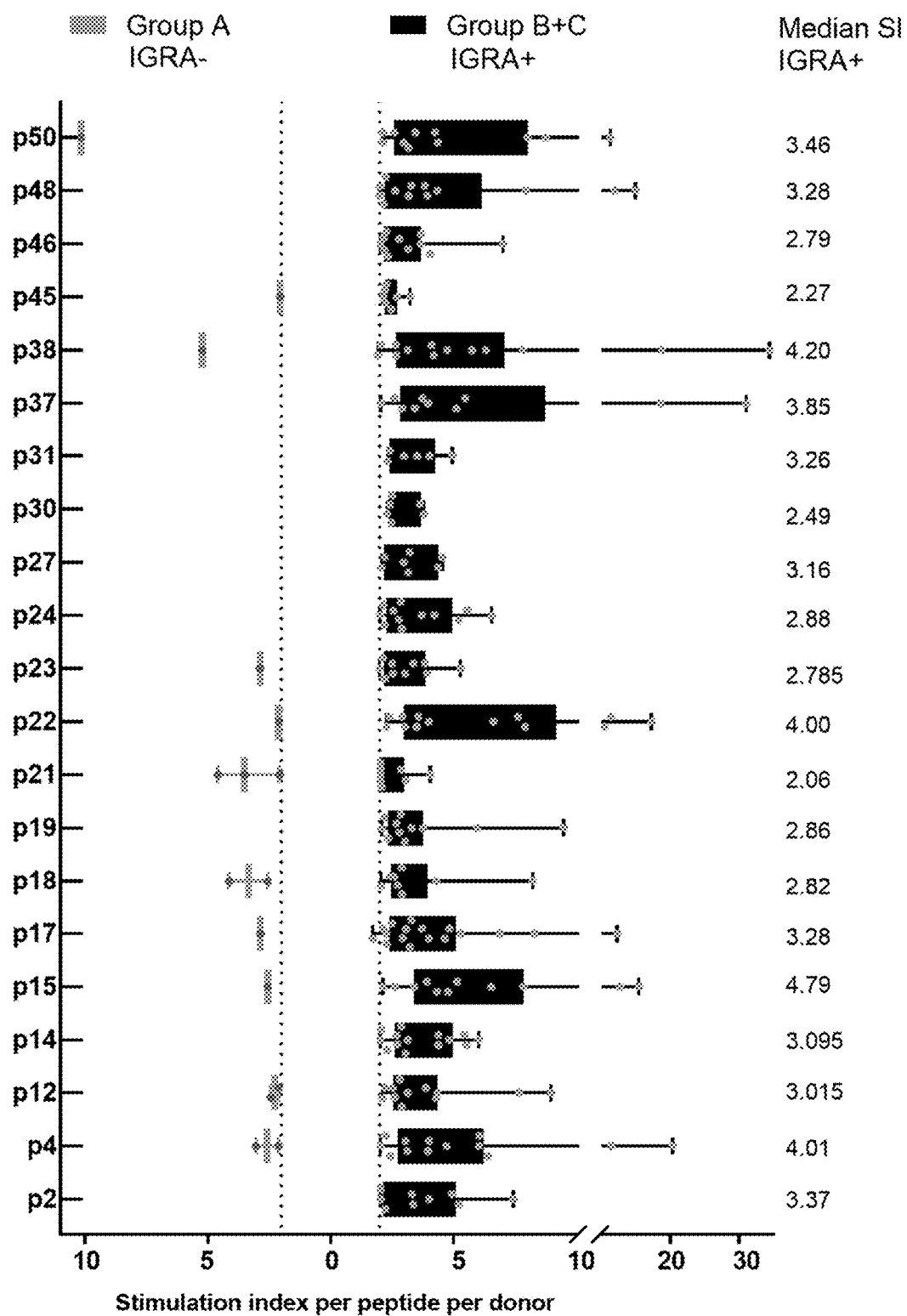
Figure 5A:
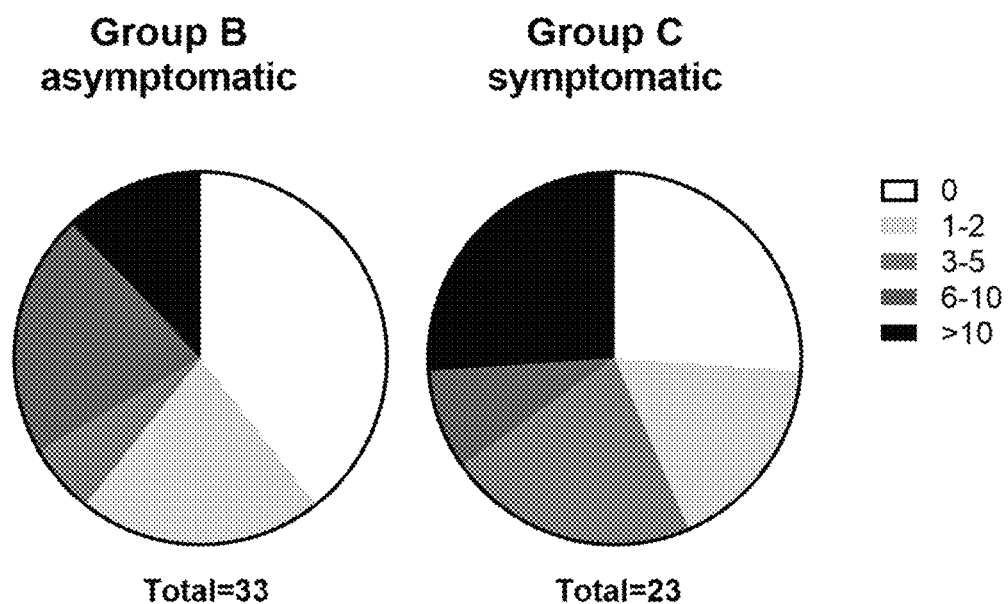
Figure 5B:
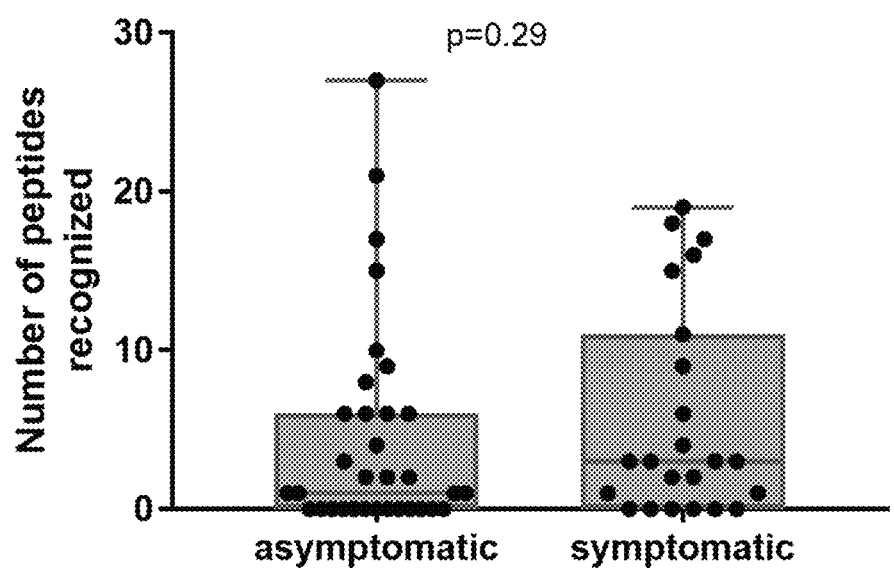
Figure 5C:
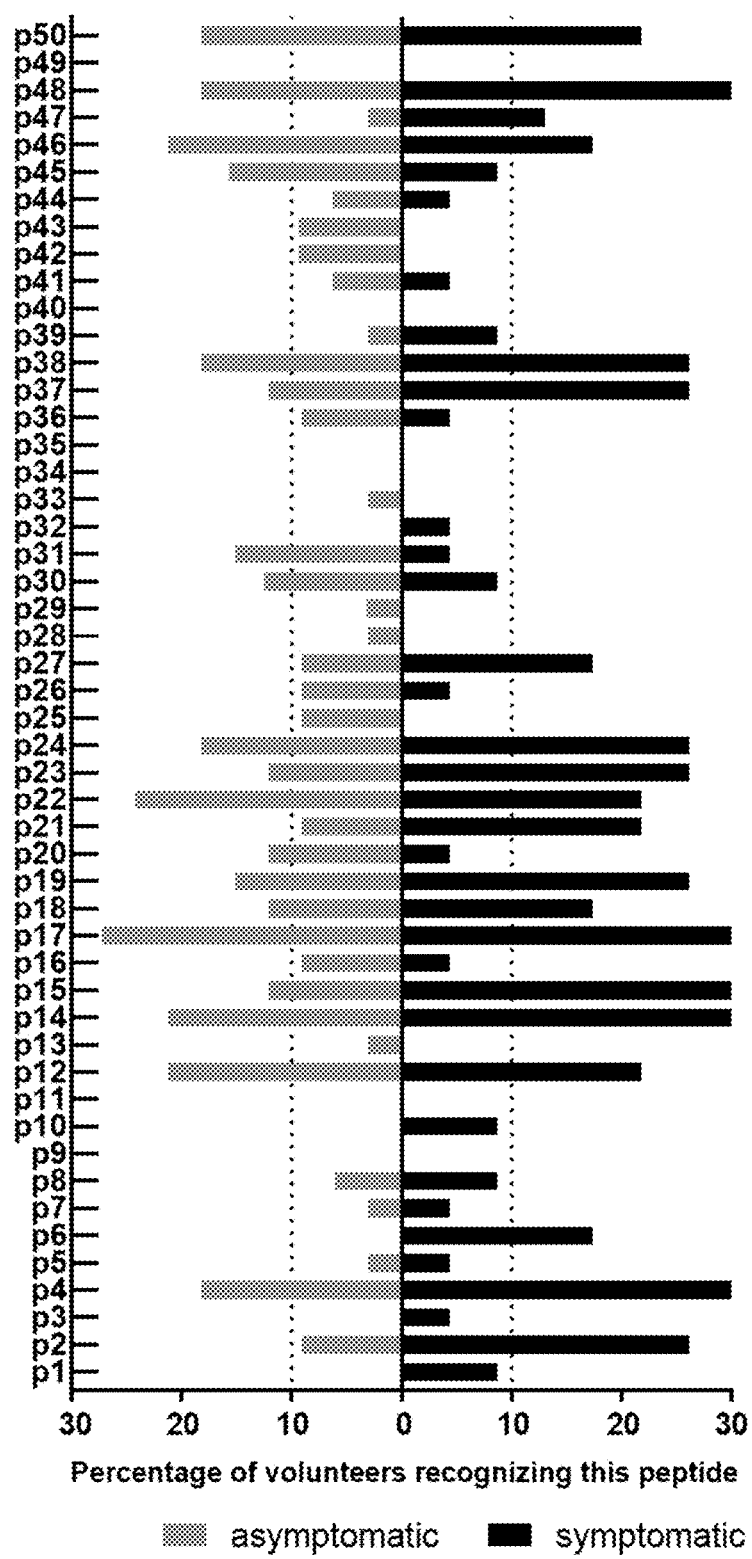

HLA class I binding affinities were determined for the primary predicted HLA-A/B supertype allele for each peptide (FIG. 2). Among the 65 peptide-allele pairs tested, 56% bound with high affinity ($IC_{50}$<5 µM), 21.5% with moderate affinity ($IC_{50}$ 5-50 µM), 7.5% with low affinity ($IC_{50}$ 50-1000 µM) and 14% exhibited no detectable affinity for the HLA class I allele tested ($IC_{50}$>1000 µM or no dose-dependent response). All predicted A*0201, A*0301 and A*2402 peptides, and 8/11 A*0101 and B*0702 peptides bound HLA as predicted. An assay using B*4403 molecules was not available, but an assay using the related B*4402 allele showed eight out of 11 B*4403 peptides bound HLA as predicted. Based on these results, epitope prediction accuracy was 100% for A*0201, A*0301 and A*2402 and 73% for A*0101, B*0702 and 11*4403. Overall, predictive accuracy for this set of HLA class I peptides was 89%. Taken together, the binding assay results suggest that the predicted HLA class II epitope clusters and HLA class I epitopes represent a set of sequences with meaningful potential for stimulating *C. burnetii*-specific immune responses across a broad range of HLA types.

Example 3. Immunogenicity of Class II Epitopes in tgHLA-DR3 Mice

While peptide binding to HLA is necessary to induce a T-cell response, it is not sufficient. To determine whether the predicted *C. burnetii* HLA class II epitope clusters are capable of eliciting a de novo immune response via a cognate human HLA in vivo, the class II peptides were screened for immunogenicity in transgenic mice expressing human HLA-DR3 (tgHLA-DR3). The 50 HLA class II *C. burnetii* peptides were arranged into five groups of 10 peptides each based on predicted HLA-DR3 immunogenicity and three mice per group were subjected to heterologous DNA/DNA/peptide/peptide prime-boost immunizations. Peptide-specific responses of splenocytes from tgHLA-DR3 mice were assessed by ex vivo IFNγ ELISpot assay. Positive peptide-specific IFNγ responses in vivo were observed for 11 peptides, eight of which evoked responses in at least 2/3 mice (Table 3). All 11 of these immunogenic peptides were predicted to bind HLA-DR3, and all except one (p36) also showed binding to DRB1*0301 in vitro. Therefore, altogether 10/21 peptides both predicted and confirmed to bind HLA-DR3 were immunogenic in vivo. None of the 13 peptides that were predicted not to bind HLA-DR3 were immunogenic. An odds ratio, calculated to determine the association of epitope prediction and immunogenicity, showed a statistically significant association for immunogenicity given an HLA-DR3 prediction (Fischer's exact test, p=0.0229). No peptide-specific responses were detected in mock-immunized mice that received vehicle vaccine controls.

TABLE 3

*C. burnetii* HLA class II epitope immunogenicity in tgHLA-DR3 mice

| Peptide ID | # of mice responding[4] | Mouse 1/3 | | | Mouse 2/3 | | | Mouse 3/3 | | |
|---|---|---|---|---|---|---|---|---|---|---|
| | | SFU[1] | SI[2] | p-value[3] | SFU[1] | SI[2] | p-value[3] | SFU[1] | SI[2] | p-value[3] |
| p2 | 2 | 120 | 6.63 | 0.0003 | 141 | 8.28 | <0.0001 | 18 | 1.53 | 0.1384 |
| p10 | 2 | 256 | 5.80 | <0.0001 | 82 | 4.51 | 0.0043 | 43 | 2.00 | 0.0496 |
| p14 | 2 | 157 | 7.94 | 0.0006 | 371 | 20.21 | 0.0001 | 11 | 1.42 | 0.0149 |
| p16 | 1 | 180 | 8.94 | 0.0007 | 27 | 2.05 | 0.0060 | 19 | 1.94 | 0.0164 |
| p23 | 2 | 69 | 2.30 | 0.0038 | 21 | 1.89 | 0.0372 | 63 | 2.47 | 0.0172 |
| p28 | 2 | 63 | 3.76 | 0.0013 | 54 | 3.79 | 0.0094 | 41 | 2.63 | 0.0227 |
| p31 | 1 | 0 | 0.88 | 0.1143 | 14 | 1.72 | 0.0621 | 84 | 4.32 | 0.0007 |
| p32 | 2 | 64 | 3.82 | 0.0053 | 70 | 4.62 | 0.0103 | 28 | 2.11 | 0.0609 |
| p36 | 2 | 52 | 3.44 | 0.0468 | 55 | 3.86 | 0.0193 | 0 | 0.86 | 0.2215 |
| p41 | 1 | 87 | 5.06 | 0.0052 | 30 | 2.55 | 0.0433 | 0 | 0.98 | 0.3566 |
| p43 | 3 | 135 | 4.88 | 0.0001 | 65 | 3.04 | 0.0013 | 116 | 4.48 | 0.0001 |

[1]Average number of spot forming units (SFU) per million splenocytes from triplicate wells; the average number of SFU/million in medium only control wells was subtracted. Negative values were assigned 0.
[2]Stimulation index (SI) calculated as average number of SFUs in peptide stimulated wells over medium only control wells
[3]SFUs in peptide stimulated wells from immunized mice compared to mock-immunized mice by Student's t-test
[4]Mice were deemed responsive to a peptide if their SFU was greater than 50 and if their SI was greater than 2 and if their p-value is lower than 0.05

Example 4. Selection of *Coxiella*-Exposed Human Subjects for Epitope Antigenicity Screening The transgenic mouse study provided a snapshot of peptide-specific immunogenicity for a single HLA class II allele. To assess antigenicity across multiple HLA types and determine whether the selected class I and II peptides are capable of recalling long-lasting IFNγ memory responses, we next turned to a unique cohort of individuals naturally exposed to *C. burnetii*. Subjects for this study were recruited from a well-characterized population in the village of Herpen in the Netherlands (48), which experienced a high incidence of *C. burnetii* infection during the 2007-2010 Q fever outbreak. Recruited subjects were categorized based on clinical Q fever history and recall responses to heat-killed *C. burnetii* in a whole blood IFNγ release assay (IGRA) (Table 4). Group A and B subjects had no clinical history of Q fever, while group C individuals had recovered from an acute episode of diagnosed Q fever. Group A controls had no IFNγ recall responses to *C. burnetii*. Group B (past asymptomatic infection) and group C (past symptomatic infection) subjects showed varying degrees of IFNγ recall responses to *C. burnetii* (both p<0.0001 compared to group A controls by one-way ANOVA with Holm-Sidák multiple comparisons test), with no significant difference between the two groups (p=0.9). HLA types were sufficiently diverse within the total cohort to have all desired HLA types represented in all three clinical groups, with the exception of HLA-DR8, which is underrepresented particularly in group C, in accordance with this allele's expected low frequency in the Dutch population (42, 59, 60). Assessment of the binding potential of all peptides with respect to the HLA types of the 136 subjects in groups A-C showed no significant differences across groups, with 75-82% of all class I peptides and between 93-96% of all class II peptides predicted to be recognized by each group.

Two partially overlapping subgroups of the total cohort were selected based on a broad representation of HLA-A/HLA-B and HLA-DR supertypes and allocated to HLA class I and II peptide screening, respectively. The screening cohort for the 50 HLA class II peptides consisted of 21 group A control donors (IGRA−, no clinical disease), and 56 IGRA+ donors from groups B (asymptomatic, n=33) and C (symptomatic, n=23). The screening cohort for the 65 HLA class I peptides included 20 group A control donors (IGRA−, no clinical disease), and 57 IGRA+ donors from groups B (asymptomatic, n=32) and C (symptomatic, n=25) (Table S3). Care was taken to maintain a distribution of IGRA responses comparable to the total cohort.

TABLE 4

Categorization of human study subjects

| Group | N | Age in years (median, IQR)[1] | Females N (%) | Coxiella-specific IFNγ response in pg/ml (median, IQR)[2] | Previous clinical Q-fever episode[3] |
|---|---|---|---|---|---|
| A (controls) | 26 | 55 [47-67] | 14 (54%) | 3 [1-10.3] | − |
| B (past asymptomatic) | 73 | 54 [47-63] | 47 (64%) | 330 [168-660] | − |
| C (past symptomatic) | 37 | 54 [48-63] | 20 (54%) | 348 [180-717] | + |

[1]At inclusion into the study in October 2015
[2]At inclusion into the study in October 2015, medium only background subtracted
[3]Either formally notified or self-reported (48)

Example 5. Human Antigenic Responses to Predicted HLA Class II Epitopes

Human antigenic T-cell IFNγ recall responses against the predicted epitope clusters from *C. burnetii* were evaluated ex vivo using freshly isolated peripheral blood mononuclear cells (PBMCs) in a cultured ELISpot assay for detection of central memory T-cells. A cultured ELISpot assay was used to achieve high sensitivity for detecting low frequency antigen-specific T-cell responses. Amongst the 3,843 assessments made for the HLA class II peptides (50 peptides screened against 77 donors with some exceptions due to technical error or insufficient cell numbers), 307 yielded positive responses (stimulation index (SI)≥2, Figure S1 and S2). These antigenic responses covered 44/50 HLA class II peptides. Only six peptides were not recognized by any subject (p9, p11, p34, p35, p40 and p49). For four of these peptides, a second peptide from the same respective source antigen induced recall responses by at least one IGRA+ subject. Therefore, responses were detected to all but two (CBU_2065 and CBU_0092/YbgF) of the 29 source antigens from which HLA class II epitope clusters were predicted and screened.

The cumulative HLA class II peptide response per subject was more frequent in IGRA+ compared to IGRA− subjects (FIG. 3A). The majority of IGRA-individuals recognized none (10/21 donors) or only one or two peptides (8/21 donors). While only 14% (3/21) of IGRA− group A individuals recognized three or more peptides, this was true for 46% (26/56) IGRA+ group B and C donors (FIG. 3B). Amongst IGRA+ individuals, there was a positive correlation between the cumulative number of recognized peptides per donor, and the IFNγ responses to whole heat-killed *C. burnetii* as assessed 12-17 months prior to peptide screening (FIG. 3C). Of note, all but one individual that showed responses to three or more peptides had an IGRA response of at least 250 μg/ml IFNγ in this standardized assay (FIG. 3D).

Of the 44 antigenic HLA class II peptides, 21 peptides were recognized by >10% of all IGRA+ individuals (at least 6/56, FIG. 4A) and were hence considered highly antigenic. These 21 highly antigenic peptides accounted for 78.3% of all positive peptide responses of IGRA+ individuals that reached a SI≥2 (220/281). A large proportion of these responses was well above the cut-off of SI≥2: Amongst responding IGRA+ individuals, responses to 13 of these 21 peptides showed a median SI between 3.0 and 4.8 (FIG. 4B), and for 11 of these peptides >10% of all IGRA+ donors reached at least SI≥3. Amongst IGRA− control subjects group A, these peptides elicited either no recall responses (11/21), or responses from only one or two individuals. Only for a single peptide (p21) did the recall response frequency reach a similar proportion in IGRA− (3/21: 14.3%) as in IGRA+ donors (8/56: 14.3%). Amongst the 21 highly antigenic peptides, there were five source proteins that were represented by two epitopes each (p14+p15. CBU_1835/protoporphyrinogen oxidase; p18+p19, CBU_1513/short chain dehydrogenase: p22+p23, CBU_1398/SucB, p37+p38, CBU_0718, p45+p46, CBU_0307/outer membrane protein). Notably, not only were all 11 of the tgHLA-DR3 mice immunogenic peptides also antigenic in at least one IGRA+ individual, but five of the tgHLA-DR3 immunogenic peptides were amongst the 21 highly reactive peptides in the human cohort (p2, 14, 16, 22, 31).

Amongst IGRA+ donors, group C of past symptomatic individuals had a higher proportion of high responders (recognizing >10 peptides) and a smaller proportion of non-responders to HLA class II epitope clusters than past asymptomatic subjects (Group B, FIG. 5A). However, the two groups did not differ significantly in their cumulative peptide response per subject (FIG. 5B). When comparing responses to individual peptides between group B and C, there was again a trend that responses particularly to the most antigenic peptides were more frequent amongst past symptomatic donors and a number of peptides were recognized only within this group by either a single (p3, p33) or multiple donors (p1, p6, p10) (FIG. 5C). There were some peptides, however, that were recognized solely by past asymptomatic subjects (p25, p42 and p43, 3/33 each; p13, p28, p29 and p33, 1/33 each).

Example 6. Human Antigenic Responses to Predicted HLA Class I Epitopes

Recall responses to the 65 HLA class I peptides were also assessed using the cultured IFNγ ELISpot approach. In 4,794 assessments (65 peptides screened in 77 donors with some exceptions due to technical error or insufficient cell numbers), only 23 positive responses were detected. Four of these positive responses came from IGRA− group A control subjects. The remaining 19 responses were detected in IGRA+ subjects, with one individual recognizing 8 different peptides. Of the 15 HLA class I peptides that were found to be antigenic in humans, ten peptides were recognized by only a single donor each and only five HLA class I peptides were recognized more than once: p53, p91 and p92 were each recognized by 2/57 donors, and two epitopes (p111 and p113) from com1 were recognized by 3/57 and 4/57 donors, respectively. Only two of the reactive peptides came from the T4SS data set (p53, p54), the remaining 13 were derived from sero-reactive source antigens. Albeit rare, HLA class I peptide responses were clearly detectable, with nearly half (11/23) of the positive responses reaching a stimulation index (SI) of ≥3, and all responses were consistent with predictions for primary or secondary HLA-A/B allele binding.

Example 7. Evaluation of Class I and Class II Epitopes in Guinea Pig Model of Vaccine Reactogenicity Due to reactogenicity issues observed with the only Q fever vaccine licensed for humans, all *C. burnetii* HLA class I and class II peptides examined in this study were screened for potential reactogenicity in a guinea pig model of exposure-primed delayed-type hypersensitivity (61, 62), with the goal of eliminating reactogenic peptides from further consideration for inclusion in a vaccine. In contrast to reactogenicity mediated by the whole cell phase I vaccine COXEVAC®, no gross reactions were noted at any of the negative control or peptide pool injection sites. Mild lymphocytic inflammation (score=1) was noted in two HLA class II peptide pools: no overlap in peptides was noted between the two pools and no other pools with the same peptides showed histological changes. Therefore, these reactions were not likely to be considered a reactogenic response to *C. burnetii* peptides.

Example 8. Generate Optimized Vaccine for Protective Immunity Study in Small Animal Infection Model

*C. burnetii* class II epitope concatemers were used for production of a ChAd-vectored Q fever vaccine. Three different sets of epitopes were developed from human and mouse immunoreactivity data generated in prior work using the 50 class II epitopes initially identified by immunoinformatic methods:

1) 18 epitopes comprising mouse immunoreactive peptides+human immunoreactive peptides in ≥20% of IGRA+ donors (SI≥2) and ≥10% of IGRA+ donors (SI≥3) (epitopes: p4, p12, p14, p15, p17, p18, p20, p21, p22, p26, p27, p30, p37, p38, p42, p43, p45, and p48)
2) 27 epitopes comprising mouse immunoreactive peptides+human immunoreactive peptides in >10% of IGRA+ donors (SI≥2) (epitopes: as above plus p2, p6, p19, p23, p31, p46, p47, and p50)
3) 44 epitopes comprising mouse immunoreactive peptides+human immunoreactive peptides in at least one IGRA+ donor (epitopes: as above plus p1, p3, p5, p7, p8, p10, p13, p16, p25, p28, p29, p32, p33, p36, p39, p41, p44).

Each epitope set was randomly concatenated and analyzed for 1) non-specific potential immunogenicity at epitope junctions using VaxCAD (EpiVax) and 2) potential for transmembrane insertion using TMHMM v2.0 (cbs.dtu.dk/services/TMHMM/) with rearrangements made to minimize potential of both. Immunogenicity at epitope junctions was assessed for mouse (C57BL/6) and human supertype class II alleles to generate vaccines with pre-clinical to clinical translation potential. All epitope arrangements have no predicted immunogenicity at the junctions nor potential for transmembrane insertion. No epitope arrangement required insertion of spacers between epitopes to disrupt potential junctional immunogenicity unresolved by VaxCAD. Three different vaccine designs were prepared for each concatemer: (1) concatemer with C-terminal V5 epitope tag for expression monitoring; (2) concatemer with C-terminal V5 tag and N-terminal tissue plasminogen activator (TPA) signal sequence for concatemer secretion and uptake by the exogenous antigen processing pathway; (3) concatemer with C-terminal V5 tag, N-terminal TPA signal sequence, and GPGPG (SEQ ID NO:52) spacers between epitopes for potentially enhanced antigen processing. The TPA/V5 (no spacers) constructs for the 18- and 27-epitope concatemers have been selected for initial vaccine production and testing. Although the 44-epitope concatemer vaccine design is well within the size limit accommodated by the ChAd vector, this construct was deemed of lower priority due to open questions about reduced immunogenicity of individual epitopes in the context of increased epitope number. In silico structural assessments of the predicted 18- and 27-epitope concatemer peptides (scratch.proteomics.ics.uci.edu/) detected no predicted transmembrane domains and anticipated a high likelihood of immunogenicity, consistent with the EpiVax design criteria. Concatemer structures were predicted to consist primarily of alpha-helical regions interrupted by turns or other structures, with disordered regions limited to the peptide ends, raising no obvious concerns regarding eukaryotic expression.

(SEQ ID NO: 57)
RFDLSLMLNYPNSADRYGTEITVQKASIASVLPKNAGIIRNKLKIQATI

NPDYVLNAVNHIRYKPQTQLQQSFSKRTMATQGHIINIGSISSHQVKIP

VKIIKPPFVRRGKIGVIKAIRTITGLGLKEARLGFMSFFTKAVVEALKR

FVAKLRGDLSSIIHKLMMEHLQNITNLVSTGRQGAGVAYTYNRANAG

LPTNKLSSIIHKLTSFSKTEAAQPIIHRLSTGQNTNPIARYFMVNISQL

IGEESPAVLSAAKKIFGDGAGKHFDGIKVLKLSPQNTIDHAYKLAVSST

KSMT

Fusions of the epitope concatemers to *Mycobacterium tuberculosis* HSP70 (MtbHSP70), which has multiple immune-adjuvanting activities that might promote responses to the concatemer epitopes (Leblanc et al., 2014, Hum Vaccine Immunother 10:3022; Brauns et al., 2015, Expert Rev Vaccines 14:435), are also made. Fusions of the 18-mer epitope concatemer to the N-terminus or C-terminus of Com1 and to the C-terminus of MtbHSP70, in conjunction with inclusion of the N-terminal TPA signal sequence and the C-terminal V5 expression tag, were evaluated for junctional neoepitopes. Based on the results, constructs fusing the epitope 18-mer to the N-terminus of Com1 and to the C-terminus of MtbHSP70 have been selected for production.

The compositions are administered to test animals, and an immune response is evaluated.

Construct Sequences:

18-tope (SEQ ID NO: 57)
RFDLSLMLNYPNSADRYGTEITVQKASIASVLPKNAGIIRNKLKIQATIN

PDYVLNAVNHIRYKPQTQLQQSFSKRTMATQGHIINIGSISSHQVKIPVK

IIKPPFVRRGKIGVIKAIRTITGLGLKEARLGFMSFFTKAVVEALKRFVA

KLRGDLSSIIHKLMMEHLQNITNLVSTGRQGAGVAYTYNRANAGLPTNKL

-continued

SSIIHKLTSFSKTEAAQPIIHRLSTGQNTNPIARYFMVNISQLIGEESPA

VLSAAKKIFGDGAGKHFDGIKVLKLSPQNTIDHAYKLAVSSTKSMT

27-tope (SEQ ID NO: 58)
IARYFMVNISQLIGEELSSIIHKLTSFSKTEADHAYKLAVSSTKSMTRFD

LSLMLNYPNSADRYGTEITVQKASIASVLPKNAGIIRNKLKIQATINLRP

VRYFTGVPSPVKTPELPPVTSSVAVKVPSSQGHIINIGSISSHQVVPGYR

NASSKRFVAPEAVYKGFTPLKAEDIAEASHEVLHAMSRGVEVLAKIPVKI

IKPPFVRRGQTQLQQSFSKRTMATKIGVIKAIRTITGLGLKEAAENVLII

HNKTLAHRYLAVAKLRGDLSSIIHKLRLGFMSFFTKAVVEALKRFGVAYT

YNRANAGLPTNKMMEHLQNITNLVSTGRQGAREAVLFLVTIKELLEDPSP

AVLSAAKKIFGDGATPTFVIGNKALTKFGFKAQLIQLKTHVTINATAQPI

IHRLSTGQNTNPGKHFDGIKVLKLSPQNTIPDYVLNAVNHIRYKP 44-tope (SEQ ID NO: 59)
LKPFHFISSPTRDLQIALPPVTSSVAVKVPSSRFDLSLMLNYPNSADRYG

TEITVQKASIASVLPKNAGIIRNKLKIQATINLRPVRYFTGVPSPVKTPE

SEQITLQTAEKVGLNVALKDVVALRNQAQTAKQGHIINIGSISSHQVVPG

YRNASSKRFVAPLAQYRELEAFSQFASQTQLQQSFSKRTMATEAVYKGFT

PLKAEDIAEASHEVLHAMSRGVEVLAGKHFDGIKVLKLSPQNTISDMWQA

LLAGKSGVKEHTIVVNASASEAAALQISLLVFKNSHRVQLWAKQELFVAQ

NKAMSDFMFTFRSQDSRRVQEWIKGWQEALTRMKPGAIWEIAENVLIIHN

KTLAHRYLAVARVSRLKDNFVVLEISKGTEITVQKIPVKIIKPPFVRRGK

IGVIKAIRTITGLGLKEADHAYKLAVSSTKSMTRLGFMSFFTKAVVEALK

RFVAKLRGDLSSIIHKLDGRLEQLNSQNQQLQMMEHLQNITNLVSTGRQG

AKDDILEAVANMSVMDVTGEIVKMINQAKQSIYVQGSRAFLTANKNKPGV

KTREAVLFLVTIKELLEDPSPAVLSAAKKIFGDGATPTFVIGNKALTKFG

FIDHLQQMTRQQVAMQTHKGVAYTYNRANAGLPTNKLSSIIHKLTSFSKT

EAAQPIIHRLSTGQNTNPKAQLIQLKTHVTINATPDYVLNAVNHIRYKPG

LSWLTILKKRNNYRDSFNIARYFMVNISQLIGEE

REFERENCES

1. Eldin C. Melenotte C, Mediannikov O, Ghigo E, Million M, Edouard S. et al. From Q Fever to *Coxiella burnetii* Infection: a Paradigm Change. Clin Microbiol Rev. 2017: 30(1):115-90.
2. Tigerit W D, Benenson A S, Gochenour W S. Airborne Q fever. Bacteriol Rev. 1961:25:285-93.
3. Madariaga M G, Rezai K, Trenholme G M, Weinstein R A. Q fever: a biological weapon in your backyard. Lancet Infect Dis. 2003; 3(11):709-21.
4. Kampschreur L M, Hagenaars J C, Wielders C C, Elsman P, Lestrade P J, Koning O H, et al. Screening for *Coxiella burnetii* seroprevalence in chronic Q fever high-risk groups reveals the magnitude of the Dutch Q fever outbreak. Epidemiol Infect. 2013:141(4):847-51.
5. Kampschreur L M, Oosterheert J J, Hoepelman A I, Lestrade P J, Renders N H, Elsman P. et al. Prevalence of chronic Q fever in patients with a history of cardiac valve surgery in an area where *Coxiella burnetii* is epidemic. Clin Vaccine Immunol. 2012:19(8):1165-9.
6. Ruiz S, Wolfe D N. Vaccination against Q fever for biodefense and public health indications. Front Microbiol. 2014; 5:726.
7. Chiu C K. Durrheim D N. A review of the efficacy of human Q fever vaccine registered in Australia. N S W Public Health Bull. 2007; 18(7-8):133-6.
8. Gefenaite G, Munster J M, van Houdt R, Hak E. Effectiveness of the Q fever vaccine: a meta-analysis. Vaccine. 2011; 29(3):395-8.
9. Marmion B P, Ornsbee R A, Kyrkou M, Wright J, Worswick D A, Izzo A A, et al. Vaccine prophylaxis of abattoir-associated Q fever: eight years' experience in Australian abattoirs. Epidemiol Infect. 1990; 104(2):275-87.
10. Karch C P, Burkhard P. Vaccine technologies: From whole organisms to rationally designed protein assemblies. Biochem Pharmacol. 2016; 120:1-14.
11. Zhang G, Zhang Y, Samuel J E. Components of protective immunity. Adv Exp Med Biol. 2012:984:91-104.
12. Humphres R C, Hinrichs D J. Role of antibody in *Coxiella burnetii* infection. Infect Immun. 1981:31(2): 641-5.
13. Zhang G, Russell-Lodrigue K E, Andoh M, Zhang Y. Hendrix L R, Samuel J E. Mechanisms of vaccine-induced protective immunity against *Coxiella burnetii* infection in BALB/c mice. J Immunol. 2007:179(12): 8372-80.
14. Andoh M, Zhang G, Russell-Lodrigue K E, Shive H R, Weeks B R, Samuel J E. T cells are essential for bacterial clearance, and gamma interferon, tumor necrosis factor alpha, and B cells are crucial for disease development in *Coxiella burnetii* infection in mice. Infect Immun. 2007; 75(7):3245-55.
15. Read A J, Erickson S, Harmsen A G. Role of CD4+ and CD8+ T cells in clearance of primary pulmonary infection with *Coxiella burnetii*. Infect Immun. 2010; 78(7):3019-26.
16. Dellacasagrande J, Capo C, Raoult D, Mege J L. IFN-gamma-mediated control of *Coxiella burnetii* survival in monocytes: the role of cell apoptosis and TNF. J Immunol. 1999; 162(4):2259-65.
17. Ghigo E. Capo C, Tung C H. Raoult D, Gorvel J P, Mege J L. *Coxiella burnetii* survival in THP-1 monocytes involves the impairment of phagosome maturation: IFN-gamma mediates its restoration and bacterial killing. J Immunol. 2002:169(8):4488-95.
18. Xiong X, Qi Y. Jiao J, Gong W, Duan C. Wen B. Exploratory study on Th1 epitope-induced protective immunity against *Coxiella burnetii* infection. PLoS One. 2014:9(1):e87206.
19. Reeves P M, Paul S R, Sluder A E, Brauns T A, Poznansky M C. Q-vaxcelerate: A distributed development approach for a new *Coxiella burnetii* vaccine. Hum Vaccin Immunother. 2017; 13(12):2977-81.
20. Beare P A, Chen C, Bouman T, Pablo J. Unal B, Cockrell D C, et al. Candidate antigens for Q fever serodiagnosis revealed by immunoscreening of a *Coxiella burnetii* protein microarray. Clin Vaccine Immunol. 2008; 15(12): 1771-9.
21. Chen C. Bouman T J, Beare P A. Mertens K, Zhang G Q, Russell-Lodrigue K E, et al. A systematic approach to evaluate humoral and cellular immune responses to *Coxiella burnetii* immunoreactive antigens. Clin Microbiol Infect. 2009:15 Suppl 2:156-7.

22. Chen C, Dow C. Wang P, Sidney J, Read A, Harmsen A, et al. Identification of CD4+ T cell epitopes in *C. burnetii* antigens targeted by antibody responses. PLoS One. 2011: 6(3):e17712.
23. Coleman S A, Fischer E R, Cockrell D C, Voth D E, Howe D, Mead D J, et al. Proteome and antigen profiling of *Coxiella burnetii* developmental forms. Infect Immun. 2007:75(1):290-8.
24. Kowalczewska M, Sekeyova Z, Raoult D. Proteomics paves the way for Q fever diagnostics. Genome Med. 2011; 3(7):50.
25. Li Q, Niu D, Wen B, Chen M, Qiu L. Zhang J. Protective immunity against Q fever induced with a recombinant P1 antigen fused with HspB of *Coxiella burnetii*. Ann N Y Acad Sci. 2005; 1063:130-42.
26. Vigil A. Ortega R, Nakajima-Sasaki R, Pablo J, Molina D M, Chao C C, et al. Genome-wide profiling of humoral immune response to *Coxiella burnetii* infection by protein microarray. Proteomics. 2010:10(12):2259-69.
27. Wang X, Xiong X, Graves S, Stenos J, Wen B. Protein array of *Coxiella burnetii* probed with Q fever sera. Sci China Life Sci. 2013; 56(5):453-9.
28. Wei Y, Wang X, Xiong X, Wen B. *Coxiella burnetii* antigen-stimulated dendritic cells mediated protection against *Coxiella burnetii* in BALB/c mice. J Infect Dis. 2011:203(2):283-91.
29. Xiong X. Wang X, Wen B, Graves S. Stenos J. Potential serodiagnostic markers for Q fever identified in *Coxiella burnetii* by immunoproteomic and protein microarray approaches. BMC Microbiol. 2012:12:35.
30. Carey K L, Newton H J, Luhrmann A. Roy C R. The *Coxiella burnetii* Dot/Icm system delivers a unique repertoire of type IV effectors into host cells and is required for intracellular replication. PLoS Pathog. 2011:7(5): e1002056.
31. Chen C. Banga S, Mertens K, Weber M M, Gorbaslieva I, Tan Y, et al. Large-scale identification and translocation of type IV secretion substrates by *Coxiella burnetii*. Proc Natl Acad Sci USA. 2010:107(50):21755-60.
32. Luhrmann A, Nogueira C V, Carey K L, Roy C R. Inhibition of pathogen-induced apoptosis by a *Coxiella burnetii* type IV effector protein. Proc Natl Acad Sci USA. 2010; 107(44):18997-9001.
33. Sekeyova Z. Kowalczewska M, Vincentelli R. Decloquement P, Flores-Ramirez G. Skultety L, et al. Characterization of antigens for Q fever serodiagnostics. Acta Virol. 2010:54(3):173-80.
34. van Schaik E J, Chen C. Mertens K, Weber M M, Samuel J E. Molecular pathogenesis of the obligate intracellular bacterium *Coxiella burnetii*. Nat Rev Microbiol. 2013; 11(8):561-73.
35. Voth D E. Beare P A, Howe D, Sharma U M, Samoilis G, Cockrell D C, et al. The *Coxiella burnetii* cryptic plasmid is enriched in genes encoding type IV secretion system substrates. J Bacteriol. 2011; 193(7):1493-503.
36. Voth D E, Howe D, Beare P A, Vogel J P, Unsworth N, Samuel J E, et al. The *Coxiella burnetii* ankyrin repeat domain-containing protein family is heterogeneous, with C-terminal truncations that influence Dot/Icm-mediated secretion. J Bacteriol. 2009; 191(13):4232-42.
37. Weber M M, Chen C, Rowin K, Mertens K, Galvan G. Zhi H, et al. Identification of *Coxiella burnetii* type IV secretion substrates required for intracellular replication and *Coxiella*-containing vacuole formation. J Bacteriol. 2013:195(17):3914-24.
38. UniProt Consortium T. UniProt: the universal protein knowledgebase. Nucleic Acids Res. 2018:46(5):2699.
39. Kuley R, Smith H E, Janse I, Harders F L. Baas F, Schijlen E, et al. First Complete Genome Sequence of the Dutch Veterinary *Coxiella burnetii* Strain NL3262, Originating from the Largest Global Q Fever Outbreak, and Draft Genome Sequence of Its Epidemiologically Linked Chronic Human Isolate NLhu3345937. Genome Announc. 2016; 4(2).
40. Moise L, Gutierrez A, Kibria F, Martin R. Tassone R, Liu R, et al. iVAX: An integrated toolkit for the selection and optimization of antigens and the design of epitope-driven vaccines. Hum Vaccin Immunother. 2015:11(9):2312-21.
41. Sette A, Sidney J. Nine major HLA class I supertypes account for the vast preponderance of HLA-A and -B polymorphism. Immunogenetics. 1999; 50(3-4):201-12.
42. Southwood S, Sidney J. Kondo A, del Guercio M F. Appella E, Hoffman S, et al. Several common HLA-DR types share largely overlapping peptide binding repertoires. J Immunol. 1998:160(7):3363-73.
43. De Groot A S, Martin W. Reducing risk, improving outcomes: bioengineering less immunogenic protein therapeutics. Clin Immunol. 2009:131(2):189-201.
44. Moise L, Gutierrez A H, Bailey-Kellogg C, Terry F, Leng Q, Abdel Hady K M. et al. The two-faced T cell epitope: examining the host-microbe interface with JanusMatrix. Hum Vaccin Immunother. 2013:9(7):1577-86.
45. Steere A C. Klitz W, Drouin E E, Falk B A. Kwok W W. Nepom G T, et al. Antibiotic-refractory Lyme arthritis is associated with HLA-DR molecules that bind a *Borrelia burgdorferi* peptide. J Exp Med. 2006:203(4):961-71.
46. Buchli R, VanGundy R S, Hickman-Miller H D, Giberson C F, Bardet W, Hildebrand W H. Real-time measurement of in vitro peptide binding to soluble HLA-A*0201 by fluorescence polarization. Biochemistry. 2004; 43(46): 14852-63.
47. Mangalam A K, Khare M, Krco C, Rodriguez M, David C. Identification of T cell epitopes on human proteolipid protein and induction of experimental autoimmune encephalomyelitis in HLA class II-transgenic mice. Eur J Immunol. 2004; 34(1):280-90.
48. Morroy G, Van Der Hoek W, Nanver Z D, Schneeberger P M, Bleeker-Rovers C P, Van Der Velden J, et al. The health status of a village population, 7 years after a major Q fever outbreak. Epidemiol Infect. 2016:144(6):1153-62.
49. Karagiannis I, Schimmer B, Van Lier A, Timen A, Schneeberger P, Van Rotterdam B. et al. Investigation of a Q fever outbreak in a rural area of The Netherlands. Epidemiol Infect. 2009:137(9):1283-94.
50. Morroy G, van der Hoek W, Albers J, Coutinho R A, Bleeker-Rovers C P, Schneeberger P M. Population Screening for Chronic Q-Fever Seven Years after a Major Outbreak. PLoS One. 2015; 10(7):e0131777.
51. Shiina T, Suzuki S, Ozaki Y, Taira H, Kikkawa E, Shigenari A, et al. Super high resolution for single molecule-sequence-based typing of classical HLA loci at the 8-digit level using next generation sequencers. Tissue Antigens. 2012; 80(4):305-16.
52. Sidney J, Peters B, Frahm N, Brander C, Sette A. HLA class I supertypes: a revised and updated classification. BMC Immunol. 2008; 9:1.
53. Calarota S A, Baldanti F. Enumeration and characterization of human memory T cells by enzyme-linked immunospot assays. Clin Dev Immunol. 2013; 2013: 637649.
54. Subbramanian R A, Basha S, Brady R C, Hazenfeld S, Shata M T, Bernstein D I. Age-related changes in magnitude and diversity of cross-reactive CD4+ T-cell responses to the novel pandemic H1N1 influenza hemagglutinin. Hum Immunol. 2010; 71(10):957-63.
55. Baeten L A, Podell B K, Sluder A E, Garritsen A, Bowen R A, Poznansky M C. Standardized guinea pig model for Q fever vaccine reactogenicity. PLoS One. 2018: in press.
56. Xiong X, Meng Y, Wang X, Qi Y, Li J, Duan C, et al. Mice immunized with bone marrow-derived dendritic cells stimulated with recombinant Coxiella burnetii Com1 and Mip demonstrate enhanced bacterial clearance in association with a Th1 immune response. Vaccine. 2012: 30(48):6809-15.
57. Moise L. Tassone R, Latimer H, Terry F, Levitz L, Haran J P, et al. Immunization with cross-conserved H1N1 influenza CD4+ T-cell epitopes lowers viral burden in HLA DR3 transgenic mice. Hum Vaccin Immunother. 2013:9(10):2060-8.
58. Moise L. Terry F, Ardito M, Tassone R. Latimer H, Boyle C, et al. Universal H1N1 influenza vaccine development: identification of consensus class II hemagglutinin and neuraminidase epitopes derived from strains circulating between 1980 and 2011. Hum Vaccin Immunother. 2013; 9(7):1598-607.
59. Gonzalez-Galarza F F, Takeshita L Y, Santos E J, Kempson F, Maia M H, da Silva A L, et al. Allele frequency net 2015 update: new features for HLA epitopes, KIR and disease and HLA adverse drug reaction associations. Nucleic Acids Res. 2015:43(Database issue):D784-8.
60. Schipper R F, Schreuder G M, D'Amaro J, Oudshoom M. HLA gene and haplotype frequencies in Dutch blood donors. Tissue Antigens. 1996; 48(5):562-74.
61. Baeten L A, Podell B K, Sluder A E, Garritsen A, Bowen R A, Poznansky M C. Standardized guinea pig model for Q fever vaccine reactogenicity. PLoS One. 2018:13(10): e0205882.
62. Wilhelmsen C L., Waag D M. Guinea pig abscess/hypersensitivity model for study of adverse vaccination reactions induced by use of Q fever vaccines. Comp Med. 2000:50(4):374-8.
63. Izzo A A, Marmion B P, Worswick D A. Markers of cell-mediated immunity after vaccination with an inactivated, whole-cell Q fever vaccine. J Infect Dis. 1988:157(4):781-9.
64. Jerrells T R, Mallavia L P, Hinrichs D J. Detection of long-term cellular immunity to Coxiella burnetii as assayed by lymphocyte transformation. Infect Immun. 1975:11(2):280-6.
65. Kersh G J, Fitzpatrick K A, Self J S, Biggerstaff B J, Massung R F. Long-Term immune responses to Coxiella burnetii after vaccination. Clin Vaccine Immunol. 2013: 20(2):129-33.
66. Chao C C, Chen H W, Li X. Xu W B, Hanson B, Ching W M. Identification, cloning, and expression of potential diagnostic markers for Q fever. Ann N Y Acad Sci. 2005:1063:76-8.
67. Flores-Ramirez G, Danchenko M, Quevedo-Diaz M, Skultety L. Reliable tool for detection of novel Coxiella burnetii antigens, using immobilized human polyclonal antibodies. J Chromatogr B Analyt Technol Biomed Life Sci. 2017:1047:84-91.
68. Gerlach C. Skultety L, Henning K, Neubauer H, Mertens K. Coxiella burnetii immunogenic proteins as a basis for new Q fever diagnostic and vaccine development. Acta Virol. 2017:61(3):377-90.
69. Jiao J, Xiong X, Qi Y, Gong W, Duan C, Yang X, et al. Serological characterization of surface-exposed proteins of Coxiella burnetii. Microbiology. 2014:160(Pt 12): 2718-31.
70. Papadioti A, Markoutsa S, Vranakis I, Tselentis Y, Karas M, Psaroulaki A, et al. A proteomic approach to investigate the differential antigenic profile of two Coxiella burnetii strains. J Proteomics. 2011:74(7):1150-9.
71. Sekeyova Z, Kowalczewska M, Decloquement P, Pelletier N, Spitalska E, Raoult D. Identification of protein candidates for the serodiagnosis of Q fever endocarditis by an immunoproteomic approach. Eur J Clin Microbiol Infect Dis. 2009; 28(3):287-95.
72. Vigil A, Chen C, Jain A, Nakajima-Sasaki R, Jasinskas A, Pablo J, et al. Profiling the humoral immune response of acute and chronic Q fever by protein microarray. Mol Cell Proteomics. 2011:10(10):M110 006304.
73. Xiong X, Jiao J, Gregory A E, Wang P. Bi Y, Wang X, et al. Identification of Coxiella burnetii CD8+ T-Cell Epitopes and Delivery by Attenuated Listeria monocytogenes as a Vaccine Vector in a C57BL/6 Mouse Model. J Infect Dis. 2017:215(10):1580-9.
74. Comas I. Chakravartti J, Small P M, Galagan J, Niemann S. Kremer K, et al. Human T cell epitopes of Mycobacterium tuberculosis are evolutionarily hyperconserved. Nat Genet. 2010; 42(6):498-503.
75. Ernst J D. Antigenic Variation and Immune Escape in the MTBC. Adv Exp Med Biol. 2017; 1019:171-90.
76. Tientcheu L D, Koch A, Ndengane M, Andoseh G, Kampmann B, Wilkinson R J. Immunological consequences of strain variation within the Mycobacterium tuberculosis complex. Eur J Immunol. 2017:47(3):432-45.
77. Lamonaca V, Missale G, Urbani S, Pilli M, Boni C, Mori C, et al. Conserved hepatitis C virus sequences are highly immunogenic for CD4(+) T cells: implications for vaccine development. Hepatology. 1999; 30(4):1088-98.
78. Penna A, Missale G, Lamonaca V. Pilli M, Mori C, Zanelli P, et al. Intrahepatic and circulating HILA class II-restricted, hepatitis C virus-specific T cells: functional characterization in patients with chronic hepatitis C. Hepatology. 2002:35(5):1225-36.
79. Almeida R R. Rosa D S, Ribeiro S P, Santana V C, Kallas E G, Sidney J, et al. Broad and cross-clade CD4+ T-cell responses elicited by a DNA vaccine encoding highly conserved and promiscuous HIV-1 M-group consensus peptides. PLoS One. 2012:7(9):e45267.
80. Fonseca S G, Coutinho-Silva A, Fonseca L A, Segurado A C, Moraes S L, Rodrigues H, et al. Identification of novel consensus CD4 T-cell epitopes from clade B HIV-I whole genome that are frequently recognized by HIV-1 infected patients. AIDS. 2006:20(18):2263-73.
81. Iuo A A, Marmion B P. Variation in interferon-gamma responses to Coxiella burnetii antigens with lymphocytes from vaccinated or naturally infected subjects. Clin Exp Immunol. 1993; 94(3):507-15.
82. Buttrum L, Ledbetter L, Cherla R, Zhang Y, Mitchell W J, Zhang G. Both Major Histocompatibility Complex Class I (MHC-I) and MHC-II Molecules Are Required, while MHC-1 Appears To Play a Critical Role in Host Defense against Primary Coxiella burnetii Infection. Infect Immun. 2018:86(4).
83. Li H M. Hiroi T, Zhang Y, Shi A, Chen G. De S, et al. TCRbeta repertoire of CD4+ and CD8+ T cells is distinct in richness, distribution, and CDR3 amino acid composition. J Leukoc Biol. 2016:99(3):505-13.

84. Amara R R, Nigam P, Sharma S, Liu J, Bostik V. Long-lived poxvirus immunity, robust CD4 help, and better persistence of CD4 than CD8 T cells. J Virol. 2004:78(8):3811-6.
85. Hammarlund E. Lewis M W, Hanifin J M, Mori M, Koudelka C W, Slifka M K. Antiviral immunity following smallpox virus infection: a case-control study. J Virol. 2010; 84(24):12754-60.
86. Nyendak M R, Park B, Null M D. Baseke J, Swarbrick G, Mayanja-Kizza H, et al. *Mycobacterium tuberculosis* specific CD8(+) T cells rapidly decline with antituberculosis treatment. PLoS One. 2013; 8(12):e81564.
87. Axelsson-Robertson R, Rao M, Loxton A G, Walzl G. Bates M, Zumla A, et al. Frequency of *Mycobacterium tuberculosis*-specific CD8+ T-cells in the course of anti-tuberculosis treatment. Int J Infect Dis. 2015; 32:23-9.
88. Pearce E L, Shedlock D J, Shen H. Functional characterization of MHC class II-restricted CD8+CD4– and CD8-CD4– T cell responses to infection in CD4–/– mice. J Immunol. 2004; 173(4):2494-9.
89. Ranasinghe S, Lamothe P A, Soghoian D Z, Kazer S W, Cole M B, Shalek A K, et al. Antiviral CD8(+) T Cells Restricted by Human Leukocyte Antigen Class II Exist during Natural HIV Infection and Exhibit Clonal Expansion. Immunity. 2016:45(4):917-30.
90. Kampschreur L M, Wegdam-Blans M C, Wever P C, Renders N H, Delsing C E, Sprong T. et al. Chronic Q fever diagnosis-consensus guideline versus expert opinion. Emerg Infect Dis. 2015; 21(7):1183-8.
91. Chentoufi A A, Kritzer E, Yu D M, Nesburn A B, Benmohamed L. Towards a rational design of an asymptomatic clinical herpes vaccine: the old, the new, and the unknown. Clin Dev Immunol. 2012:2012:187585.
92. Gilbert S C. T-cell-inducing vaccines—what's the future. Immunology. 2012:135(1):19-26.
93. Humphreys I R. Sebastian S. Novel viral vectors in infectious diseases. Immunology. 2018:153(1):1-9.
94. Zhang C, Zhou D. Adenoviral vector-based strategies against infectious disease and cancer. Hum Vaccin Immunother. 2016; 12(8):2064-74.
95. Zhang G, Peng Y, Schoenlaub L, Elliott A, Mitchell W, Zhang Y. Formalin-inactivated *Coxiella burnetii* phase I vaccine-induced protection depends on B cells to produce protective IgM and IgG. Infect Immun. 2013; 81(6):2112-22.
96. Desnues B, Imbert G, Raoult D, Mege J L. Ghigo E. Role of specific antibodies in *Coxiella burnetii* infection of macrophages. Clin Microbiol Infect. 2009; 15 Suppl 2:161-2.
97. Bounds C E. Terry F E, Moisc L., Hannaman D. Martin W D, De Groot A S. et al. An immunoinformatics-derived DNA vaccine encoding human class II T cell epitopes of Ebola virus, Sudan virus, and Venezuelan equine encephalitis virus is immunogenic in HLA transgenic mice. Hum Vaccin Immunother. 2017; 13(12):2824-36.
98. Peng Y, Zhang Y, Mitchell W J, Zhang G. Development of a lipopolysaccharide-targeted peptide mimic vaccine against Q fever. J Immunol. 2012; 189(10):4909-20.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising one or more isolated nucleic acids encoding a polypeptide comprising three or more epitope peptides of *Coxiella burnetti* source antigens, wherein the three or more epitope peptides are selected from the group consisting of p4, p12, p14, p15, p17, p18, p20, p21, p22, p26, p27, p30, p37, p38, p42, p43, p45, and p48, each of which consists of SEQ ID NO: 4, SEQ ID NO: 12, SEQ ID NO: 14, SEQ ID NO: 15, SEQ ID NO: 17, SEQ ID NO:18, SEQ ID NO: 20, SEQ ID NO: 21, SEQ ID NO: 22, SEQ ID NO: 26, SEQ ID NO: 27, SEQ ID NO: 30, SEQ ID NO: 37, SEQ ID NO: 38, SEQ ID NO: 42, SEQ ID NO: 43, SEQ ID NO: 45, and SEQ ID NO: 48 respectively, optionally with linkers therebetween, and a pharmaceutically acceptable carrier.

2. The composition of claim 1, wherein the polypeptide further comprises one or more of p2, p6, p19, p23, p24, p31, p46, p47, and p50 epitope peptides, each of which consists of SEQ ID NO: 2, SEQ ID NO: 6, SEQ ID NO: 19, SEQ ID NO: 23, SEQ ID NO: 24, SEQ ID NO: 31, SEQ ID NO: 46, SEQ ID NO: 47, and SEQ ID NO: 50 respectively.

3. The composition of claim 2, wherein the polypeptide further comprises one or more of p1, p3, p5, p7, p8, p10, p13, p16, p25, p28, p29, p32, p33, p36, p39, p41, and p44, each of which consists of SEQ ID NO: 1, SEQ ID NO: 3, SEQ ID NO: 5, SEQ ID NO: 7, SEQ ID NO: 8, SEQ ID NO: 10, SEQ ID NO: 13, SEQ ID NO: 16, SEQ ID NO: 25, SEQ ID NO: 28, SEQ ID NO: 29, SEQ ID NO: 32, SEQ ID NO: 33, SEQ ID NO: 36, SEQ ID NO: 39, SEQ ID NO: 41, and SEQ ID NO: 44 respectively.

4. The composition of claim 1, wherein the one or more nucleic acids are in a viral vector.

5. The composition of claim 1, wherein the one or more nucleic acids are in an adenoviral vector or a vaccinia viral vector.

6. The composition of claim 1, wherein the one or more nucleic acid a in an RNA transcript.

7. The composition of claim 1, wherein the polypeptide is a fusion protein.

8. The composition of claim 1, wherein the three or more epitope peptides are present as concatemers.

9. The composition of claim 8, wherein the polypeptide comprising the concatemers is fused to *Mycobacterium tuberculosis* Hsp70.

10. The composition of claim 1, further comprising an adjuvant, an antibiotic, or both.

11. The composition of claim 1, wherein the polypeptide is a concatenated polypeptide comprising the amino acid sequence of SEQ ID NO: 57.

12. The composition of claim 2, wherein the polypeptide is a concatenated polypeptide comprising the amino acid sequence of SEQ ID NO: 58.

13. The composition of claim 3, wherein the polypeptide is a concatenated polypeptide comprising the amino acid sequence of SEQ ID NO: 59.

* * * * *

UNITED STATES PATENT AND TRADEMARK OFFICE
CERTIFICATE OF CORRECTION

| | | |
|---|---|---|
| PATENT NO. | : 11,690,902 B2 | Page 1 of 1 |
| APPLICATION NO. | : 16/982141 | |
| DATED | : July 4, 2023 | |
| INVENTOR(S) | : Mark C. Poznansky et al. | |

It is certified that error appears in the above-identified patent and that said Letters Patent is hereby corrected as shown below:

In the Claims

In Column 73, Line 56, Claim 1, delete "burnetti" and insert -- burnetii --

In Column 75, Line 7, Claim 6, delete "acid a" and insert -- acids are --

Signed and Sealed this
Fifth Day of September, 2023

Katherine Kelly Vidal
*Director of the United States Patent and Trademark Office*

SEQUENCE LISTING

```
<160> NUMBER OF SEQ ID NOS: 59

<210> SEQ ID NO 1
<211> LENGTH: 17
<212> TYPE: PRT
<213> ORGANISM: Artificial Sequence
<220> FEATURE:
<223> OTHER INFORMATION: HLA class II epitope

<400> SEQUENCE: 1

Ser Glu Gln Ile Thr Leu Gln Thr Ala Glu Lys Val Gly Leu Asn Val
1               5                   10                  15

Ala

<210> SEQ ID NO 2
<211> LENGTH: 16
<212> TYPE: PRT
<213> ORGANISM: Artificial Sequence
<220> FEATURE:
<223> OTHER INFORMATION: HLA class II epitope

<400> SEQUENCE: 2

Thr Pro Thr Phe Val Ile Gly Asn Lys Ala Leu Thr Lys Phe Gly Phe
1               5                   10                  15

<210> SEQ ID NO 3
<211> LENGTH: 16
<212> TYPE: PRT
<213> ORGANISM: Artificial Sequence
<220> FEATURE:
```

<223> OTHER INFORMATION: HLA class II epitope

<400> SEQUENCE: 3

Lys Asp Asp Ile Leu Glu Ala Val Ala Asn Met Ser Val Met Asp Val
1               5                   10                  15

<210> SEQ ID NO 4
<211> LENGTH: 19
<212> TYPE: PRT
<213> ORGANISM: Artificial Sequence
<220> FEATURE:
<223> OTHER INFORMATION: HLA class II epitope

<400> SEQUENCE: 4

Lys Ile Gly Val Ile Lys Ala Ile Arg Thr Ile Thr Gly Leu Gly Leu
1               5                   10                  15

Lys Glu Ala

<210> SEQ ID NO 5
<211> LENGTH: 15
<212> TYPE: PRT
<213> ORGANISM: Artificial Sequence
<220> FEATURE:
<223> OTHER INFORMATION: HLA class II epitope

<400> SEQUENCE: 5

Leu Ala Gln Tyr Arg Glu Leu Glu Ala Phe Ser Gln Phe Ala Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: HLA class II epitope

<400> SEQUENCE: 6

Ser His Glu Val Leu His Ala Met Ser Arg Gly Val Glu Val Leu Ala
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: HLA class II epitope

<400> SEQUENCE: 7

Ser Arg Ala Phe Leu Thr Ala Asn Lys Asn Lys Pro Gly Val Lys Thr
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: HLA class II epitope

<400> SEQUENCE: 8

Ile Lys Gly Trp Gln Glu Ala Leu Thr Arg Met Lys Pro Gly Ala Ile
1               5                   10                  15

Trp Glu Ile

<210> SEQ ID NO 9
<211> LENGTH: 19

```
<212> TYPE: PRT
<213> ORGANISM: Artificial Sequence
<220> FEATURE:
<223> OTHER INFORMATION: HLA class II epitope

<400> SEQUENCE: 9

Ala Ile Tyr Phe Ile Gly Trp Tyr Ala Asn Leu Ala His Ile Lys Leu
1               5                   10                  15

Gly Ile Ser

<210> SEQ ID NO 10
<211> LENGTH: 17
<212> TYPE: PRT
<213> ORGANISM: Artificial Sequence
<220> FEATURE:
<223> OTHER INFORMATION: HLA class II epitope

<400> SEQUENCE: 10

Glu His Thr Ile Val Val Asn Ala Ser Ala Ser Glu Ala Ala Ala Leu
1               5                   10                  15

Gln

<210> SEQ ID NO 11
<211> LENGTH: 18
<212> TYPE: PRT
<213> ORGANISM: Artificial Sequence
<220> FEATURE:
<223> OTHER INFORMATION: HLA class II epitope

<400> SEQUENCE: 11

Pro Ile Thr Lys Lys Gln Leu Lys Thr Met Ser Asn Tyr Glu Val Ile
1               5                   10                  15

Ala Lys

<210> SEQ ID NO 12
<211> LENGTH: 18
<212> TYPE: PRT
<213> ORGANISM: Artificial Sequence
<220> FEATURE:
<223> OTHER INFORMATION: HLA class II epitope

<400> SEQUENCE: 12

Gly Lys His Phe Asp Gly Ile Lys Val Leu Lys Leu Ser Pro Gln Asn
1               5                   10                  15

Thr Ile

<210> SEQ ID NO 13
<211> LENGTH: 14
<212> TYPE: PRT
<213> ORGANISM: Artificial Sequence
<220> FEATURE:
<223> OTHER INFORMATION: HLA class II epitope

<400> SEQUENCE: 13

Phe Thr Phe Arg Ser Gln Asp Ser Arg Arg Val Gln Glu Trp
1               5                   10

<210> SEQ ID NO 14
<211> LENGTH: 15
<212> TYPE: PRT
<213> ORGANISM: Artificial Sequence
<220> FEATURE:
<223> OTHER INFORMATION: HLA class II epitope

<400> SEQUENCE: 14
```

```
Pro Asp Tyr Val Leu Asn Ala Val Asn His Ile Arg Tyr Lys Pro
1               5                  10                  15

<210> SEQ ID NO 15
<211> LENGTH: 19
<212> TYPE: PRT
<213> ORGANISM: Artificial Sequence
<220> FEATURE:
<223> OTHER INFORMATION: HLA class II epitope

<400> SEQUENCE: 15

Met Met Glu His Leu Gln Asn Ile Thr Asn Leu Val Ser Thr Gly Arg
1               5                  10                  15

Gln Gly Ala

<210> SEQ ID NO 16
<211> LENGTH: 17
<212> TYPE: PRT
<213> ORGANISM: Artificial Sequence
<220> FEATURE:
<223> OTHER INFORMATION: HLA class II epitope

<400> SEQUENCE: 16

Leu Lys Pro Phe His Phe Ile Ser Ser Pro Thr Arg Asp Leu Gln Ile
1               5                  10                  15

Ala

<210> SEQ ID NO 17
<211> LENGTH: 15
<212> TYPE: PRT
<213> ORGANISM: Artificial Sequence
<220> FEATURE:
<223> OTHER INFORMATION: HLA class II epitope

<400> SEQUENCE: 17

Lys Ile Pro Val Lys Ile Ile Lys Pro Pro Phe Val Arg Arg Gly
1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: HLA class II epitope

<400> SEQUENCE: 18

Gln Gly His Ile Ile Asn Ile Gly Ser Ile Ser Ser His Gln Val
1               5                  10                  15

<210> SEQ ID NO 19
<211> LENGTH: 18
<212> TYPE: PRT
<213> ORGANISM: Artificial Sequence
<220> FEATURE:
<223> OTHER INFORMATION: HLA class II epitope

<400> SEQUENCE: 19

Glu Ala Val Tyr Lys Gly Phe Thr Pro Leu Lys Ala Glu Asp Ile Ala
1               5                  10                  15

Glu Ala

<210> SEQ ID NO 20
<211> LENGTH: 16
<212> TYPE: PRT
```

```
<213> ORGANISM: Artificial Sequence
<220> FEATURE:
<223> OTHER INFORMATION: HLA class II epitope

<400> SEQUENCE: 20

Ala Gln Pro Ile Ile His Arg Leu Ser Thr Gly Gln Asn Thr Asn Pro
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: HLA class II epitope

<400> SEQUENCE: 21

Ile Ala Arg Tyr Phe Met Val Asn Ile Ser Gln Leu Ile Gly Glu Glu
1               5                   10                  15

<210> SEQ ID NO 22
<211> LENGTH: 19
<212> TYPE: PRT
<213> ORGANISM: Artificial Sequence
<220> FEATURE:
<223> OTHER INFORMATION: HLA class II epitope

<400> SEQUENCE: 22

Arg Leu Gly Phe Met Ser Phe Phe Thr Lys Ala Val Val Glu Ala Leu
1               5                   10                  15

Lys Arg Phe

<210> SEQ ID NO 23
<211> LENGTH: 17
<212> TYPE: PRT
<213> ORGANISM: Artificial Sequence
<220> FEATURE:
<223> OTHER INFORMATION: HLA class II epitope

<400> SEQUENCE: 23

Arg Glu Ala Val Leu Phe Leu Val Thr Ile Lys Glu Leu Leu Glu Asp
1               5                   10                  15

Pro

<210> SEQ ID NO 24
<211> LENGTH: 15
<212> TYPE: PRT
<213> ORGANISM: Artificial Sequence
<220> FEATURE:
<223> OTHER INFORMATION: HLA class II epitope

<400> SEQUENCE: 24

Leu Pro Pro Val Thr Ser Ser Val Ala Val Lys Val Pro Ser Ser
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: HLA class II epitope

<400> SEQUENCE: 25

Ser Asp Met Trp Gln Ala Leu Leu Ala Gly Lys Ser Gly Val Lys
1               5                   10                  15
```

-continued

```
<210> SEQ ID NO 26
<211> LENGTH: 15
<212> TYPE: PRT
<213> ORGANISM: Artificial Sequence
<220> FEATURE:
<223> OTHER INFORMATION: HLA class II epitope

<400> SEQUENCE: 26

Gln Thr Gln Leu Gln Gln Ser Phe Ser Lys Arg Thr Met Ala Thr
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: HLA class II epitope

<400> SEQUENCE: 27

Arg Phe Asp Leu Ser Leu Met Leu Asn Tyr Pro Asn Ser Ala Asp Arg
1               5                   10                  15

Tyr

<210> SEQ ID NO 28
<211> LENGTH: 17
<212> TYPE: PRT
<213> ORGANISM: Artificial Sequence
<220> FEATURE:
<223> OTHER INFORMATION: HLA class II epitope

<400> SEQUENCE: 28

Ile Ser Leu Leu Val Phe Lys Asn Ser His Arg Val Gln Leu Trp Ala
1               5                   10                  15

Lys

<210> SEQ ID NO 29
<211> LENGTH: 25
<212> TYPE: PRT
<213> ORGANISM: Artificial Sequence
<220> FEATURE:
<223> OTHER INFORMATION: HLA class II epitope

<400> SEQUENCE: 29

Val Ala Arg Val Ser Arg Leu Lys Asp Asn Phe Val Val Leu Glu Ile
1               5                   10                  15

Ser Lys Gly Thr Glu Ile Thr Val Gln
            20                  25

<210> SEQ ID NO 30
<211> LENGTH: 17
<212> TYPE: PRT
<213> ORGANISM: Artificial Sequence
<220> FEATURE:
<223> OTHER INFORMATION: HLA class II epitope

<400> SEQUENCE: 30

Gly Thr Glu Ile Thr Val Gln Lys Ala Ser Ile Ala Ser Val Leu Pro
1               5                   10                  15

Lys

<210> SEQ ID NO 31
<211> LENGTH: 18
<212> TYPE: PRT
<213> ORGANISM: Artificial Sequence
<220> FEATURE:
```

<223> OTHER INFORMATION: HLA class II epitope

<400> SEQUENCE: 31

Ala Glu Asn Val Leu Ile Ile His Asn Lys Thr Leu Ala His Arg Tyr
1               5                   10                  15

Leu Ala

<210> SEQ ID NO 32
<211> LENGTH: 19
<212> TYPE: PRT
<213> ORGANISM: Artificial Sequence
<220> FEATURE:
<223> OTHER INFORMATION: HLA class II epitope

<400> SEQUENCE: 32

Thr Gly Glu Ile Val Lys Met Ile Asn Gln Ala Lys Gln Ser Ile Tyr
1               5                   10                  15

Val Gln Gly

<210> SEQ ID NO 33
<211> LENGTH: 15
<212> TYPE: PRT
<213> ORGANISM: Artificial Sequence
<220> FEATURE:
<223> OTHER INFORMATION: HLA class II epitope

<400> SEQUENCE: 33

Asp Gly Arg Leu Glu Gln Leu Asn Ser Gln Asn Gln Gln Leu Gln
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: HLA class II epitope

<400> SEQUENCE: 34

Pro Ala Lys Ile Asn Leu Ala Arg Thr Tyr Ile Ala Met Glu Asp
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: HLA class II epitope

<400> SEQUENCE: 35

Val Phe Asn Ile Thr Leu Gln Lys Val Met Ala Pro Glu Leu Pro Val
1               5                   10                  15

Leu

<210> SEQ ID NO 36
<211> LENGTH: 18
<212> TYPE: PRT
<213> ORGANISM: Artificial Sequence
<220> FEATURE:
<223> OTHER INFORMATION: HLA class II epitope

<400> SEQUENCE: 36

Ile Asp His Leu Gln Gln Met Thr Arg Gln Gln Val Ala Met Gln Thr
1               5                   10                  15

His Lys

<210> SEQ ID NO 37
<211> LENGTH: 15
<212> TYPE: PRT
<213> ORGANISM: Artificial Sequence
<220> FEATURE:
<223> OTHER INFORMATION: HLA class II epitope

<400> SEQUENCE: 37

Val Ala Lys Leu Arg Gly Asp Leu Ser Ser Ile Ile His Lys Leu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: HLA class II epitope

<400> SEQUENCE: 38

Leu Ser Ser Ile Ile His Lys Leu Thr Ser Phe Ser Lys Thr Glu Ala
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: HLA class II epitope

<400> SEQUENCE: 39

Gln Glu Leu Phe Val Ala Gln Asn Lys Ala Met Ser Asp Phe Met
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: HLA class II epitope

<400> SEQUENCE: 40

Gln Asn Ala Phe Gln Leu Gln Glu Thr Ile Val Ser Thr Glu Asn
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: HLA class II epitope

<400> SEQUENCE: 41

Leu Lys Asp Val Val Ala Leu Arg Asn Gln Ala Gln Thr Ala Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: HLA class II epitope

<400> SEQUENCE: 42

Asp His Ala Tyr Lys Leu Ala Val Ser Ser Thr Lys Ser Met Thr
1               5                   10                  15

```
<210> SEQ ID NO 43
<211> LENGTH: 16
<212> TYPE: PRT
<213> ORGANISM: Artificial Sequence
<220> FEATURE:
<223> OTHER INFORMATION: HLA class II epitope

<400> SEQUENCE: 43

Asn Ala Gly Ile Ile Arg Asn Lys Leu Lys Ile Gln Ala Thr Ile Asn
1               5                   10                  15

<210> SEQ ID NO 44
<211> LENGTH: 19
<212> TYPE: PRT
<213> ORGANISM: Artificial Sequence
<220> FEATURE:
<223> OTHER INFORMATION: HLA class II epitope

<400> SEQUENCE: 44

Gly Leu Ser Trp Leu Thr Ile Leu Lys Lys Arg Asn Asn Tyr Arg Asp
1               5                   10                  15

Ser Phe Asn

<210> SEQ ID NO 45
<211> LENGTH: 17
<212> TYPE: PRT
<213> ORGANISM: Artificial Sequence
<220> FEATURE:
<223> OTHER INFORMATION: HLA class II epitope

<400> SEQUENCE: 45

Gly Val Ala Tyr Thr Tyr Asn Arg Ala Asn Ala Gly Leu Pro Thr Asn
1               5                   10                  15

Lys

<210> SEQ ID NO 46
<211> LENGTH: 15
<212> TYPE: PRT
<213> ORGANISM: Artificial Sequence
<220> FEATURE:
<223> OTHER INFORMATION: HLA class II epitope

<400> SEQUENCE: 46

Val Pro Gly Tyr Arg Asn Ala Ser Ser Lys Arg Phe Val Ala Pro
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: HLA class II epitope

<400> SEQUENCE: 47

Lys Ala Gln Leu Ile Gln Leu Lys Thr His Val Thr Ile Asn Ala Thr
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: HLA class II epitope

<400> SEQUENCE: 48
```

```
Ser Pro Ala Val Leu Ser Ala Ala Lys Lys Ile Phe Gly Asp Gly Ala
1               5                   10                  15

<210> SEQ ID NO 49
<211> LENGTH: 21
<212> TYPE: PRT
<213> ORGANISM: Artificial Sequence
<220> FEATURE:
<223> OTHER INFORMATION: HLA class II epitope

<400> SEQUENCE: 49

Asp Gln Arg Ile Thr Gln Leu Lys Asn Leu Asn Ser Asn Asn Ser Asp
1               5                   10                  15

Ser Ser Asn Asp Asn
            20

<210> SEQ ID NO 50
<211> LENGTH: 18
<212> TYPE: PRT
<213> ORGANISM: Artificial Sequence
<220> FEATURE:
<223> OTHER INFORMATION: HLA class II epitope

<400> SEQUENCE: 50

Leu Arg Pro Val Arg Tyr Phe Thr Gly Val Pro Ser Pro Val Lys Thr
1               5                   10                  15

Pro Glu

<210> SEQ ID NO 51
<211> LENGTH: 625
<212> TYPE: PRT
<213> ORGANISM: Mycobacterium tuberculosis

<400> SEQUENCE: 51

Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
```

-continued

```
            195                 200                 205
Val Asp Trp Leu Val Asp Lys Phe Lys Gly Thr Ser Gly Ile Asp Leu
210                 215                 220
Thr Lys Asp Lys Met Ala Met Gln Arg Leu Arg Glu Ala Ala Glu Lys
225                 230                 235                 240
Ala Lys Ile Glu Leu Ser Ser Gln Ser Thr Ser Ile Asn Leu Pro
                245                 250                 255
Tyr Ile Thr Val Asp Ala Asp Lys Asn Pro Leu Phe Leu Asp Glu Gln
                260                 265                 270
Leu Thr Arg Ala Glu Phe Gln Arg Ile Thr Gln Asp Leu Leu Asp Arg
            275                 280                 285
Thr Arg Lys Pro Phe Gln Ser Val Ile Ala Asp Thr Gly Ile Ser Val
290                 295                 300
Ser Glu Ile Asp His Val Val Leu Val Gly Gly Ser Thr Arg Met Pro
305                 310                 315                 320
Ala Val Thr Asp Leu Val Lys Glu Leu Thr Gly Gly Lys Glu Pro Asn
                325                 330                 335
Lys Gly Val Asn Pro Asp Glu Val Val Ala Val Gly Ala Ala Leu Gln
                340                 345                 350
Ala Gly Val Leu Lys Gly Glu Val Lys Asp Val Leu Leu Leu Asp Val
            355                 360                 365
Thr Pro Leu Ser Leu Gly Ile Glu Thr Lys Gly Gly Phe Met Thr Arg
370                 375                 380
Leu Ile Glu Arg Asn Thr Thr Ile Pro Thr Lys Arg Ser Glu Thr Phe
385                 390                 395                 400
Thr Thr Ala Asp Asp Asn Gln Pro Ser Val Gln Ile Gln Val Tyr Gln
                405                 410                 415
Gly Glu Arg Glu Ile Ala Ala His Asn Lys Leu Leu Gly Ser Phe Glu
            420                 425                 430
Leu Thr Gly Ile Pro Pro Ala Pro Arg Gly Ile Pro Gln Ile Glu Val
            435                 440                 445
Thr Phe Asp Ile Asp Ala Asn Gly Ile Val His Val Thr Ala Lys Asp
450                 455                 460
Lys Gly Thr Gly Lys Glu Asn Thr Ile Arg Ile Gln Glu Gly Ser Gly
465                 470                 475                 480
Leu Ser Lys Glu Asp Ile Asp Arg Met Ile Lys Asp Ala Glu Ala His
                485                 490                 495
Ala Glu Glu Asp Arg Lys Arg Glu Glu Ala Asp Val Arg Asn Gln
                500                 505                 510
Ala Glu Thr Leu Val Tyr Gln Thr Glu Lys Phe Val Lys Glu Gln Arg
            515                 520                 525
Glu Ala Glu Gly Gly Ser Lys Val Pro Glu Asp Thr Leu Asn Lys Val
            530                 535                 540
Asp Ala Ala Val Ala Glu Ala Lys Ala Ala Leu Gly Gly Ser Asp Ile
545                 550                 555                 560
Ser Ala Ile Lys Ser Ala Met Glu Lys Leu Gly Gln Glu Ser Gln Ala
                565                 570                 575
Leu Gly Gln Ala Ile Tyr Glu Ala Ala Gln Ala Ala Ser Gln Ala Thr
            580                 585                 590
Gly Ala Ala His Pro Gly Gly Glu Pro Gly Gly Ala His Pro Gly Ser
            595                 600                 605
Ala Asp Asp Val Val Asp Ala Glu Val Val Asp Asp Gly Arg Glu Ala
            610                 615                 620
```

Lys
625

<210> SEQ ID NO 52
<211> LENGTH: 5
<212> TYPE: PRT
<213> ORGANISM: Artificial Sequence
<220> FEATURE:
<223> OTHER INFORMATION: linker

<400> SEQUENCE: 52

Gly Pro Gly Pro Gly
1               5

<210> SEQ ID NO 53
<211> LENGTH: 4
<212> TYPE: PRT
<213> ORGANISM: Artificial Sequence
<220> FEATURE:
<223> OTHER INFORMATION: linker

<400> SEQUENCE: 53

Gly Gly Gly Ser
1

<210> SEQ ID NO 54
<211> LENGTH: 4
<212> TYPE: PRT
<213> ORGANISM: Artificial Sequence
<220> FEATURE:
<223> OTHER INFORMATION: linker

<400> SEQUENCE: 54

Gly Ser Gly Ser
1

<210> SEQ ID NO 55
<211> LENGTH: 4
<212> TYPE: PRT
<213> ORGANISM: Artificial Sequence
<220> FEATURE:
<223> OTHER INFORMATION: linkers that include cleavage sequences

<400> SEQUENCE: 55

Arg Val Lys Arg
1

<210> SEQ ID NO 56
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 56
tccatgacgt tcctgacgtt                                           20

<210> SEQ ID NO 57
<211> LENGTH: 296
<212> TYPE: PRT
<213> ORGANISM: Artificial Sequence
<220> FEATURE:
<223> OTHER INFORMATION: 18-tope concatemer

<400> SEQUENCE: 57

Arg Phe Asp Leu Ser Leu Met Leu Asn Tyr Pro Asn Ser Ala Asp Arg

```
1 5 10 15

Tyr Gly Thr Glu Ile Thr Val Gln Lys Ala Ser Ile Ala Ser Val Leu
20 25 30

Pro Lys Asn Ala Gly Ile Ile Arg Asn Lys Leu Lys Ile Gln Ala Thr
35 40 45

Ile Asn Pro Asp Tyr Val Leu Asn Ala Val Asn His Ile Arg Tyr Lys
50 55 60

Pro Gln Thr Gln Leu Gln Gln Ser Phe Ser Lys Arg Thr Met Ala Thr
65 70 75 80

Gln Gly His Ile Ile Asn Ile Gly Ser Ile Ser Ser His Gln Val Lys
85 90 95

Ile Pro Val Lys Ile Ile Lys Pro Pro Phe Val Arg Arg Gly Lys Ile
100 105 110

Gly Val Ile Lys Ala Ile Arg Thr Ile Thr Gly Leu Gly Leu Lys Glu
115 120 125

Ala Arg Leu Gly Phe Met Ser Phe Phe Thr Lys Ala Val Val Glu Ala
130 135 140

Leu Lys Arg Phe Val Ala Lys Leu Arg Gly Asp Leu Ser Ser Ile Ile
145 150 155 160

His Lys Leu Met Met Glu His Leu Gln Asn Ile Thr Asn Leu Val Ser
165 170 175

Thr Gly Arg Gln Gly Ala Gly Val Ala Tyr Thr Tyr Asn Arg Ala Asn
180 185 190

Ala Gly Leu Pro Thr Asn Lys Leu Ser Ser Ile Ile His Lys Leu Thr
195 200 205

Ser Phe Ser Lys Thr Glu Ala Ala Gln Pro Ile Ile His Arg Leu Ser
210 215 220

Thr Gly Gln Asn Thr Asn Pro Ile Ala Arg Tyr Phe Met Val Asn Ile
225 230 235 240

Ser Gln Leu Ile Gly Glu Glu Ser Pro Ala Val Leu Ser Ala Ala Lys
245 250 255

Lys Ile Phe Gly Asp Gly Ala Gly Lys His Phe Asp Gly Ile Lys Val
260 265 270

Leu Lys Leu Ser Pro Gln Asn Thr Ile Asp His Ala Tyr Lys Leu Ala
275 280 285

Val Ser Ser Thr Lys Ser Met Thr
290 295

<210> SEQ ID NO 58
<211> LENGTH: 445
<212> TYPE: PRT
<213> ORGANISM: Artificial Sequence
<220> FEATURE:
<223> OTHER INFORMATION: 27-tope concatemer

<400> SEQUENCE: 58

Ile Ala Arg Tyr Phe Met Val Asn Ile Ser Gln Leu Ile Gly Glu Glu
1 5 10 15

Leu Ser Ser Ile Ile His Lys Leu Thr Ser Phe Ser Lys Thr Glu Ala
20 25 30

Asp His Ala Tyr Lys Leu Ala Val Ser Ser Thr Lys Ser Met Thr Arg
35 40 45

Phe Asp Leu Ser Leu Met Leu Asn Tyr Pro Asn Ser Ala Asp Arg Tyr
50 55 60

Gly Thr Glu Ile Thr Val Gln Lys Ala Ser Ile Ala Ser Val Leu Pro

```
            65                  70                  75                  80
Lys Asn Ala Gly Ile Ile Arg Asn Lys Leu Lys Ile Gln Ala Thr Ile
                85                  90                  95

Asn Leu Arg Pro Val Arg Tyr Phe Thr Gly Val Pro Ser Pro Val Lys
            100                 105                 110

Thr Pro Glu Leu Pro Pro Val Thr Ser Ser Val Ala Lys Val Pro
        115                 120                 125

Ser Ser Gln Gly His Ile Ile Asn Ile Gly Ser Ile Ser Ser His Gln
    130                 135                 140

Val Val Pro Gly Tyr Arg Asn Ala Ser Ser Lys Arg Phe Val Ala Pro
145                 150                 155                 160

Glu Ala Val Tyr Lys Gly Phe Thr Pro Leu Lys Ala Glu Asp Ile Ala
                165                 170                 175

Glu Ala Ser His Glu Val Leu His Ala Met Ser Arg Gly Val Glu Val
            180                 185                 190

Leu Ala Lys Ile Pro Val Lys Ile Ile Lys Pro Pro Phe Val Arg Arg
        195                 200                 205

Gly Gln Thr Gln Leu Gln Gln Ser Phe Ser Lys Arg Thr Met Ala Thr
    210                 215                 220

Lys Ile Gly Val Ile Lys Ala Ile Arg Thr Ile Thr Gly Leu Gly Leu
225                 230                 235                 240

Lys Glu Ala Ala Glu Asn Val Leu Ile Ile His Asn Lys Thr Leu Ala
                245                 250                 255

His Arg Tyr Leu Ala Val Ala Lys Leu Arg Gly Asp Leu Ser Ser Ile
            260                 265                 270

Ile His Lys Leu Arg Leu Gly Phe Met Ser Phe Phe Thr Lys Ala Val
        275                 280                 285

Val Glu Ala Leu Lys Arg Phe Gly Val Ala Tyr Thr Tyr Asn Arg Ala
    290                 295                 300

Asn Ala Gly Leu Pro Thr Asn Lys Met Met Glu His Leu Gln Asn Ile
305                 310                 315                 320

Thr Asn Leu Val Ser Thr Gly Arg Gln Gly Ala Arg Glu Ala Val Leu
                325                 330                 335

Phe Leu Val Thr Ile Lys Glu Leu Leu Glu Asp Pro Ser Pro Ala Val
            340                 345                 350

Leu Ser Ala Ala Lys Lys Ile Phe Gly Asp Gly Ala Thr Pro Thr Phe
        355                 360                 365

Val Ile Gly Asn Lys Ala Leu Thr Lys Phe Gly Phe Lys Ala Gln Leu
    370                 375                 380

Ile Gln Leu Lys Thr His Val Thr Ile Asn Ala Thr Ala Gln Pro Ile
385                 390                 395                 400

Ile His Arg Leu Ser Thr Gly Gln Asn Thr Asn Pro Gly Lys His Phe
                405                 410                 415

Asp Gly Ile Lys Val Leu Lys Leu Ser Pro Gln Asn Thr Ile Pro Asp
            420                 425                 430

Tyr Val Leu Asn Ala Val Asn His Ile Arg Tyr Lys Pro
        435                 440                 445

<210> SEQ ID NO 59
<211> LENGTH: 734
<212> TYPE: PRT
<213> ORGANISM: Artificial Sequence
<220> FEATURE:
<223

<400> SEQUENCE: 59

Leu Lys Pro Phe His Phe Ile Ser Ser Pro Thr Arg Asp Leu Gln Ile
1               5                   10                  15

Ala Leu Pro Pro Val Thr Ser Ser Val Ala Val Lys Val Pro Ser Ser
            20                  25                  30

Arg Phe Asp Leu Ser Leu Met Leu Asn Tyr Pro Asn Ser Ala Asp Arg
        35                  40                  45

Tyr Gly Thr Glu Ile Thr Val Gln Lys Ala Ser Ile Ala Ser Val Leu
    50                  55                  60

Pro Lys Asn Ala Gly Ile Ile Arg Asn Lys Leu Lys Ile Gln Ala Thr
65                  70                  75                  80

Ile Asn Leu Arg Pro Val Arg Tyr Phe Thr Gly Val Pro Ser Pro Val
                85                  90                  95

Lys Thr Pro Glu Ser Glu Gln Ile Thr Leu Gln Thr Ala Glu Lys Val
            100                 105                 110

Gly Leu Asn Val Ala Leu Lys Asp Val Val Ala Leu Arg Asn Gln Ala
        115                 120                 125

Gln Thr Ala Lys Gln Gly His Ile Ile Asn Ile Gly Ser Ile Ser Ser
130                 135                 140

His Gln Val Val Pro Gly Tyr Arg Asn Ala Ser Ser Lys Arg Phe Val
145                 150                 155                 160

Ala Pro Leu Ala Gln Tyr Arg Glu Leu Glu Ala Phe Ser Gln Phe Ala
                165                 170                 175

Ser Gln Thr Gln Leu Gln Gln Ser Phe Ser Lys Arg Thr Met Ala Thr
            180                 185                 190

Glu Ala Val Tyr Lys Gly Phe Thr Pro Leu Lys Ala Glu Asp Ile Ala
        195                 200                 205

Glu Ala Ser His Glu Val Leu His Ala Met Ser Arg Gly Val Glu Val
210                 215                 220

Leu Ala Gly Lys His Phe Asp Gly Ile Lys Val Leu Lys Leu Ser Pro
225                 230                 235                 240

Gln Asn Thr Ile Ser Asp Met Trp Gln Ala Leu Leu Ala Gly Lys Ser
                245                 250                 255

Gly Val Lys Glu His Thr Ile Val Val Asn Ala Ser Ala Ser Glu Ala
            260                 265                 270

Ala Ala Leu Gln Ile Ser Leu Leu Val Phe Lys Asn Ser His Arg Val
        275                 280                 285

Gln Leu Trp Ala Lys Gln Glu Leu Phe Val Ala Gln Asn Lys Ala Met
290                 295                 300

Ser Asp Phe Met Phe Thr Phe Arg Ser Gln Asp Ser Arg Arg Val Gln
305                 310                 315                 320

Glu Trp Ile Lys Gly Trp Gln Glu Ala Leu Thr Arg Met Lys Pro Gly
                325                 330                 335

Ala Ile Trp Glu Ile Ala Glu Asn Val Leu Ile His Asn Lys Thr
            340                 345                 350

Leu Ala His Arg Tyr Leu Ala Val Ala Arg Val Ser Arg Leu Lys Asp
        355                 360                 365

Asn Phe Val Val Leu Glu Ile Ser Lys Gly Thr Glu Ile Thr Val Gln
370                 375                 380

Lys Ile Pro Val Lys Ile Ile Lys Pro Pro Phe Val Arg Arg Gly Lys
385                 390                 395                 400

Ile Gly Val Ile Lys Ala Ile Arg Thr Ile Thr Gly Leu Gly Leu Lys
                405                 410                 415

```
Glu Ala Asp His Ala Tyr Lys Leu Ala Val Ser Ser Thr Lys Ser Met
            420                 425                 430

Thr Arg Leu Gly Phe Met Ser Phe Phe Thr Lys Ala Val Val Glu Ala
        435                 440                 445

Leu Lys Arg Phe Val Ala Lys Leu Arg Gly Asp Leu Ser Ser Ile Ile
        450                 455                 460

His Lys Leu Asp Gly Arg Leu Glu Gln Leu Asn Ser Gln Asn Gln Gln
465                 470                 475                 480

Leu Gln Met Met Glu His Leu Gln Asn Ile Thr Asn Leu Val Ser Thr
                485                 490                 495

Gly Arg Gln Gly Ala Lys Asp Asp Ile Leu Glu Ala Val Ala Asn Met
            500                 505                 510

Ser Val Met Asp Val Thr Gly Glu Ile Val Lys Met Ile Asn Gln Ala
            515                 520                 525

Lys Gln Ser Ile Tyr Val Gln Gly Ser Arg Ala Phe Leu Thr Ala Asn
            530                 535                 540

Lys Asn Lys Pro Gly Val Lys Thr Arg Glu Ala Val Leu Phe Leu Val
545                 550                 555                 560

Thr Ile Lys Glu Leu Leu Glu Asp Pro Ser Pro Ala Val Leu Ser Ala
                565                 570                 575

Ala Lys Lys Ile Phe Gly Asp Gly Ala Thr Pro Thr Phe Val Ile Gly
            580                 585                 590

Asn Lys Ala Leu Thr Lys Phe Gly Phe Ile Asp His Leu Gln Gln Met
        595                 600                 605

Thr Arg Gln Gln Val Ala Met Gln Thr His Lys Gly Val Ala Tyr Thr
610                 615                 620

Tyr Asn Arg Ala Asn Ala Gly Leu Pro Thr Asn Lys Leu Ser Ser Ile
625                 630                 635                 640

Ile His Lys Leu Thr Ser Phe Ser Lys Thr Glu Ala Ala Gln Pro Ile
            645                 650                 655

Ile His Arg Leu Ser Thr Gly Gln Asn Thr Asn Pro Lys Ala Gln Leu
            660                 665                 670

Ile Gln Leu Lys Thr His Val Thr Ile Asn Ala Thr Pro Asp Tyr Val
        675                 680                 685

Leu Asn Ala Val Asn His Ile Arg Tyr Lys Pro Gly Leu Ser Trp Leu
        690                 695                 700

Thr Ile Leu Lys Lys Arg Asn Asn Tyr Arg Asp Ser Phe Asn Ile Ala
705                 710                 715                 720

Arg Tyr Phe Met Val Asn Ile Ser Gln Leu Ile Gly Glu Glu
                725                 730
```